(12) United States Patent
Doshi

(10) Patent No.: US 11,077,054 B2
(45) Date of Patent: *Aug. 3, 2021

(54) MEDICAL DEVICES INCLUDING MEDICAMENTS AND METHODS OF MAKING AND USING SAME INCLUDING ENHANCING COMFORT, ENHANCING DRUG PENETRATION, AND TREATMENT OF MYOPIA

(71) Applicant: Praful Doshi, San Diego, CA (US)

(72) Inventor: Praful Doshi, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/073,312

(22) Filed: Oct. 17, 2020

(65) Prior Publication Data

US 2021/0038509 A1  Feb. 11, 2021

Related U.S. Application Data

(60) Continuation of application No. 16/826,485, filed on Mar. 23, 2020, now Pat. No. 10,842,740, which is a continuation of application No. 16/524,015, filed on Jul. 27, 2019, now Pat. No. 10,632,068, which is a division of application No. 16/188,833, filed on Nov. 13, 2018, now Pat. No. 10,413,506, which is a continuation-in-part of application No. 16/158,587, filed on Oct. 12, 2018, now Pat. No. 10,369,099, which is a continuation of application No. 16/023,156, filed on Jun. 29, 2018, now Pat. No. 10,188,604, which is a division of application No. 15/898,329, filed on Feb. 16, 2018, now Pat. No. 10,076,493, which is a division of application No. 15/891,456, filed on Feb. 8, 2018, now Pat. No. 10,045,938, which is a division of application No. 13/065,904, filed on Apr. 2, 2011, now Pat. No. 9,931,296.

(60) Provisional application No. 61/341,824, filed on Apr. 3, 2010, provisional application No. 62/677,021, filed on May 27, 2018, provisional application No. 62/597,272, filed on Dec. 11, 2017.

(51) Int. Cl.
| | |
|---|---|
| A61K 9/51 | (2006.01) |
| A61K 9/00 | (2006.01) |
| C08F 220/28 | (2006.01) |
| C08L 33/08 | (2006.01) |
| A61L 27/54 | (2006.01) |
| G02B 1/04 | (2006.01) |
| A61K 31/5377 | (2006.01) |
| C08F 2/48 | (2006.01) |
| A61L 31/16 | (2006.01) |
| C08L 33/10 | (2006.01) |
| A61L 31/06 | (2006.01) |
| A61L 31/10 | (2006.01) |
| A61L 31/14 | (2006.01) |
| C08F 2/20 | (2006.01) |
| B33Y 80/00 | (2015.01) |
| A61L 12/00 | (2006.01) |
| C08L 39/06 | (2006.01) |
| A61L 12/14 | (2006.01) |
| A61L 12/08 | (2006.01) |
| C08L 33/06 | (2006.01) |

(52) U.S. Cl.
CPC ........ *A61K 9/0051* (2013.01); *A61K 31/5377* (2013.01); *A61L 27/54* (2013.01); *A61L 31/06* (2013.01); *A61L 31/10* (2013.01); *A61L 31/145* (2013.01); *A61L 31/16* (2013.01); *B33Y 80/00* (2014.12); *C08F 2/20* (2013.01); *C08F 2/48* (2013.01); *C08F 220/28* (2013.01); *C08L 33/08* (2013.01); *C08L 33/10* (2013.01); *G02B 1/043* (2013.01); *A61L 12/00* (2013.01); *A61L 12/084* (2013.01); *A61L 12/143* (2013.01); *A61L 2300/00* (2013.01); *A61L 2300/436* (2013.01); *A61L 2420/08* (2013.01); *C08L 33/066* (2013.01); *C08L 39/06* (2013.01)

(58) Field of Classification Search
None
See application file for complete search history.

(56) References Cited

U.S. PATENT DOCUMENTS

| | | | |
|---|---|---|---|
| 3,618,604 A | 11/1971 | Ness | 604/294 |
| 3,786,812 A | 1/1974 | Neefe | 424/429 |

(Continued)

FOREIGN PATENT DOCUMENTS

| | | | | |
|---|---|---|---|---|
| CA | 2794956 C | 5/2017 | | A61K 9/00 |
| EP | 0357062 | 3/1990 | | B29C 39/02 |

(Continued)

OTHER PUBLICATIONS

Yasmin et al., "Advances in Ophthalmic Drug Delivery Systems: Part I," Latest Reviews, vol. 3, Issue 2, 2005, at www.pharmmainfor.net/reviews/advances-opthalmic-drug-delivery-systems-part-i.

Yasmin et al., "Advances in Ophthalmic Drug Delivery Systems: Part II," Latest Reviews, vol. 3, Issue 2, 2005, at www.pharmmainfor.net/reviews/advances-opthalmic-drug-delivery-systems-part-ii.

Materials for Microfab, at www.microfab.com. Obtained Jun. 30, 201212 as per document itself.

(Continued)

*Primary Examiner* — David J Blanchard
*Assistant Examiner* — Daniel F. Coughlin
(74) *Attorney, Agent, or Firm* — David R. Preston

(57) ABSTRACT

The present invention recognizes that medical devices, such as but not limited to contact lenses, can be made having a coating made at least in part using printing technologies to provide drug storage and drug release structures. The coating preferably includes at least one drug reservoir layer and a least one barrier layer, and can include structures, such as but not limited to capillary structures that alone or in combination modulate the release of the drug from the coating. One aspect of the present invention is a medical device that incorporates a drug in at least one coating.

21 Claims, 11 Drawing Sheets

(56) References Cited

U.S. PATENT DOCUMENTS

| | | | |
|---|---|---|---|
| 3,828,777 A | 8/1974 | Ness | 424/427 |
| 4,558,931 A | 12/1985 | Fuhrman | 351/159.21 |
| 4,668,240 A | 5/1987 | Loshaek | 8/507 |
| 4,793,264 A | 12/1988 | Lin | 106/31.35 |
| 4,898,695 A | 2/1990 | Doshi | 264/2.6 |
| 5,018,849 A | 5/1991 | Su | 351/159.24 |
| 5,034,166 A | 7/1991 | Rawlings | 264/1.7 |
| 5,160,463 A | 11/1992 | Evans | 264/1.7 |
| 5,227,372 A | 7/1993 | Folkman | 514/58 |
| 5,270,051 A | 12/1993 | Harris | 422/423 |
| 5,271,765 A | 12/1993 | Ma | 524/83 |
| 5,271,874 A | 12/1993 | Osipo | 264/1.7 |
| 5,272,010 A | 12/1993 | Quinn | 428/411.1 |
| 5,296,228 A | 3/1994 | Chang | 424/422 |
| 5,302,978 A | 4/1994 | Evans | 351/159.24 |
| 5,389,132 A | 2/1995 | Davulcu | 130/31.58 |
| 5,414,477 A | 5/1995 | Jahnke | 351/159.28 |
| 5,480,914 A | 1/1996 | Meadows | 514/743 |
| 5,560,766 A | 10/1996 | Gundlach | 106/31.27 |
| 5,578,638 A | 11/1996 | Brazzell | 514/463 |
| 5,658,376 A | 8/1997 | Noguchi | 106/31.43 |
| 5,662,706 A | 9/1997 | Legerton | 623/5.13 |
| 5,705,194 A | 1/1998 | Wong | 424/489 |
| 5,797,898 A | 8/1998 | Santini, Jr. et al. | 604/890.1 |
| 5,837,226 A | 11/1998 | Jungherr | 424/78.1 |
| 5,888,493 A | 3/1999 | Sawaya | 424/78.04 |
| 5,905,561 A | 5/1999 | Lee | 623/6.31 |
| 5,965,320 A | 10/1999 | Evans | 430/321 |
| 6,017,875 A | 1/2000 | Kadono | 510/506 |
| 6,045,578 A | 4/2000 | Collins et al. | |
| 6,154,671 A | 11/2000 | Parel | 604/20 |
| 6,217,896 B1 | 4/2001 | Benjamin | 424/427 |
| 6,242,442 B1 | 6/2001 | Dean | 514/222.8 |
| 6,294,553 B1 | 9/2001 | Gil | 514/314 |
| 6,297,240 B1 | 10/2001 | Embleton | 514/236.2 |
| 6,315,410 B1 | 11/2001 | Doshi | 351/159.25 |
| 6,316,441 B1 | 11/2001 | Dean | 514/222.8 |
| 6,319,240 B1 | 11/2001 | Beck | 604/501 |
| 6,335,335 B2 | 1/2002 | Higashiyama | 514/231.5 |
| 6,410,045 B1 | 6/2002 | Schultz | 424/429 |
| 6,416,741 B1 | 7/2002 | Unger | 424/9.52 |
| 6,539,251 B2 | 3/2003 | Beck | 604/20 |
| 6,752,499 B2 | 6/2004 | Aller | |
| 6,834,955 B2 | 12/2004 | Doshi | 351/159.74 |
| 6,880,932 B2 | 4/2005 | Doshi | 351/159.24 |
| 6,887,858 B1 | 5/2005 | Yerxa | 514/47 |
| 6,899,426 B2 | 5/2005 | Tucker | 351/159.28 |
| 7,037,517 B2 | 5/2006 | Kataoka | 424/427 |
| 7,048,375 B2 | 5/2006 | 5232006 | |
| 7,267,846 B2 | 9/2007 | Doshi | 427/466 |
| 7,401,922 B2 | 7/2008 | Legerton | |
| 7,503,655 B2 | 3/2009 | Smith et al. | |
| 7,506,983 B2 | 3/2009 | To et al. | |
| 7,549,742 B2 | 6/2009 | Doshi | 351/159.25 |
| 7,637,612 B2 | 12/2009 | Menezes | |
| 7,638,137 B2 | 12/2009 | Chauhan | 424/429 |
| 7,674,478 B2 | 3/2010 | Kataoka | 424/429 |
| 8,071,121 B2 | 12/2011 | Chauhan | 424/429 |
| 8,075,909 B2 | 12/2011 | Chauhan | 424/429 |
| 8,221,794 B2 | 7/2012 | Hunter et al. | |
| 8,414,912 B2 | 4/2013 | Ciolino et al. | 424/429 |
| 9,101,667 B2 | 8/2015 | Raja et al. | |
| 9,125,808 B2 | 9/2015 | Alli et al. | |
| 9,295,693 B2 | 3/2016 | Cooper et al. | |
| 9,612,364 B2 | 4/2017 | Mahadevan et al. | |
| 9,827,250 B2 | 11/2017 | Chehab et al. | |
| 9,931,296 B2 | 4/2018 | Doshi | A61K 9/0051 |
| 2002/0026176 A1 | 2/2002 | Varner | 604/891.1 |
| 2002/0027638 A1 | 3/2002 | Thakrar et al. | 351/162 |
| 2002/0064513 A1 | 5/2002 | Maitra | 424/78.35 |
| 2002/0071874 A1 | 6/2002 | Olejnik | 424/661 |
| 2002/0114778 A1 | 8/2002 | Xia | 424/78.38 |
| 2002/0119941 A1 | 8/2002 | Ni | 514/44 R |
| 2002/0197300 A1 | 12/2002 | Schultz | 424/429 |
| 2003/0017199 A1 | 1/2003 | Woodward | 424/465 |
| 2003/0071964 A1 | 4/2003 | Doshi | 351/159.24 |
| 2003/0147849 A1 | 8/2003 | Warne | 424/85.2 |
| 2003/0185892 A1 | 10/2003 | Bell | 424/489 |
| 2003/0191426 A1 | 10/2003 | Lerner | 604/20 |
| 2004/0037889 A1 | 2/2004 | Richeal | 424/490 |
| 2005/0208102 A1 | 9/2005 | Schultz | |
| 2005/0244506 A1 | 11/2005 | Burke | 424/489 |
| 2006/0233860 A1 | 10/2006 | Chang | 424/427 |
| 2006/0259008 A1 | 11/2006 | Orilla | 604/521 |
| 2006/0281986 A1 | 12/2006 | Orilla | 600/398 |
| 2007/0178133 A1 | 8/2007 | Rolland | 424/423 |
| 2008/0033351 A1 | 2/2008 | Trogden | 604/57 |
| 2008/0317819 A1 | 2/2008 | Orilla | 424/429 |
| 2008/0062381 A1 | 3/2008 | Doshi | 351/159.69 |
| 2008/0075753 A1 | 3/2008 | Chappa | 424/426 |
| 2008/0107713 A1 | 5/2008 | Orilla | 424/429 |
| 2008/0131484 A1 | 6/2008 | Robinson | 424/428 |
| 2008/0260832 A1 | 10/2008 | Burke | 424/486 |
| 2008/0299178 A1 | 12/2008 | Burke | 424/428 |
| 2009/0004244 A1 | 1/2009 | Orilla | 424/429 |
| 2009/0004245 A1 | 1/2009 | Orilla | 424/429 |
| 2009/0041824 A1 | 2/2009 | Zugates | 424/423 |
| 2009/0082796 A1 | 3/2009 | Orilla | 606/167 |
| 2009/0118703 A1 | 5/2009 | Orilla | 604/521 |
| 2010/0247606 A1 | 9/2010 | Robinson | 424/426 |
| 2011/0008526 A1 | 1/2011 | Chappa | 427/2.14 |
| 2013/0202812 A1 | 8/2013 | Raja et al. | |
| 2013/0203813 A1 | 8/2013 | Mahadevan et al. | |

FOREIGN PATENT DOCUMENTS

| | | | | |
|---|---|---|---|---|
| EP | 2555751 B1 | 5/2017 | | A61K 9/00 |
| WO | WO 03/037244 A2 | 5/2003 | | |
| WO | WO 03/041690 A2 | 5/2003 | | |
| WO | WO 2004/075943 A1 | 9/2004 | | |
| WO | WO 2004/078120 A2 | 9/2004 | | |
| WO | WO 2006/110889 A2 | 10/2006 | | |
| WO | WO 2008/095307 A1 | 8/2008 | | |
| WO | WO 2009/02067 A2 | 2/2009 | | |
| WO | WO 2009/02067 A3 | 2/2009 | | |
| WO | WO 2009/020607 A2 | 2/2009 | | |
| WO | WO 2009/123624 A1 | 10/2009 | | |
| WO | WO 2009/135008 A2 | 11/2009 | | |
| WO | WO 2009/135008 A3 | 11/2009 | | |
| WO | WO 2009/137520 A2 | 11/2009 | | |
| WO | WO 2009/137520 A3 | 11/2009 | | |
| WO | WO 2011/123180 A1 | 10/2011 | | A61K 9/00 |
| WO | WO 2011/123180 A4 | 10/2011 | | A61K 9/00 |

OTHER PUBLICATIONS

Materials for Onelabs at www.onelabs.com. Obtained Jun. 30, 2012 as per document itself.

Materials for Fujifilm at www.fujifilmusa.com. Obtained Jun. 30, 2012 as per document itself.

Materials for Xerox at www.xerox.ca. Obtained Jun. 30, 2012 as per document itself.

Materials for HP Color Laser Jet at www.h10010.www1.hp.com. Obtained Jun. 30, 2012 as per document itself.

Materials for 3D Systems at www.xcorp.com. Obtained Jun. 30, 2012 as per document itself.

Materials for Stratasys at www.stratasys.com. Obtained Jun. 30, 2012 as per document itself.

*Biosig Instruments, Inc.*, v. *Nautilus, Inc.*, United States Court of Appeals for the Federal Circuit, Decided Apr. 27, 2015.

Materials from Wikipedia, "Human Eye," at en.wikipedia.org/wiki/Human_eye. Obtained Aug. 14, 2015 as per document itself.

File history materials for Issued Patent in Australia (document No. 2011233663), inclusive of Certificate of Grant dated Jul. 29, 2016 and the Issued Claims.

File history materials for Allowed Application in Canada (document No. 2,794,956), inclusive of Notice of Allowance dated Oct. 26, 2016 and the Allowed Claims.

File history materials for Allowed Application in European Patent Office—EPO (document No. 11 763 185.3-1375), inclusive of Notice of Allowance dated Sep. 11, 2016 and the Allowed Claims.

(56) References Cited

OTHER PUBLICATIONS

File history materials for Issued Patent in New Zealand (document No. 602673), inclusive of Certificate of Grant dated Jan. 6, 2015 and the Issued Claims.

File history materials for Issued Patent in Singapore (document No. 184244), inclusive of Certificate of Grant dated Jul. 30, 2015 and the Issued Claims.

Barrier Layers
( Varying diffusion rates and thicknesses )

Barrier Layers
( Varying diffusion rates and thicknesses )

3D Structure for Modulating Drug Release Rate

Using Drug Receiving Layer for Drug Reservoir

Printable Drug Reservoir

Figure 7
Uni-directional Drug Release
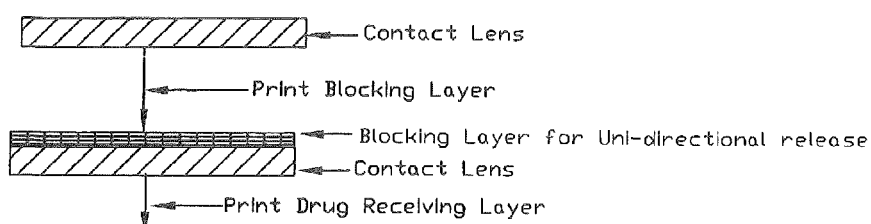
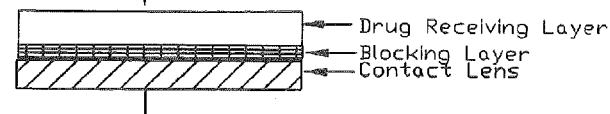
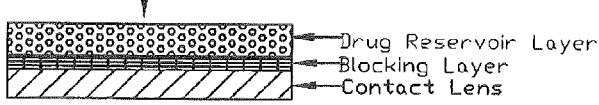
Drug Release Away From the Lens
Or Conversely
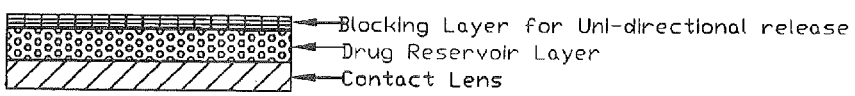
Drug Release Through the Lens

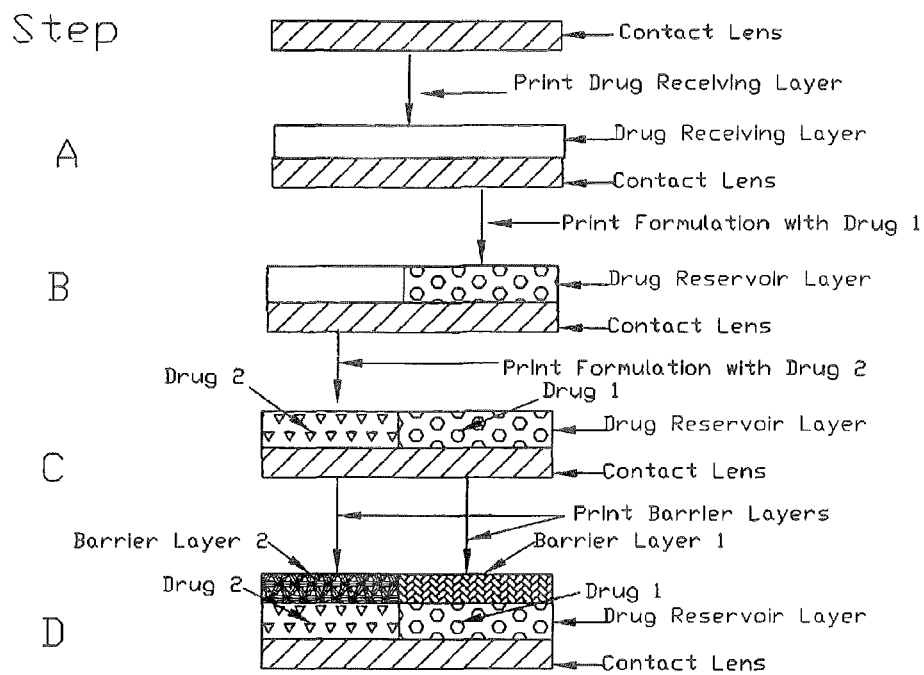
Figure 8
Multiple Drugs in Release Layer
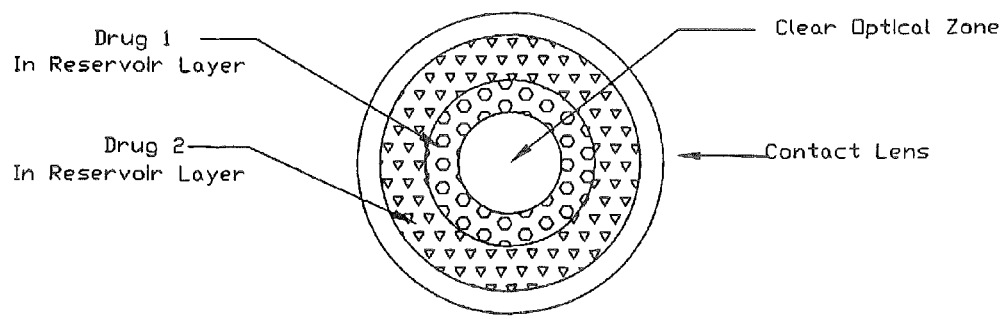
TOP VIEW

Use of Digital Printing for Embedding Drug inside the Contact Lens

Examples of Different 3D Structures to Modulate Drug Release Rate

Rate = Ra * Rb * Rc

Rate = Ra + Rb + Rc

Rate = Ra + Rb + Rc + Rcapillary

MEDICAL DEVICES INCLUDING MEDICAMENTS AND METHODS OF MAKING AND USING SAME INCLUDING ENHANCING COMFORT, ENHANCING DRUG PENETRATION, AND TREATMENT OF MYOPIA

The Present Application is:
a Continuation of U.S. Utility patent application Ser. No. 16/826,485, filed Mar. 23, 2020, which is
a Continuation of U.S. Utility patent application Ser. No. 16/524,015, filed Jul. 27, 2019, which is
a Divisional of U.S. Utility patent application Ser. No. 16/188,833, filed Nov. 13, 2018, now U.S. Pat. No. 10,413,506, issued Sep. 17, 2019; which is
a Continuation-in-Part of U.S. Utility patent application Ser. No. 16/158,587, filed Oct. 12, 2018, now U.S. Pat. No. 10,369,099, issued Aug. 6, 2019; which is
a Continuation of U.S. Utility patent application Ser. No. 16/023,156, filed Jun. 29, 2018, now U.S. Pat. No. 10,188,604, issued Jan. 29, 2019; which is
a Divisional Application of U.S. Utility patent application Ser. No. 15/898,329, filed Feb. 16, 2018, now U.S. Pat. No. 10,076,493, issued Sep. 18, 2018; which is
a Divisional Application of U.S. Utility patent application Ser. No. 15/891,456, filed Feb. 8, 2018, now U.S. Pat. No. 10,045,938, issued Aug. 14, 2018; which is
a Divisional Application of U.S. Utility patent application Ser. No. 13/065,904, filed Apr. 2, 2011, now U.S. Pat. No. 9,931,296, issued Apr. 3, 2018; which
claims benefit of priority to U.S. Provisional application No. 61/341,824, filed Apr. 3, 2010;
each of which is incorporated by reference in its entirety herein.
In addition, U.S. Utility patent application Ser. No. 16/188,833 also claims benefit of priority to:
U.S. Provisional Application No. 62/677,021, filed May 27, 2018; and
U.S. Provisional Application No. 62/597,272, filed Dec. 11, 2017;
each of which is incorporated by reference in its entirety herein.

TECHNICAL FIELD

The present invention generally relates generally to the fields of medical devices, including but not limited to contact lenses, that include a medicament or drug in a coating layer and methods of making and using such medical devices. The coating layer is preferably made at least in part using printing, preferably but not limited to digital printing.

BACKGROUND

Medical devices that include a medicament have been known. Examples include contact lenses and stents for the treatment or prevention of a variety of diseases, disorders or conditions, such as contact lenses for the treatment of glaucoma and stents for the treatment or prevention of restenosis. Existing medical devices that include medicaments are traditionally made using relatively simple drug coating or drug impregnation technologies that do not allow the modulated release of the medicament from the coating. The present invention addresses these limitations and provides additional benefits as well.

A variety of medical devices, particularly contact lenses, that include a medicament have been described. For example, U.S. Pat. No. 7,638,137B2 to Chuahan et al. describes drug delivery systems through dispersion of transparently encapsulated drugs within the lens. However, such dispersion inside the lens could alter the physical properties of the polymeric lens materials. Also, while encapsulated drugs may be visually transparent in certain instances, the may interfere with the optical properties of the lens. Also, drugs inside the lens may be released from either or both the anterior and posterior surfaces of the lens and thus not providing the desired dosage of a drug to the cornea or other areas of an eye structure and surrounding tissues. This document also provides a survey of the literature relating to issues relating to drug release.

U.S. published Patent Application No. 2009/07504245A1 to Orilla et al. describe the masking of a color of a drug by applying a color layer on top of the drug. This document does not relate to the controlling the drug release rate from the lens.

Also, U.S. published Patent Application No. 2009/0004244 to Burke et al. describes deposing a drug in an iris simulated pattern to provide a cosmetic appearance of a lens for drug delivery. This document does not relate to how drug release rate can be controlled.

In addition, U.S. Pat. No. 6,887,858 to Yerxa describes formulations for the treatment of dry eye diseases. The document is not related to drug release from a medical device such as a contact lens.

Furthermore, U.S. Pat. No. 6,294,553 to Gil et al. describes a drug for ocular surface pain. Gil et al. does not, however relate to controlled drug delivery rate.

U.S. Pat. No. 3,786,812 to Neefe describes the use of contact lenses for drug delivery. This document, however, does not relate to achieving desired release rate of a drug from a lens.

Also, U.S. Pat. Nos. 3,618,604, 3,828,777 describe polymeric plastics in which a drug is held to provide controlled drug release rate. The documents, however, do not relate to the ability to adjust drug release rate.

BRIEF DESCRIPTION OF THE FIGURES

FIG. 7 depicts one aspect of the invention where there is a uni-directional or near uni-directional release of a drug from the medical device such as but not limited to a contact lens utilizing a blocking layer that prevents release of a drug in one direction.

FIG. 8 depicts one aspect of the invention where it is desirable to provide two or more different drugs, such as but not limited to one for glaucoma and another for comfort enhancement of a medical device such as but not limited to contact lenses such as but not limited to for dry eye at the same time or at different times. This figure depicts the use of concentric layers of two drugs whereas FIG. 4 depicts the use of providing separate layers of drugs at different heights and thicknesses of a drug reservoir layer to achieve this function and related structure for release of two different drugs at the same time or at different times.

SUMMARY

Figure 1:
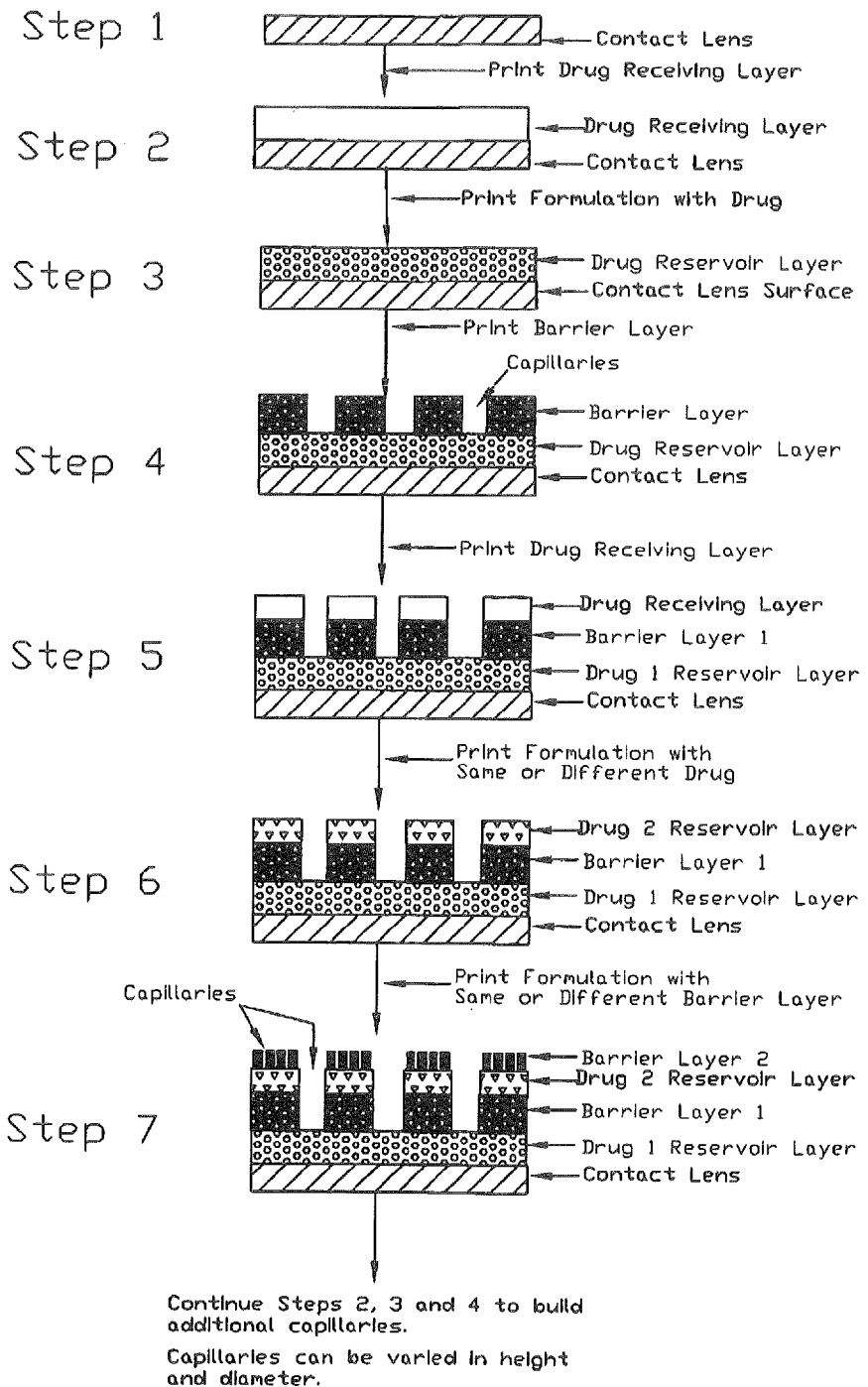
FIG. 1 depicts a step-by-step construction of a 3D structure on surface of a medical device such as but not limited to a contact lens. These steps include constructing one or more drug reservoir layer, barrier layers of different diffusivity along with capillaries of different heights. All these structures are created to obtain a desirable drug release rate.

The present invention recognizes that medical devices, such as but not limited to contact lenses, can be made having at least one coating layer made at least in part using printing technologies to provide drug storage and drug release structures. The at least one coating layer preferably includes at least one drug reservoir layer and a least one barrier layer, and can include structures, such as but not limited to capillary structures, which alone or in combination modulate the release of the drug from the coating.

A first aspect of the present invention is a medical device that incorporates at least one drug in at least one coating, where the at least one coating includes at least one drug reservoir layer and at least one barrier layer.

A second aspect of the present invention is a method of making a medical device that incorporates at least one drug in at least one coating, where the at least one coating includes at least one drug reservoir layer and at least one barrier layer.

A third aspect of the present invention is a method of using a medical device of the present invention to treat or prevent a disease, disorder or condition.

DETAILED DESCRIPTION OF THE INVENTION

Definitions

Unless defined otherwise, all technical and scientific terms used herein have the same meaning as commonly understood by one of ordinary skill in the art to which this invention belongs. Generally, the nomenclature used herein and the laboratory procedures well known and commonly employed in the art. Conventional methods are used for these procedures, such as those provided in the art and various general references such as U.S. Pat. Nos. 5,160,463; 5,271,874; 5,018,849; 5,034,166; 5,414,477; 6,315,410; 6,899,426B2; 7,638,137B2; US Published Patent Application US2009/0062381A1; Day et al., Current Optometric Information and Terminology, Third Edition, American Optometric Association (1980); Howley's Condensed Chemical Dictionary (1981); Federation of Societies for Coatings Technology; and "Contact Lenses for Drug Delivery: Achieving Sustained Release with Novel Systems," Alvarez Lorenzo et. al. American Journal of Drug Delivery, (2006) 4 (3) (3) (5). Where a term is provided in the singular, the inventors also contemplate the plural of that term. The nomenclature used herein and the laboratory procedures described below are those well-known and commonly employed in the art. As employed throughout the disclosure, the following terms, unless otherwise indicated, shall be understood to have the following meanings:

"Directly" refers to direct causation of a process that does not require intermediate steps.

"Indirectly" refers to indirect causation that requires intermediate steps.

"Digitally Encoded Image" or "Digital Image" refers to an image that has been created or stored in a digital format. A digitally encoded image can be made using methods known in the art, such as artistic renditions or scanning or otherwise translating an image. A digitally encoded image can be stored on appropriate storage medium, such as magnetic medium or polymers such as cyclo-olefin copolymers. A plurality of digitally encoded images can be stored together or separately to form a database of digitally encoded images that are accessible individually or in combination. Such digitally encoded images can be altered using established methods, such as artistic renditions or image modulating software. A plurality of images can also be merged to form a new digitally encoded image.

"Solvent" refers to an aqueous, organic or inorganic solvent, such as water, isopropanol, tetrahydrofuran or acetone.

"Surfactant" refers to a surfactant as that term is known in the art, such as, for example, acetylene glycol or polyoxyethylene alkyl.

"Dispersant" refers to dispersants as they are known in the art, such as, for example, the Tergitol series from Union Carbide, polyoxylated alkyl ethers, alkyl diamino quaternary salts or "Pecegal "O"" from GAF (U.S. Pat. No.

5,560,766). Dispersants are preferably used at between about 0.1% and about 10%, more preferably between about 0.5% and about 5%.

"Lens" as used herein refers to a composition of matter that can transmit light. A lens preferably can act as an optical lens, such as a contact lens. In certain aspects of the present invention, a lens need not act as an optical lens, such as a contact lens that is used for therapeutic purposes as opposed to purposes relating to the correction, improvement or alteration of a user's eyesight.

"Contact Lens" refers to a structure that can be placed on or within a wearer's eye. A contact lens can correct, improve, or alter a user's eyesight, but that need not be the case. A contact lens can be of any appropriate material known in the art or later developed, and can be a soft lens, a hard lens or a hybrid lens. A contact lens can be in a dry state or a wet state.

"Soft Lens" refers to a variety of soft lenses as they are known in the art that are characterized as having, for example, at least one of the following characteristics: oxygen permeable, hydrophilic or pliable.

"Hard Lens" refers to a variety of hard lenses as they are known in the art that are characterized as having, for example, at least one of the following characteristics: hydrophobic, gas permeable or rigid.

"Hybrid Lens" refers to a variety of hybrid lenses as they are known in the art, such as, for example, a lens having a soft skirt and a hard center.

"Dry State" refers to an article of manufacture or a portion thereof in a state prior to hydration or the state of an article of manufacture or a portion thereof under storage or use conditions.

"Wet State" refers to an article of manufacture or a portion thereof in a hydrated state.

"Transparent" refers to a substantial portion of visible light transmitted through a structure, such as greater than or equal to 90% of incident light.

"Opaque" refers to a substantial portion of visible light reflected or absorbed by a structure, such as greater than or equal to 90% of incident light.

"Partially opaque" refers to a combination of transparent and opaque.

"Hydrogel" refers to a polymer that swells in an aqueous solution due to the absorbance of water. A hydrogel includes water or an aqueous solution as part of its structure.

"Polymer" refers to a linkage of monomers. Preferably, a polymer is a polymer appropriate for use in lenses, such as contact lenses. A polymer can be, for example, a homopolymer, a heteropolymer, a copolymer, a hydrophobic polymer, a hydrophilic polymer or any combination thereof.

"Hydrophobic Polymer" refers to a polymer that does not absorb an appreciable amount of water or an aqueous solution (see, U.S. Pat. No. 5,034,166).

"Hydrophilic Polymer" refers to a polymer that absorbs an appreciable amount of water or an aqueous solution (see, U.S. Pat. No. 5,034,166). Lens forming materials that are suitable in the fabrication of contact lenses are illustrated by one or more of the following U.S. Pat. Nos. 2,976,576; 3,220,960; 3,937,680; 3,948,871; 3,949,021; 3,983,083; 3,988,274; 4,018,853; 3,875,211; 3,503,942; 3,532,679; 3,621,079; 3,639,524; 3,700,761; 3,721,657; 3,758,448; 3,772,235; 3,786,034; 3,803,093; 3,816,571; 3,940,207; 3,431,046; 3,542,461; 4,055,378; 4,064,086; 4,062,624; and 5,034,166.

"Hydrophilic Monomer" refers to monomers used to make soft lenses, such as hydroxyethylmethacrylate, methacrylic acid, or N-vinylpyrrolidone (U.S. Pat. Nos. 5,271,874; 5,272,010).

"Hydrophilic Monomer" refers to monomers used to make hard lenses, such as methylmethacrylate, ethoxyethylmethacrylate, styrene, or silicone (U.S. Pat. Nos. 5,271,874; 5,272,010).

"Homopolymer" refers to a polymer comprising a single type of monomer such as hydroxyethylmethacrylate.

"Heteropolymer" refers to a polymer comprising more than one type of monomer such as hydroxyethylmethacrylate and methacrylic acid.

"Copolymer" refers to the use of two different polymers to make a polymer chain.

"Acrylic Polymer" or "Acrylics" refers to a variety of polymer of that genus and species as they are known in the art, such as, for example, hydroxyethylmethacrylate.

"Silicone Polymer" or "Silicones" refers to a variety of polymers of that genus and species as they are known in the art, such as, for example Tris (such as Tris (pentamethyldisiloxyanyl)-3-methacrylate-propylsilane or 3-methacryloxypropy tris(trimethylsiloxy)silane).

"Polycarbonate Polymer" or "Polycarbonate" refers to a variety of polymers of that genus and species as they are known in the art, such as, for example Lexan.

"Initiator" in the context of polymerization refers to an initiator as that term is known in the art, such as, for example, a chemical that starts a polymerization reaction.

"UV Initiator" in the context of polymerization refers to a UV initiator as that term is known in the art, such as, for example, a chemical that becomes reactive or active with the adsorption of energy, such as UV energy, such as, for example benzoin methyl ether.

"Binder" or "bonding agent" refers to compounds used perform the function of increasing the interaction between moieties, such as between monomers and polymers such as those terms are known in the art. Examples of binders or binding agents are hexamethylene diisocyanate or other isocyanate compounds.

"Thickener" refers to a compound that is used to increase the viscosity of a liquid or partially liquid mixture or solution such as that term is known in the art. An example of a thickener is polyvinyl alcohols.

"Anti-kogating agent" or "non-kogating agent" refers to compounds that facilitate printing processes that utilize nozzles, such as such terms are known in the art.

"Dispersant" refers to a surface-active agent added to a suspending medium to promote the distribution and separation of fine or extremely fine solid particles.

"Thermal Initiator" in the context of polymerization refers to a thermal initiator as that term is known in the art, such as, for example, a chemical that becomes active or reactive with the absorption of heat energy, such as, for example, Vazo-64 or azobisisobutyronitrile.

"Anti-Bacterial Agent" refers to a compound or composition that can act as a bactericidal or bacteriostatic or can reduce the growth rate of a bacteria such as tetrabutylammonium chloride.

"Anti-Fungal Agent" refers to a compound or composition that can act as a fungicidal or fungistatic or can reduce the growth rate of a fungi such as benzalkonium chloride salicylic acid.

"Disinfectant" refers to a compound or composition that can reduce the type, number or diversity of microorganisms.

"Humectant" refers to compounds that reduce evaporation, such as ethylene glycol.

"Printing" refers to the application of at least one printing formulation to a surface or structure. Printing can use any appropriate device or method known in the art of later developed for a particular purpose.

"Printing Device" refers to any appropriate device for printing on a surface or structure known in the art or later developed for a particular purpose. Preferably, a printing device includes the dispensation of microdroplets of liquid. The size or volume of the microdroplets can vary, but generally the smaller the microdroplet, the higher the quality of the printing produced. Preferred microdroplets are between about 1 picoliter and about 1,000 microliters, preferably between about 10 picoliters and about 10 microliters or between about 100 picoliters and about 1 microliter. Preferred microdroplets can also be in the microliter range.

"Ink Jet Printing" refers to printing using a printing device that comprises at least one ink jet. Such printing devices are commercially available such as through, for example, Hewlett Packard Corporation (such as DeskJet 560C printer cartridges) and Encad Corporation.

"Piezo Printing" refers to printing using a printing device that comprises at least one piezo printing structure. Such piezo printing structures are known in the art, such as, for example, those available through Packard Instruments and Hewlett Packard Corporation or Canon Inc.

"Thermal Printing" refers to printing using a printing device that comprises at least one thermal printing structure. Such thermal printing structures are known in the art, such as, for example, those available through Hewlett Packard Corporation.

"Laser Printing" refers to printing using a printing device that uses at least one laser printing structure. Such printing structures are known in the art, such as, for example, those available through Cannon or Hewlett Packard Corporation.

"Pad Transfer Printing" refers to printing using a pad transfer printing device. Such pad transfer printing devices are known in the art, particularly for printing in the field of contact lenses. Briefly, a layer is placed or printed on a pad transfer device and the layer on the pad transfer device is transferred to another surface, such as a polymer or lens or other surface (U.S. Pat. No. 3,536,386 to Spivack, issued Oct. 27, 1970; U.S. Pat. No. 4,582,402 to Knapp, issued Apr. 15, 1986; U.S. Pat. No. 4,704,017 to Knapp, issued Nov. 3, 1987; U.S. Pat. No. 5,034,166 to Rawlings et al., Jul. 23, 1991; U.S. Pat. No. 5,106,182 to Briggs et al., issued Apr. 21, 1992; U.S. Pat. No. 5,352,245 to Su et al., issued Oct. 4, 1994; U.S. Pat. No. 5,452,658 to Shell, issued Sep. 26, 1995 and U.S. Pat. No. 5,637,265 to Misciagno et al., issued Jun. 10, 1997).

"Impregnation" refers to a drug being contacted with a surface, such as a polymer, and the drug diffuses into the polymer (EP 0357062 to Pfortner, published Mar. 7, 1990).

"Chemical Bond" refers to a covalent bond or non-covalent bond.

"Polymer-Polymer Bond" refers to two polymers forming covalent or non-covalent bonds, such as by cross linking polymers formed between two polymers, such as hydroxyethyl methylacrylate and ethyleneglycoldimethacrylate.

"Dry State" refers to a polymer that is not fully hydrated.

"Wet State" refers to a polymer that is fully hydrated.

"Forming a Lens" or "Fabricating a Lens" refers to any method or structure known in the art or later developed used to form a lens. Such forming can take place, for example, using cast-molding, spin-casting, cutting, grinding, laser cutting, stamping, trimming, engraving, etching or the like (U.S. Pat. No. 4,558,931 to Fuhrman, issued Dec. 17, 1985).

"Cast-Molding" in the context of forming a lens refers to the formation of at least a portion lens using a mold (U.S. Pat. No. 3,536,386 to Spivak, issued Oct. 27, 1970; U.S. Pat. No. 3,712,718 to LeGrand et al., issued Jan. 23, 1973; U.S. Pat. No. 4,582,402 to Knapp, issued Apr. 15, 1986; U.S. Pat. No. 4,704,017 to Knapp, issued Nov. 3, 1987; U.S. Pat. No. 5,106,182 to Briggs et al., issued Apr. 21, 1992; U.S. Pat. No. 5,160,463 to Evans et al., issued Nov. 3, 1992; U.S. Pat. No. 5,271,874 to Osipo et al., issued Dec. 21, 1993 and EP 0357062 to Pfortner, published Mar. 7, 1990)

"Spin-Casting" in the context of forming a lens refers to the formation of a lens using centrifugal force (U.S. Pat. No. 3,557,261 to Wichterle, issued Jan. 19, 1971 and U.S. Pat. No. 5,034,166 to Rawlings et al., issued Jul. 23, 1991).

"Information Storage Medium" refers to any medium of expression that can store information in any appropriate format either permanently or transiently. Preferred information storage medium includes paper, electronic medium, magnetic medium or polymers, such as cyclo-olefin copolymers.

"Electronic Medium" refers to information storage medium that can store information in electronic form. For example, electronic medium includes magnetic storage medium, such as diskettes.

"Machine Readable Format" refers to information stored on or within an information storage medium in a form, language or arrangement such that a machine, such as a central processing unit (CPU) can access and use the information.

"Database" refers to a collection of information, such as digital images. The information is preferably provided on or within an information storage medium and can be separate from or integral with a central processing unit.

"Printable formulation" refers to a printable formulation that can be used in conjunction with a printing technology or printing device to provide at least one structure, at least one layer, or a combination thereof, of the present invention.

"Subject" refers to, but is not limited to, a human or non-human primate; a companion animal such as but not limited to a dog, a cat, a bird, a fish, a reptile, an amphibian, a fox, a wolf, a pig, a horse or other companion as is known in the art; laboratory animal, such as, but not limited to a mouse, a rat, a guinea pig, a rabbit, a dog, a cat, a ferret, a pig, or other laboratory animals as is known in the art; working animals such as but not limited to a dog, a horse or other working animals as are known in the art; or any other animal as in known in the art that may be in need of the technology of the present invention or for testing of the technology of the present invention.

"Digital printing" refers to the printing of at least a portion of a layer of the present invention using at least one digital image printing technology.

"3D printing" or "three dimensional printing" refers to the printing of three-dimensional structures using appropriate printing technologies and printers as are known in the art or later developed. 3D printing is useful in the making of parts, products or layers using a computer-driven, additive process, one or more layers at a time. 3D printing can build parts or other structures such as layers, using any appropriate material, such as, but not limited to plastic or metal, directly from CAD drawings or other digital images that have been preferably cross sectioned into may, if not hundreds or thousands of layers. 3D printing provides a faster and less costly alternative to machining, such as but not limited to machining, including but not limited to cutting, turning, grinding and drilling of materials, such as solid materials. Although various techniques are used in 3D printing in the relevant art, 3D printers use method of additive fabrication, that is the building a part or structure one layer at a time, with layers ranging in thickness from about a millimeter to less than 1/1,000 of an inch. The building material can be in any appropriate form, such as, but not limited to a liquid, a power or a sheet of material that is cured by heat, UV light, a chemical reaction or other appropriate method.

Other technical terms used herein have their ordinary meaning in the art that they are used, as exemplified by a variety of technical dictionaries.

Introduction

The present invention recognizes that medical devices, such as but not limited to contact lenses, can be made having at least one coating made at least in part using printing technologies to provide drug storage and drug release structures. The coating preferably includes at least one drug reservoir layer including at least one drug, and a least one barrier layer. The at least one barrier layer can include structures, such as but not limited to capillary structures, that alone or in combination, modulate the release of the drug from the coating.

As a non-limiting introduction to the breath of the present invention, the present invention includes several general and useful aspects, including:

1) A medical device that incorporates a drug. The medical device includes a coating that includes at least one drug reservoir layer that includes a drug and at least one barrier layer.

2) A method of making a medical device that incorporates a drug. The medical device includes a coating that includes at least one drug reservoir layer that includes a drug and at least one barrier layer. The coating is made at least in part using printing.

3) A method of using a medical device of the present invention to treat or prevent a disease, disorder or condition. The medical device can be implantable or non-implantable and is placed at a location in a subject appropriate for treating or preventing a disease, disorder or condition.

These aspects of the invention, as well as others described herein, can be achieved by using the methods, articles of manufacture and compositions of matter described herein. To gain a full appreciation of the scope of the present invention, it will be further recognized that various aspects of the present invention can be combined to make desirable embodiments of the invention.

I Medical Devices Including a Medicament

The present invention includes an article of manufacture that includes: a) a medical device including at least one surface; and b) one or more coatings provided on at least a portion of the at least one surface. The coating includes: 1) at least one drug reservoir layer produced at least in part by printing, wherein the at least one drug reservoir layer includes at least one drug; and 2) at least one barrier layer including one or more structures produced at least in part by printing. The at least one barrier layer modulates the release of the at least one drug from the at least one drug reservoir layer (see, for example, FIG. 2 and FIG. 3).

Medical Device

The medical device of the present invention can be any known in the art or later developed. The medical device can be implanted within a subject as is the case with many medical devices as they are known in the art such as, for example, cardiac stents, joint replacements such a hip and knee among others, birth control sticks, pacemakers, breast implants, facial implants for reconstructive or cosmetic purposes such as for the cheeks and chin, intrauterine devices (IUD's), pins and mesh and resorbable materials such as known in the art (such as, but not limited to, polylactic acid (PLA)) for bone reconstruction or immobilization, dental implants, filters to entrap blood clots in blood vessels, optical lens replacements for cataract treatment, voice boxes for throat cancer patients and the like.

The medical device of the present invention can also be non-implantable as they are know in the art, such as, for example, contact lenses, dental apparatus, drug patches, transdermal drug patches including but not limited to birth control, Alzheimer's patches, smoking cessation patches, hearing aids, earplugs or other devices inserted into the ear to treat swimmer's ear and ear infections and the like.

The medical device of the present invention can be made of any appropriate material or combination of materials as appropriate for the purpose and location where the medical device will ultimately reside within or on a subject. The choice of materials for the medical device is determinable by one skilled in the art, and there are numerous examples in the prior art for the skilled artisan to follow. For the present invention, it is generally the surface of the medical device on which a coating is provided, but this need not be an exclusive requirement.

Surface

The surface of a medical device that is to be coated in the manner of the present invention can be of any appropriate material and is usually determined or influenced by the nature of the medical device and where, and how long, it is to be implanted, or not implanted, within or on a subject.

Many medical devices present metal on their surface. Examples include, but are not limited to, bone pins and mesh for bone repair and stabilization. Metals that can be used as a surface include, for example, steal, stainless steel, gold, silver and the like.

Some medical devices present a plastic or polymer on their surface. Examples include but are not limited to contact lenses, IUD's an implantable birth control sticks. There are a wide variety of polymers and plastics available for use in medical devices, which are too numerous to enumerate here. Individual polymers and plastics are discussed further herein, and are intended as a limiting list of such materials.

Other medical devices present partially polymerized polymers during their manufacture, but not necessarily in the final product. The partially polymerized polymers can be used as an intermediate product to facilitate bonding with other components of the device. Examples include, but are not limited to, contact lenses and the like.

Still other medical devices present on their surface polymer matrices. Examples include, but are not limited to, limited to materials that allow for skin or other tissue regenerations, such as for trauma, disease, disorder, condition such as, for example, burn treatment, such as those that contain fibronectin or other structural proteins. The polymer matrix or protein matrix can be any appropriate, such as but not limited to proteins, nucleic acids, and carbohydrates.

In addition, still other medical devices present on their surface silicone, ceramic, glass, carbon (inclusive of nanotubes and graphite) and fabric. Examples include, but are not limited to, breast implants, penal implants, hip replacement parts, knee replacement parts, bandages for burn and trauma wounds, and the like. The silicone, ceramic, glass, carbon (including but not limited to graphite including sheets, carbon nano-structures such as tubes, balls, sheets and other structures) and fabric can be any appropriate and as are realized in the art.

The surface of a medical device can also be pretreated or modified by various processes to, in some instances, clean or otherwise prepare the surface for receiving the coating of the present invention. Some pretreatments may be physical in nature, such as polishing, scarring or scoring, whereas others may be chemical in nature. Preferred chemical process include, but are not limited to, chemical coating, chemical cleaning, chemical texture modification, chemical or electrochemical activation or creation of reactive groups on or within said at least one surface, application of one or more chemicals to said at least one surface, and combinations thereof.

Drug Resevoir Layer

Figure 5:
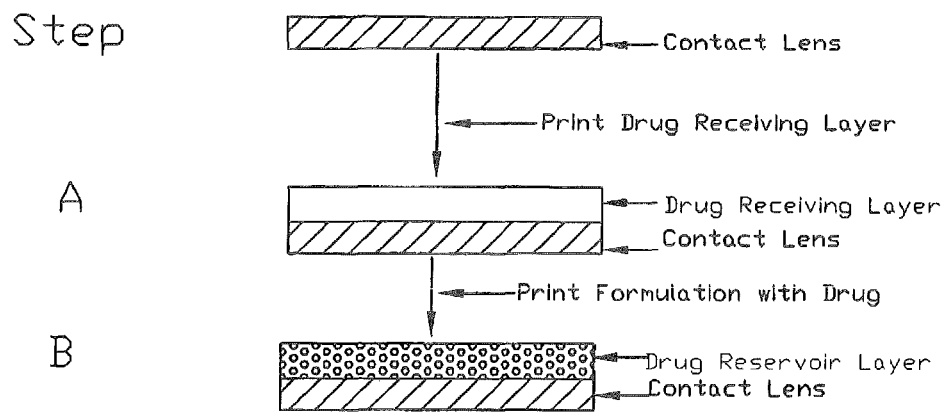
FIG. 5 depicts the application of a drug receiving layer on the surface of a medical device such as but not limited to a contact lens by printing.
Figure 6:
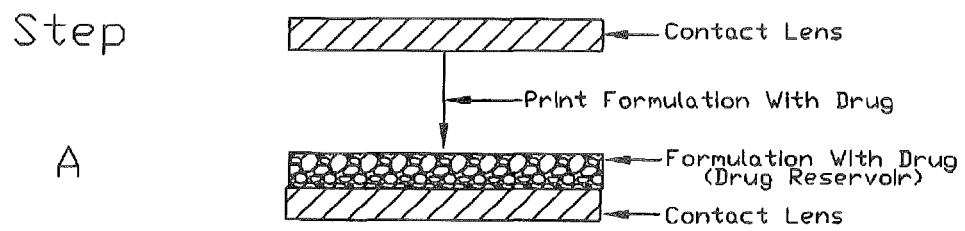
FIG. 6 depicts one aspect of the invention where the drug is one of the ingredients of printable formulation that also includes monomers with derivatized oligomers.

The drug reservoir layer serves to store a drug for later release from the coating. The drug reservoir layer is preferably porous or otherwise is able to contain a drug for this purpose. In one aspect of the present invention, the drug reservoir layer is solid or semi-solid, such as a gel or sol, which can reversibly entrap a drug for later release. The drug reservoir layer can be provided first without a drug and the drug added at a later step (see, FIG. 5). In the alternative the drug reservoir layer can be provided with a drug in one step (see, FIG. 6). The drug reservoir layer is preferably made using printing technology. The choice of polymer depends on several factors, including, for example, the printing technology to be used to print the drug reservoir layer.

The drug reservoir layer can include a polymer with the characteristics stated above. Preferable polymers include, but are not limited to, polyHEMA, polyGMA, polyvinylalcohol, polyDMA, PMMA (polymethylacrylicacid), polycarbonate, PVP (polyvinylpyrolidone), siloxane, and the like. Depending on the polymer and the printing technology chosen, the polymer can be provided in a monomer state and later polymerized, or in the alternative, provided in a partially polymerized state.

The drug reservoir layer can also include a partially polymerized polymer with the characteristics stated above and can be any as appropriate. Preferable polymers include, but are not limited to polyHEMA, polyGMA, polyvinylalcohol, polyDMA, PMMA (polymethylacrylicacid), polycarbonate, PVP (polyvinylpyrolidone), siloxane, and the like. Depending on the partially polymerized polymer and the printing technology chosen, the partially polymerized polymer can be provided in a monomer state and later partially polymerized, or in the alternative, provided in a partially polymerized state.

The drug reservoir layer can include a polymer matrix with the characteristics stated above and can be any as appropriate. Preferable polymer matrix include, but are not limited to, proteins, nucleic acids, and carbohydrates. Depending on the polymer and the printing technology chosen, the polymer matrix can be provided in a monomer state and later polymerized, or in the alternative, provided in a polymerized state.

In addition, still other materials can be used for the drug reservoir layer, such as, but not limited to silicone, ceramic, glass, carbon (inclusive of nanotubles and graphite) and fabric. The silicone, ceramic, glass, carbon and fabric can be any appropriate and as are realized in the art and the choice generally relates, as with other materials used in the drug reservoir layer, to they physical characteristics such as the ability to accept and retain a drug for later release and the printing technology chosen to print the drug reservoir layer.

Preferable materials for the drug reservoir layer include derivatized oligomers. Preferable derivatized oligomers include, but are not limited to HEMA (mydroxyethylmethylacrylates), DMA (dimethylacrylamides), GMA (glycidolmethylacylates), PVA (polyvinlyalcohols), silicone or siloxane. As with other materials used, the choice of derivatized oligomers depends on the physical characteristics of the material and the printing technology used to make the drug reservoir layer.

If the material used for the drug reservoir layer need to be polymerized and cured, then a polymerization initiator or curing initiator needs to be used. The requirement for a polymerization initiator or curing initiator depends on the particular type of polymer/monomer being utilized and the choice is established in the technology. Preferable polymerization initiator or curing initiators include, but are not limited to at least one of UV cure, thermal cure, room temperature cure, simultaneous printing and UV curing or e-beam.

As set forth in the figures, the drug reservoir layer can release a drug in one or more directions. For example, turning to a contact lens, the drug receiving layer can release drug towards the cornea or towards the eyelid when the contact lens is engaged with the eye. The use of barrier layers, or lack thereof, allows for the design of structures that allow drug to be released in one or both directions.

The material used for the drug receiving layer can be bonded to, permanently bonded to, or not bonded to the surface. Certain materials that can be used for the drug reservoir layer inherently bond or do not bond to a surface, depending on the nature of the surface. As discussed previously, the surface can be modified, such as through chemical medication or other methods or techniques, to allow the drug reservoir layer to chemically bond or react with the drug receiving layer components.

Drug Receiving Layer

The manufacture of the drug reservoir layer can include the use of a drug receiving layer. In this instance, a drug receiving layer is applied to the surface by an appropriate means or method, such as printing. The drug receiving layer could include or not include a drug at this juncture in time. The drug receiving layer has physical and chemical characteristics to allow the efficient and localized acceptance of a drug applied thereto using appropriate methods, preferably printing. Once the drug receiving layer is applied to the surface, then a drug, or an additional drug, is applied thereto to entrap the drug or additional drug therein for later release.

The drug receiving layer can be of any appropriate material with the appropriate physical and chemical characteristics to obtain a structure with the desired characteristics discussed herein. The drug receiving layer can be a chemical. Preferred materials for the drug receiving layer include, but are not limited to, a highly absorbent polymer such as, but not limited to, a polyvinlylpyrrolidone homopolymer, a polyvinylpyrrolidone copolymer, a polyacrylamide homopolymer, a polyacrylamide copolymer, a polyacrylate homopolymer, a polyacrylate copolymer, a proteinaceous material, a carbohydrate, or a combination thereof.

As there may be other layers applied to the surface prior to the drug receiving layer, the drug receiving layer can be applied to such prior layers using appropriate methods. As with other layers of the coating of the present invention, the drug receiving layer can be provided by any appropriate method, preferably by printing technology.

Where the drug receiving layer includes a polymer, then the drug receiving layer can include a bonding agent or crosslinking agent in order to aid in entrapping or otherwise immobilizing a drug for later release from the drug reservoir layer. Preferable bonding agents include, but are not limited to methylacrylic acid, titanates, and silanes. Preferable crosslinking agents include, but are not limited to HDI, and devivitized oligomers of HEMA, GMA, DMA and PVA, Polyfunctional Aziridine, and multifunctional carbodimide.

In one preferred aspect of the present invention, the drug receiving layer includes a highly absorbent polymer. Preferred highly absorbent polymers include, but are not limited to a polyvinylpyrrolidine homopolymer, a polyvinylpyrrolidone copolymer, a polyacrylamide homopolymer, a polyacrylamide copolymer, a polyacrylate homopolymer, a polyacrylate copolymer, a proteinaceous material, a carbohydrate, or a combination thereof.

The preferred method of application of a drug receiving layer of the present invention is printing technologies and coating technologies. Preferable methods of printing include, but are not limited to direct coating, application of droplets or microdroplets, ink jet printing, soaking, impregnation, spin coating, drip coating, screen coating, silk screen coating, or pad printing such as those methods are known in the art.

Drug

The drug provided in the drug reservoir agent is a matter of choice to one skilled in the appropriate arts depending on the disease, disorder or condition to be treated or prevented, along with the location of the article of manufacture on or with the subject and the nature of the medical device used. For example, drug for the treatment or prevention of glaucoma would be provided with a contact lens, whereas a drug for the treatment or prevention of restinosis would be provided with a stent.

The drug released from the article of manufacture should be of the appropriate amount, duration and dosing in order to be an effective amount to prevent or treat at least one disease, disorder or condition. The amount, duration and dosing of a drug to a particular location for such treatment or prevention is available to one skilled in the art. The present invention allows localized and controlled dosing in terms of the amount and duration of the dose and can allow for the continuous or intermittent release of drug for a regime of drug delivery.

One preferable aspect of the present invention is the delivery of a drug to the eye to treat or prevent or treat diseases, conditions or disorders of the eye. There are drugs known to treat or prevent a variety of diseases and conditions with appropriate regimes of dose, time course of administration, and route of administration. The present invention allows for varying the regime of dose and time course and provides a highly localized route of administration as well. Preferred drugs that are antibiotics useful for treatment of eye infections include, but are not limited to, gentamicin, tobramycin, erythromycin, polytrim, cirproflizacin, viamox, and xymar. Preferred drugs that are used to treat glaucoma include, but are not limited to, timolol, alphagan, axopt, cosopt, lumigan, travatan, xalatan, and combigan. Preferred drugs that are anti-inflammatory that are used to treat diseases, disorders and conditions of the eye include, but are not limited to, perdforte, lotemax, fluromethlone, nevanac, acular and xibrom. Other drugs known in the art to treat or prevent diseases, conditions or disorders of the eye include, but are not limited to pilocarpine, dexamethasone, pilocarpine nitrate, tropicamide, timolol, timolol nitrate, timolol maleate, methyl prednisolone, flurbiprofen, penillin G, gentamicin, ciprofloxacin, tobramycin, sulphacetaminde sodium, indomethacin, hydrocortisone, indomethacin, pilocarpine hydrochloride, ciprofloxacin hydrochloride, insulin, indomethacin, and ketorolac tromethamine, either alone or in combination. (See, for example, Yasmin Sultana, Rahul Jain, Rahul Rathod, Asgar Ali, M.Aqil, Department of Pharmaceutics, Faculty of Pharmacy, Hamdard University, New Delhi 110062, INDIA."Advances in Ophthalmic Drug Delivery Systems: Part I" By—Apr. 12, 2005, in Latest Reviews Vol. 3 Issue 2, 2005, www.pharmmainfo.net/reviews/advances-opthalmic-drug-delivery-systems-part-i, and Yasmin Sultana, Rahul Jain, Rahul Rathod, Asgar Ali, M. Aqil, Department of Pharmaceutics, Faculty of Pharmacy, Hamdard University, New Delhi 110062, INDIA, "Advances in Ophthalmic Drug Delivery Systems: Part II" By Apr. 12, 2005, in Latest Reviews Vol. 3 Issue 2, 2005, www.pharmmainfo.net/reviews/advances-opthalmic-drug-delivery-systems-part-ii (Apr. 1, 2011) ("Sultana et al. Part II). Sultana et al, Part I and Sultana et al. Part II provide reviews and listings of drugs and combinations thereof to treat or prevent various diseases, conditions and disorders of the eye. The patent literature also provides for ocular drug delivery devices and strategies as provided by Sultana et al. Part I and Sultana et al. Part II. See, for example U.S. Pat. Nos. and US published patent application numbers: 4,925,581; 5,227,372; 5,296,228; 5,480,914; 5,578,638; 5,705,194; 5,888,493; 6,242,442; 6,297,240; 6,316,441; 6,410,045; 6,416,740; 20020071874; 20020197300; 20030017199; 5,837,226; 6,017,875; 6,154,671; 6,217,896; 6,319,240; 6,335,335; 6,410,045; 6,539,251; 6,579,519; 20020026176; 20030147849; 20020064513; 20020114778; 20020119941; 20020197300; 20030175324; 20030185892; 20030191426; and 20040037889.

In one aspect the present invention, the drug is provided in the drug reservoir layer and released from the drug receiving either alone or in combination with other ingredients. Alternatively, the drug can be provided in the drug reservoir layer with such other ingredients and then released from the drug reservoir layer without such other ingredients. In a preferred aspect of the present invention the drug is provided at least in part as a sole active ingredient without any other ingredient association that can alter the activity or deliverability of the at least one drug. That is to say that the drug is provided or released alone and free of other ingredients, such as but not limited to those used for encapsulation, micro-encapsulation or emulsification of a drug.

The drug can be provided or released from the drug receiving layer and coating of the present invention in an encapsulated form. Encapsulation of drugs is known in the art, such as and is within the skill of the ordinary artisan. Preferred encapsulation materials include, but are not limited to: biodegradable polycyanoacrylate, biodegradable poly(alkylcyanoacrylates), biodegradable calcium phosphate, legumin, polysaccharides drafted with polyesters (amphyphilic copolymers), poly(methylidene malonate), gelatin, poly(E-caprolactone), sodium alginate, agarose hydrogel, PMMA, biotinylated poly(ethylene glycol) conjugated with lactobionic acid, poly(vinyl alcohol) hydrogel, biotinylated pullulan acetate, dib toe copolymers and mixtures thereof. Wherein the polycyanoacrylates are preferably, but not limited to: polybutylcyanoacrylate, polyhexyl-cyanoacrylate, polyethyl-cyano-acrylate, polyisobutyl-cyanoacrylate and mixtures thereof.

The drug can be provided or released from the drug receiving layer and coating of the present invention in a micro-encapsulated form. Micro-encapsulation of drugs is known in the art, such as "Microencapsulation Techniques, Factors Influencing Encapsulation Efficiency: A Review" Jyothi et.al Journal of Microencapsulation, Informa Health Care, Volume 27, Issue 3, P. 187-197, and is within the skill of the ordinary artisan.

The drug can be provided or released from the drug receiving layer and coating of the present invention in a nanoencapsulated with an encapsulation material in nanoparticles. Nanoencapsulation of drugs is known in the art, and is within the skill of the ordinary artisan. Non-limiting examples of nanoencapsulation materials include: chitosan nanparticles, human serum albumin nanoparticles; silica nano spheres, PEG'ylated core-shell nanoparticles, biodegradable PGGA(poly(D,L-lactide-co-glycolide) particles, PLA (poly lactic acid), PGA, PLG (poly-(D,L-glycolide) polymeric nanoparticles, biocompatible gliadin nanoparticles, low pH sensitive PEG stabilized plasmid-lipid nanoparticles, tocopherol derivatives stabilized nano-sized emulsion particles, PLA-PEG nanoparticles, nanoparticles composed of hydrophilic proteins coupled with apolipoprotein E, biodegradable poly(vesiln-caprolactone) nanoparticles, biotinylated poly(ethylene glycol) conjugated with lactobionic acid, earboxylmethyl dextran magnetic nanoparticles and mixtures thereof.

The drug can be provided or released from the drug receiving layer and coating of the present invention in an emulsion, water-in-oil emulsion, an oil-in-water emulsion, or a liposome. Emulsions, water-in-oil emulsions, oil-in-water emulsions and liposomes including drugs is known in the art, such as U.S. Pat. No. 7,638,137 B2, and is within the skill of the ordinary artisan.

The drug of the present invention can take any appropriate form, such as a small molecule or a biologic or biologic mimic as those terms are known in the art. As stated previously, a wide variety of drugs in many forms are known for the treatment or prevention of a disease, disorder or condition. The present invention is not limited to any particular type or classification of drug. The structures of the coating of the present invention can be tailored for the storage and release of any appropriate drug. For example, the porosity of a drug reservoir layer would tend to be greater for a larger molecule, and likewise less so for a small molecule. By way of example, a small molecule would include hormones for hormone replacement therapy or nucleoside analogues as anti-viral agents. Biological drugs and related biological mimics, by way of example, would include the general classifications of enzymes, transport proteins, structural proteins, storage proteins, hormone proteins, receptor proteins, contractile proteins, defensive proteins, cytokines, clotting factors and vaccines. An example of a preferred proteins include, but are not limited to, insulin for the treatment of diabetes and antibodies and monoclonal antibodies for the treatment of infection or for targeted delivery of associated drugs.

In essence, virtually any drug can be useful in the present invention and an enumerated listing is beyond the scope of this document. As way of example, the following is a non-limited and non-exhaustive list of general classifications of drugs useful in the present invention: an anti-inflammatory, an anti-allergy, and antibiotic, a drug for the treatment of glaucoma, a drug for the treatment of macular degeneration, an ophthalmic drug, a hydrophilic drug, a hydrophobic drug, an anti-parasitic drug, a steroid, an antibiotic and a medicament for the treatment of dry eye and a medicament for treatment of eye discomfort.

Barrier Layer

The coating of the present invention can also include a barrier layer. In one aspect of the invention, the barrier layer is applied to the top of the drug reservoir layer and provides structure to the coating layer to modulate release of the drug from the coating and the coating. The barrier layer in this aspect of the invention can provide drug release modulating structures such as, but not limited to capillary structures. Multiple layers of barrier layers can be used as well to further modulate the release of drug from the drug reservoir layer and the coating layer. In another aspect of the invention, a barrier layer can be provided below the drug reservoir layer so as to prevent or diminish the migration of a drug in one direction while allowing the drug to migrate in another direction. Unlike the drug reservoir layer, the barrier layer does not substantially sequester a drug or allow a drug to pass through that structure, but rather modulates the flow of drug from the drug reservoir layer and the coating layer. The barrier layer can be provided within the coating by any appropriate means, preferably but not limited to printing technology.

The barrier layer can include a polymer with the characteristics stated above. Preferable polymers include, but are not limited to silicone, polyhydroxyethylmethylacrylates (polyhema, PVA, poly-n-vinyl pyrolidone, and polycarbonates). Depending on the polymer and the printing technology chosen, the polymer can be provided in a monomer state and later polymerized, or in the alternative, provided in a polymerized state.

The barrier layer can also include a partially polymerized polymer with the characteristics stated above and can be any as appropriate. Preferable polymers include, but are not limited to silicone, polyhydroxy ethylmethylacrylates (polyhema, PVA, and polycarbonates). Depending on the partially polymerized polymer and the printing technology chosen, the partially polymerized polymer can be provided in a monomer state and later partially polymerized, or in the alternative, provided in a partially polymerized state.

The barrier layer can include a polymer matrix with the characteristics stated above and can be any as appropriate. Preferable polymer matrix include, but are not limited to, proteins, nucleic acids, and carbohydrates silicone, polyhema, and polycarbonates). Depending on the polymer and the printing technology chosen, the polymer matrix can be provided in a monomer state and later polymerized, or in the alternative, provided in a polymerized state.

In addition, still other materials can be used for the barrier, such as, but not limited to silicone, ceramic, glass, carbon (inclusive of nanotubles and graphite) and fabric. The silicone, ceramic, glass, carbon and fabric can be any appropriate and as are realized in the art and the choice generally relates, as with other materials used in the barrier layer, to their physical characteristics such as the ability to generally accept and not retain a drug for later release and compatible with the printing technology chosen to print the barrier layer, can make permanent bond or dissolve in solvent or washable with solvent rinse.

Preferable materials for the barrier layer include derivatized oligomers. Preferable derivatized oligomers include, but are not limited to HEMA, DMA, GMA, PVA, silicone or siloxane. As with other materials used, the choice of derivatized oligomers depends on the physical characteristics of the material and the printing technology used to make the drug barrier layer.

If the material used for the barrier layer need to be polymerized and cured, then a polymerization initiator or curing initiator needs to be used. The requirement for a polymerization initiator or curing initiator depends on the particular type of polymer/monomer being utilized and the choice is established in the technology. Preferable polymerization initiator or curing initiators include, but are not limited to at least one of UV cure, thermal cure, room temperature cure, simultaneous printing and UV curing or e-beam.

In one preferred aspect of the present invention, the barrier layer includes capillary structures in order to modulate the release or flow of drug from the drug reservoir layer and the coating layer in general. These capillary structures are of a shape, size, orientation and spacing in order to allow capillary action to modulate the flow of drug from the drug reservoir layer and out of the coating layer.

The Lucas-Washburn equation that predicts the rise of the fluid meniscus, H(t), in the capillary with time t is given as:

$$H(t) = [(sR \cos \emptyset/2n)^{1/2} t^{1/2}]$$

Where:
s=fluid surface tension
n=fluid shear viscosity
R=pore radius
Ø=contact angle between meniscus and wall
(Ref. D. I. Dimitrovl, A. Milchev1,2, and K. Binder1
1Institute für Physik, Johannes Gutenberg Universität Mainz, Staudinger Weg 7, 55099 Mainz, Germany
2Institute for Chemical Physics, Bulgarian Academy of Sciences, 1113 Sofia, Bulgaria, Received 30 Mar. 2007; published 31 Jul. 2007)

One can use this equation to determine the drug release rate $R_{capillary}$ for a capillary of given height, diameter, contact angle, viscosity and surface tension. The diameter and height of capillaries are at nano level, for example, they may be less than about 5 nanometers to about 50,000 nanometers.

Printing

A wide variety of printing technologies are applicable to providing the various layers of the coating of the present invention. The choice of which printing technology to use is a matter of choice for the skilled artisan based on the particular size, shape, thickness and other characteristics of the layer being provided. In addition, as some of the layers are printed in liquid or semi-solid form and then transformed into a solid or semi-solid form by, for example but not limited to polymerization or partial polymerization, the characteristics of the printing liquid or semi-solid is to be taken into account. As a preferred aspect of the present invention, the compositions of Doshi et al., published U.S. application No. 2008/0062381A1, published Mar. 13, 2008, are applicable, particularly when the pigment is optionally present in such formulations, and at least one drug is optionally provided in such formulations.

Preferred printing methods are digital in nature, such as those described by Doshi et al. (U.S. 2008/0062381A1) which is incorporated by reference herein in its entirety, such that they allow for a relatively precise method and means to provide a high quality and well defined print product. As the method and associated device are digital in nature, the printing process is adaptable for computer control and product design. Preferred digital printing methods and structures are discussed herein. As a non-limiting introduction to digital printing methods and devices, the following digital printing methods are preferred: ink jet printing, three dimensional printing (3D printing), piezo printing, thermal printing, laser printing MEMS printing (Micromachined Electro-Mechanical System) wherein the printing head or related or associated structures are rotatable or non-rotatable. Generally, but not exclusively, a printing solution of the present invention replaces the ink solution of existing and commercially available printing devices, in particular within the printing cartridge.

Likewise, preferred printing methods include pad printing as these methods are known in the art, including but not limited to pad transfer printing. Pad printing is not as exact as digital printing, but is a preferred method of printing for the present invention. Pad printing is known in the art for printing of images of the iris of the eye on contact lenses (see, for example, U.S. Pat. Nos. 5,302,978, 5,414, 477, and 4,668,240).

Ink jet printing is known in the art and can take various forms and associated structures as are discussed herein. Generally, ink jet printing refers to printing devices and methods that utilize highly precise printing methods and structures that allow for the production of high quality and precise structures. Generally, available ink jet printing devices and structures can be utilized with minimal modification, with the ink solutions normally present in the ink jet cartridge or reservoir is replaced with a solution that includes a polymerizable monomer and associated polymerization initiators as needed. The polymerizable monomer can be polymerized at will and at a rapid rate after being dispensed from the ink jet printing structure.

Three dimensional printing is based primarily, but not exclusively, on ink jet printing technologies. These methods and devices allow for the generation of one-off or multiple copies of structures. Generally, a polymerizable solutions is placed within the printing device and is dispensed under computer control and polymerized in repeated printing cycles or steps to generate a three dimensional structure. Examples of available and preferred 3D printing devices and related structures and cartridges include, but are not limited to those disclosed herein and otherwise known in the art or later developed.

Piezo printing is a subtype of ink jet printing that is a preferable printing method of the present invention. Examples of available and preferred piezo printing devices and related structures and cartridges include, but are not limited to those disclosed herein and otherwise known in the art or later developed.

Thermal printing is a subtype of ink jet printing that is a preferable printing method of the present invention. Examples of thermal printing devices and related structures and cartridges include, but are not limited to those disclosed herein and otherwise known in the art or later developed.

Laser printing is a subtype of ink jet printing that is a preferable printing method of the present invention. Examples of laser printing devices and related structures and cartridges include, but are not limited to those disclosed herein and otherwise known in the art or later developed.

Optionally, an ink jet printing device can include a rotating printer head that can allow for enhanced printing on curved surfaces.

Another preferred printing method is MEMS printing, wherein MEMS stands for Micromachined electromechanical system and is based on technologies that allow for the printing of integrated circuit boards, but are applicable to the production of very small structures that have functionality. Examples of structures having functionality made by MEMS printing include mechanical gears and other mechanical devices, lab on a chip structures for the performance of laboratory procedures including chemical reactions and diagnostic procedures Modulation of Release of Drug The combination of the components of the coating of the present invention, in particular the at least one drug reservoir layer that includes at least one drug and the at least one barrier layer, optionally with structures, such as but not limited to capillary structures, allows for the controlled release of the at least one drug from the coating. The coating structure allows for the production of a coating layer that can particularly tailor the release of the at least one drug from the coating layer for desirable characteristics, such as, but not limited to, dose, regime, time course of delivery and route of administration. As the article of manufacture can be localized to a particular locus on a subject, the drug can be delivered with particular focus with a particular regime, which can allow for less drug being administered to a subject if it were otherwise administered in a more systematic route of administration. The particular physical chemistry phenomenon associated with the release of the drug from the coating layer are discussed herein, but the listing is not to be considered limiting.

In one aspect of the invention, the release of the at least one drug from the coating layer can be modulated by diffusion, first out of the drug reservoir layer and then through the barrier layer, if present. Determination of the effect of diffusion on the migration of a chemical entity through a substrate or structures that can be a part of the coating layer can be made using established methods, formulas and through routine experimentation.

Figure 4:
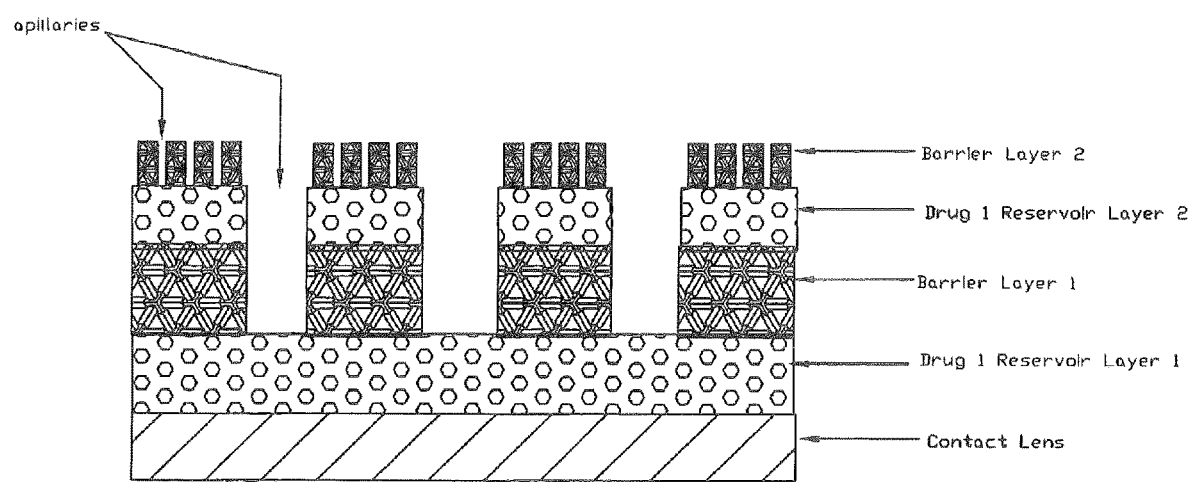
FIG. 4 depicts a further extension of capillaries and barrier layers to accommodate one or more drugs or to obtain a desirable drug release rate. The drug reservoir layer can be built on the surface of the medical device such as but not limited to a contact lens.

In another aspect of the invention, the release of the at least one drug from the coating layer can be modulated by diffusion, first out of the drug reservoir layer and then through the barrier layer which can include structures, such as capillary structures (see, FIG. 4). Determination of the effect of capillary action on the migration of a chemical entity through a capillary structure present in the coating layer of the present invention, in particular the barrier layer, can be made using established methods, formulas and through routine experimentation.

In another aspect of the invention, the release of the at least one drug from the coating layer can be modulated by mass action, first out of the drug reservoir layer and then through the barrier layer which can include structures, such as capillary structures. Determination of the effect of mass action on the migration of a chemical entity through a coating layer of the present invention, can be made using established methods, formulas and through routine experimentation.

In yet another aspect of the invention, the release of the at least one drug from the coating layer can be modulated by a concentration gradient of the at least one drug, first out of the drug reservoir layer and then through the barrier layer which can include structures, such as capillary structures. Determination of the effect of a chemical gradient on the migration of a chemical entity through a coating layer of the present invention, can be made using established methods, formulas and through routine experimentation.

In yet another aspect of the invention, the release of the at least one drug from the coating layer can be modulated by the solubility of the at least one drug in an environment, first out of the drug reservoir layer and then through the barrier layer which can include structures, such as capillary structures. Determination of the effect of a solubility on the migration of a chemical entity through a coating layer of the present invention, can be made using established methods, formulas and through routine experimentation.

In yet another aspect of the invention, the release of the at least one drug from the coating layer can be modulated by the temperature at which the article of manufacture is held (either at storage temperature or during use) of the at least one drug, first out of the drug reservoir layer and then through the barrier layer which can include structures, such as capillary structures. Determination of the effect of temperature on the migration of a chemical entity through a coating layer of the present invention, can be made using established methods, formulas and through routine experimentation.

In yet another aspect of the invention, the release of the at least one drug from the coating layer can be modulated by the molecular weight of the at least one drug, first out of the drug reservoir layer and then through the barrier layer which can include structures, such as capillary structures. Determination of the effect of molecular weight on the migration of a chemical entity through a coating layer of the present invention, can be made using established methods, formulas and through routine experimentation.

In yet another aspect of the invention, the release of the at least one drug from the coating layer can be modulated by a concentration gradient of the at least one drug, first out of the drug reservoir layer and then through the barrier layer which can include structures, such as capillary structures. Determination of the effect of the migration of a chemical gradient on a chemical entity through a coating layer of the present invention, can be made using established methods, formulas and through routine experimentation.

In further aspect of the invention, the release of the at least one drug from the coating layer can be modulated by the thickness of the coating layer, and the components thereof, namely the drug reservoir layer and the barrier layer, if present, and ancillary structures, such a capillary structures, if present. Determination of the effect of the thickness of the coating and the components thereof on the migration of a chemical entity through a coating layer of the present invention, can be made using established methods, formulas and through routine experimentation.

In a still further aspect of the invention, the release of the at least one drug from the coating layer can be modulated by the porosity of the coating layer, and the components thereof, namely the drug reservoir layer and the barrier layer, if present, and ancillary structures, such a capillary structures, if present. Determination of the effect of the porosity of the coating and the components thereof on the migration of a chemical entity through a coating layer of the present invention, can be made using established methods, formulas and through routine experimentation.

In a still further aspect of the invention, the release of the at least one drug from the coating layer can be modulated by the pore size of the coating layer, and the components thereof, namely the drug reservoir layer and the barrier layer, if present, and ancillary structures, such a capillary structures, if present. Determination of the effect of the pore size of the coating layer and the components thereof on the migration of a chemical entity through a coating layer of the present invention, can be made using established methods, formulas and through routine experimentation.

In a still further aspect of the invention, the release of the at least one drug from the coating layer can be modulated by the molecular exclusion size of the coating layer, and the components thereof, namely the drug reservoir layer and the barrier layer, if present, and ancillary structures, such a capillary structures, if present. Determination of the effect of the molecular exclusion size of the coating and the components thereof on the migration of a chemical entity through a coating layer of the present invention, can be made using established methods, formulas and through routine experimentation.

In another aspect of the invention, the release of the at least one drug from the coating layer can be modulated by the water content of the coating layer, and the components thereof, namely the drug reservoir layer and the barrier layer, if present, and ancillary structures, such a capillary structures, if present. Determination of the effect of the water content of the coating and the components thereof on the migration of a chemical entity through a coating layer of the present invention, can be made using established methods, formulas and through routine experimentation.

In yet another aspect of the invention, the release of the at least one drug from the coating layer can be modulated by the concentration of the drug in the coating layer, and the components thereof, namely the drug reservoir layer and the barrier layer, if present, and ancillary structures, such a capillary structures, if present. Determination of the effect of the concentration of the drug in the coating and the components thereof on the migration of a chemical entity through a coating layer of the present invention, can be made using established methods, formulas and through routine experimentation.

In a further aspect of the invention, the release of the at least one drug from the coating layer can be modulated by the concentration of the drug in the coating layer, and the components thereof, namely the drug reservoir layer and the barrier layer, if present, and ancillary structures, such a capillary structures, if present. Determination of the effect of the concentration of the drug in the coating and the components thereof on the migration of a chemical entity through a coating layer of the present invention, can be made using established methods, formulas and through routine experimentation.

In a still further aspect of the invention, the release of the at least one drug from the coating layer can be modulated by the packaging environment of the coating layer (such as the concentration of drug in the packaging solution, if present), and the components thereof, namely the drug reservoir layer and the barrier layer, if present, and ancillary structures, such a capillary structures, if present. Determination of the effect of the packaging environment of the coating and the components thereof on the migration of a chemical entity through a coating layer of the present invention, can be made using established methods, formulas and through routine experimentation.

In one aspect of the invention, the drug can exhibit sustained release over time from the coating layer. This can be achieved by first establishing the relationship of release rate of a given drug for a given material of barrier layer in terms of thickness variation, drug solubility, concentration. In another aspect of the invention, the drug can exhibit intermittent release over time from the coating layer.

In yet another aspect of the invention, more than one drug can be released from the coating layer of the present invention. This aspect of the invention is depicted in FIG. 8 wherein different areas of the coating layer have different drugs provided in the drug reservoir layer. In the alternative, more than one drug can be provided in a single drug reservoir layer.

Contact Lens

In one preferred aspect of the present invention, the medical device includes a contact lens. Contact lenses that include a drug, on the surface of the contact lens or within the contact lens are known in the art. However, these contact lenses do not provide the structures of the present invention, such as the at least one coating that includes at least one drug reservoir layer that can include at least one drug, and at least one barrier layer that can include structures, wherein the release of the at least one drug from the at least one coating layer is modulated by A variety of materials are known in the art for making contact lenses and are useful in the present invention. Preferred materials include, but are not limited to, acrylics, silicones, polyvinylalcohols, and combinations thereof.

There are a variety of general types of contact lenses known in the art and are useful in the present invention. Preferred general types of contact lenses include, but are not limited to hybrid lenses, hydrophilic lenses and hydrophilic lenses.

In addition, there are other general types of contact lenses known in the art and are useful in the present invention. These lenses include, but are not limited to spherical lenses, toric lenses, multifocal lenses, tinted lenses, corrective optical power lenses and lenses without corrective optical power.

There are a variety of methods used to make lenses that are useful in the present invention. Preferred methods of making, at least in part or in combination, contact lenses include, but are not limited to, lathing, cast molding, spin casting and ink jet printing.

Once a contact lens is manufactures, a variety of secondary or finishing operations can be utilized and are useful in the present invention. Preferred secondary or finishing operations include, but are not limited to edging, polishing, tinting, hydration, extraction, and sterilization.

In one aspect of the present invention, the at least one drug in an at least one coating layer can be provided on the surface of a contact lens. In another aspect of the present invention, the at least one drug in at least one coating layer can be provided within a contact lens. In another aspect of the present invention, the at least one drug can be provided inside a contact lens without the structures in an at least one coating layer in combination with at least one drug in at least one coating layer on the surface of a lens. In yet another aspect of the present invention, the at least one coating layer with at least one drug can be provided both on the surface of the lens and inside the lens.

In some cases, drugs provided within the at least one coating can have optical properties that can interfere with the optical function of the contact lens, such as drugs having coloring or opaqueness. Preferred drugs for use in the present invention do not have such optical properties, but that need not be the case as drugs having such optical properties are useful in the present invention.

In another aspect of the present invention, the one or more coatings can optionally dispersed therein nanoparticles having a particles size less than about 50 nm, a nanoencapsulated ophthalmic drug from which the ophthalmic drug is able to diffuse into and migration through the contact lens and into the post-lens tear film or towards the eyelid when the contact lens is placed on the eye, the nanoparticles being disperse within the contact lens or on at least one surface of the contact lens in an amount such that the lens optionally remains substantially optically transparent (see, for example, U.S. Pat. No. 7,638,137B2 to Chauhan et al., issued Dec. 29, 2009).

In another aspect of the present invention, the one or more coatings can optionally dispersed therein nanoparticles having a particles size less than about 50 nm, a nanoencapsulated ophthalmic drug from which the ophthalmic drug is able to diffuse away from and migrate away from the contact lens and into the post-lens tear film or towards the eyelid when the contact lens is placed on the eye, the nanoparticles being disperse within the contact lens or on at least one surface of the contact lens in an amount such that the lens optionally remains substantially optically transparent (see, for example, U.S. Pat. No. 7,638,137B2 to Chauhan et al., issued Dec. 29, 2009).

In yet another aspect of the present invention, when the at least one drug is provided with or without a drug delivery compositions as described herein, the at least one drug as provided with or without a drug delivery compositions is substantially optically transparent. However, this need not be the case. In one aspect of the present invention, when the at least one drug as provided with or without a drug delivery composition is substantially optically transparent or is not substantially optically transparent, the optical characteristics of the at least one drug, or other structures of the at least one coating layer, can be masked with opaque material or tinting, such as color tinting as is known in the art.

Packaging

The article of manufacture of the present invention can be provided in a variety for forms and packaging formats and solutions as present. Many of these packaging form and formats are established packaging formats, whereas others are unique to the present invention.

The article of manufacture of the present invention can be provided in a packaging in a dry state, preferably in a dehydrated state or a lyophilized state using methods know in the art. The article of manufacture of the present invention can also be provided in a packaging in a wet state, that is to say provided in an appropriate solution and, as appropriate, in a hydrated state.

The format of the packaging can be any as is appropriate. For example, the article of manufacture can be provided in packaging that is appropriate and normal for the article of manufacture, such as vials, other containers such as boxes or plastic containers, or in vials. Vials and blister packaging are preferable, but not necessary, for example, for contact lenses.

The solution present, if any, in a packaging format, in particular for a wet state packaging format can include the at least one drug present in the at least one coating layer, a different drug that that provided in the coating layer, or a combination thereof.

In one instance, the concentration of the drug in a packaging solution is less than the concentration of the drug in the coating layer. In that case, it is likely that the drug in the coating layer may migrate from the coating layer into the packaging layer and eventually reach a steady state equilibrium state, but that not be the case.

In another instance, the concentration of the drug in a packaging solution is equal to the concentration of the drug in the coating layer. In that case, it is likely that the drug in the packaging solution will be in steady state with the drug in the coating layer, but that need not be the case.

In the alternative, the concentration of the drug in the packaging solution is greater than the concentration of the drug in the coating layer. In that case, it is likely that the drug in the packaging solution would migrate into the coating layer and eventually reach a steady state equilibrium state, but that need not be the case.

In yet another instance, a drug provided in the packaging layer that is not present in the coating layer may be present. In that case, it is likely that the drug in the packaging solution would migrate into the contact lens and eventually reach a steady state equilibrium state, but that need not be the case.

II Methods of Making Medical Devices Including a Medicament

The present invention also includes a method of making an article of manufacture, comprising: a) providing a medical device including at least one surface; b) depositing one or more coatings on at least a portion of the at least one surface, wherein the one or more coatings includes; 1) at least one drug reservoir layer deposited at least in part by printing on the at least one surface, wherein the at least one drug reservoir layer comprises at least one drug; and 2) at least one barrier layer deposited at least in part by printing on at least a portion the at least one drug reservoir layer, wherein the at least one barrier layer includes one or more structures. Particular examples of this aspect of the invention are presented diagrammatically in FIG. 1 (see in particular steps 1 to 4).

Figure 9:
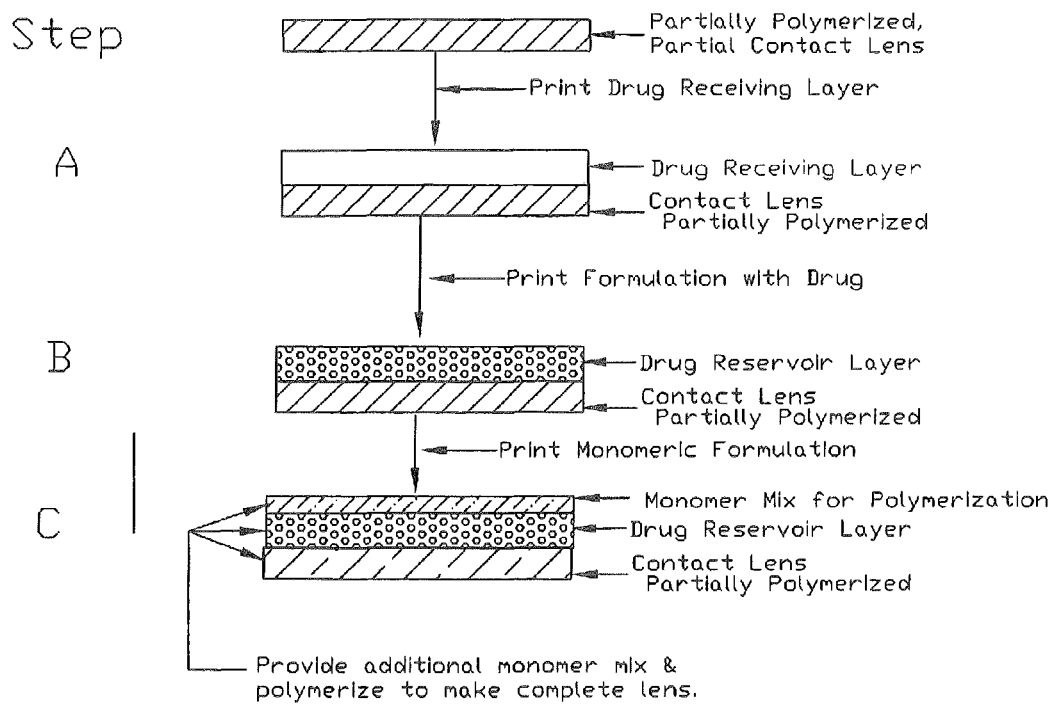
FIG. 9 also depicts one aspect of the invention where there is a uni-directional or near uni-directional release of a drug from the medical device such as but not limited to a contact lens utilizing a blocking layer that prevents release of a drug in one direction.

The present invention also includes a method of making an article of manufacture, including: a) providing a medical device including at least one surface; b) depositing one or more coatings on at least a portion of the at least one surface, wherein the one or more coatings comprises; 1) at least one barrier or blocking layer deposited at least in part by printing on said at least one surface; and 2) at least one drug reservoir layer deposited at least in part by printing on said at least barrier layer, wherein said at least one drug reservoir layer comprises at least one drug. Particular examples of this aspect of the invention are presented diagrammatically in FIG. 7 steps A through C. Also as shown in FIG. 9, a blocking layer can be deposited inside a partially polymerized contact lens to achieve a unidirectional drug release.

Having discussed the particular structures of the present invention, what they are made of, how they are preferably made, how they interact, how they are assembled and how they are chosen based on their physical and chemical nature, and the like, the discussion now turns to how the article of manufacture is made, with exemplary and preferred examples later provided in the examples section.

Medical Device

First, a medical device is chosen on which a coating is to be provided. Essentially any medical device can be used in the present invention. The choice of the medical device is one within the skill of the ordinary artisan and the state of the art provides vast literature on a wide variety of medical devices and where they are to be implanted and which drugs would be useful to be provided with a coating of the present invention to treat or prevent any number of diseases, conditions or disorders that a subject may suffer from.

The medical device can be implantable or non-implantable as those terms are known in the art and have been previously discussed. In one preferred aspect of the present invention, the medical device includes a cardiac stent or joint replacement apparatus, or other implantable medical device. In another preferred aspect of the present invention, the medical device includes a contact lens or skin patch drug delivery medical device, or other non-implantable medical device.

Surface

The medical device presents a surface upon which a coating of the present invention is to be made. The surface of the medical device chosen is usually an inherent property of the medical device, but that need not be the case. The surface can be modified by any number of methods or techniques and known in the art and discussed herein, including chemical modification or physical modification.

In certain preferred aspects of the present invention, as discussed herein, the surface presented for the application of a coating of the present invention includes, but is not limited to, at least one metal, at least one plastic, at least one polymer, at least one partially polymerized polymer, at least one polymer matrix, at least one protein matrix, at least one silicone, at least one ceramic, at least one glass, at least one carbon containing compound, at least one fabric, or a combination thereof.

In other preferred aspects of the present invention, as discussed herein, the surface presented for the application of a coating of the present invention can be modified by a variety of methods before a coating of the present invention is applied thereto. Preferred surface modification methods include but are not limited to one or more chemical processes or one or more physical processes. Preferred chemical processes include, but are not limited to, chemical coating, chemical cleaning, chemical texture modification, chemical or electrochemical activation or creation of reactive groups on or within said at least one surface, application of one or more chemicals to said at least one surface, and combinations thereof. Preferred physical processes include but are not limited to, etching, scoring, spraying of materials on the surface, sputtering of materials on the surface, corona treatment, and combinations thereof.

Drug Resevoir Layer

The coating of the present invention includes a drug reservoir layer, which includes at least one drug for later release into or onto a subject at the locus where the medical device is provided to a subject. The drug reservoir layer is preferably provided directly on at least a portion of the surface of a medical device as discussed herein and is the first component of the coating of the present invention. However, at least one barrier layer may be provided before an at least one drug reservoir layer in certain aspects of the invention where the direction of release of a drug from a coating of the present invention is desired, (see, FIG. 7) such as the case where a medical device presents multiple surfaces for release of a drug from a coating of the present invention, such as, for example, contact lenses where the drug can be released towards the eye, towards the eyelid, or both.

The drug reservoir layer can be made of any appropriate material or combination of materials, and the choice of material is generally within the skill of the art as influenced by a variety of factors, including but not limited to the printing method to be used to provide the drug reservoir layer, the size, thickness an shape of the drug receiving layer desired, the physical and chemical properties desired for the drug reservoir as influenced by the chemical and physical characteristics of the drug provided in the drug receiving layer such that the drug can be released at a desired rate, and the like.

Preferred materials for the drug receiving layer include, but are not limited to, at least one polymer, at least one partially polymerized polymer, at least one polymer matrix, at least one protein matrix, at least one silicone, at least one ceramic, at least one glass, at least one carbon containing compound, at least one fabric or a combination thereof. Other preferred materials include, but are not limited to, derivatized oligomers, such as but not limited to, HEMA, DMA, GMA, PVA, silicone and siloxane, or combinations thereof.

In certain aspects of the present invention, during the printing process used to make the drug reservoir layer, a non-polymerized or partially polymerized printing formulation, which can include at least one drug, is applied to the surface. In that instance, the non-polymerized or partially polymerized formulation is to be polymerized or otherwise cured to stabilize the drug receiving layer and, in certain aspects of the invention, serves to entrap or otherwise localize a drug in the drug reservoir layer for later release therefrom (see, FIG. 3). Preferred methods for polymerizing or curing a drug reservoir when needed or desirable include, but not limited to, at least one UV curing or polymerization, at least one thermal curing or polymerization, at least one room temperature curing or polymerization, at least one simultaneous printing and curing or polymerization, at least one e-beam curing or polymerization, or combinations thereof.

In certain aspects of the present invention, the drug reservoir layer is bonded to, permanently bonded to, or is not bonded to the surface. In this instance, reactive groups on the surface or the drug receiving layer may chemically or physically interact to form chemical bonds, such as covalent bonds, or physical bonds, such as short range interactions, such as but not limited to hydrogen bonds, van der Walls interactions, hydrophobic interactions, hydrophilic interactions, ionic interactions and the like. The formation of these chemical or physical interactions is dependent upon the chemical nature of the surface and the drug reservoir layer and can be determined by the artisan based on based on the state of the art.

In another aspect of the present invention, as discussed herein, the drug receiving layer can release a drug in one or more directions. In certain cases, the drug receiving layer, based on the nature of the medical device and surface, can release a drug only in one direction as the surface will prevent, or block, the release of drug in one direction as the drug is not able to substantially migrate into the surface or medical devices based on the material presented. As discussed herein, a blocking layer may be provided to prevent a drug from migrating in one direction. As discussed herein, a drug may be released in more than one direction, such as the case of contact lenses. Certain preferred configurations of this aspect of the invention are exemplified in FIG. 7.

Drug Receiving Layer

In one aspect of the present invention, the at least one drug reservoir includes an at least one drug receiving layer. In this aspect of the present invention, the drug receiving layer is printed on the surface, as the drug reservoir layer with at least one drug is as described herein, and an at least one drug is provided to said at least one drug receiving layer to form a drug reservoir layer. The drug is provided to the drug receiving layer my any appropriate method, such as by printing as described herein, but other methods of proving a drug to a drug receiving layer can be used, such as, but not limited to, soaking, dipping and spin coating. As with other layers of the coating of the present invention, the drug receiving layer can be made of any appropriate material or combination of materials, and the choice of material is generally within the skill of the art as influenced by a variety of factors, including but not limited to the printing method to be used to provide the drug receiving layer, the size, thickness an shape of the drug receiving layer desired, the physical and chemical properties desired for the drug reservoir as influenced by the chemical and physical characteristics of the drug provided in the drug receiving layer such that the drug can be released at a desired rate, and the like.

In one aspect of the present invention, the at least one drug reservoir layer includes a chemical coating applied to the surface. In the alternative, the at least one drug receiving layer is applied to another layer that has been previously applied to the surface, such as, but not limited to, a barrier layer to produce a coating layer that released a drug in a particular directions from the coating as described herein.

In another aspect of the present invention, the printing formulation used to print the drug receiving layer can include materials, such as chemicals, to allow for the polymerization or curing of the printed drug reservoir layer, and in certain instances, to allow for the tailoring of the physical characteristics of the drug receiving layer that affect the release of the drug therefrom as described herein, such as, but not limited to porosity, diffusion rate of a drug, and the like. The materials used to obtain these objectives include, but are not limited to bonding agents, cross linking agents, or a combination thereof. The use of bonding agents, cross linking agents, or combinations thereof to provide materials with desirable physical characteristics for the present invention are known in the art and are replete in the literature and adaptation to the present invention can be made using experimentation or mathematical modeling.

In one preferred aspect of the present invention, the drug receiving layer includes a highly absorbent polymer. Preferred highly absorbent polymers include, but are not limited to, at least one polyvinylpyrrolidine homopolymer, at least one polyvinylpyrrolidone copolymer, at least one polyacrylamide homopolymer, at least one polyacrylamide copolymer, at least one polyacrylate homopolymer, at least one polyacrylate copolymer, at least one proteinaceous material, at least one carbohydrate, or a combination thereof.

The drug reservoir can be applied to a surface or desired location using any appropriate method or means as described herein or as known in the art. Preferred methods or means include but are not limited to, direct coating, application of droplets or microdroplets, ink jet printing, soaking, impregnation, spin coating, drip coating, screen coating, silk screen coating, pad printing, or a combination thereof.

Drug

As discussed previously, the at least one drug reservoir layer of the at least one coating of the present invention includes at least one drug provided therein such that the at least one drug can be released from the at least one coating. In general, the choice of drugs to be provided in the coating layer are a matter of choice for the artisan, and there is a vast body of literature, both patent and not patent, available to the artisan to identify drugs that are effective to treat or prevent an disease, disorder or condition.

The drug can be provided in the coating in an amount sufficient such that when the drug is released from the coating it is provided in a therapeutically effective amount for the route of administration and location of the medical device of the present invention within or on the subject. The physical characteristics of the coating of the present invention as discussed herein, such as, but not limited to, pore size and water content, can be taken into account when considering what concentration of drug to be provided in the coating of the present invention such that the appropriate amount of drug is released from the coating of the present invention.

As discussed herein, a medical device of the present invention is provided within or on a subject such that the drug is released at a particular locus rather than systemically as with other drug delivery methods, such as through injection or oral administration. This allows for the drug to be delivered at a particular location and preferably at a lower or more precise dose than would otherwise be obtainable. The focused delivery of a drug by the medical device of the present invention also would reduce the instance of side effects of drugs that more systemic routs of administration would be characterized because the total body load of a drug in a subject would be greatly reduced compared to more systemic administration of a drug.

As discussed herein, the location of the drug delivery device is determinable by the nature of the medical device and the disease, disorder or condition to be prevented or treated. For example, implantable cardiac stents would be provided in blood vessels as is the normal course of treatment, and contact lenses would normally be provided on the eye, but this need not be the case.

The drug can be provided with the coating layer of the present invention, or released from the coating layer of the present invention in a variety of forms. In one aspect of the present invention, the drug is provided in the coating layer or released from the coating layer at least in part as a sole active ingredient without any other ingredient association that can alter the activity or deliverability of said at least one drug. That is to say, the drug is provided or released in a free state and not associated with other chemical entities, such as drug delivery chemical entities as described herein or known in the art.

In the alternative, the drug is provided in the coating layer or released from the coating layer at least in part in at least one encapsulated form, at least one micro-encapsulated form, at least one nano-encapsulated form, in at least one emulsion, in at least one water-in-oil emulsion, in at least one oil-in-water emulsion, or in at least one liposome, or a combination thereof, as described herein or as known in the art.

As described herein the drug provided in the coating layer or released therefrom can be virtually any drug, including but not limited to small molecule drugs or biological drugs as they are known in the art. There is a vast body of literature, both patent literature and non-patent literature for these types of drugs. A comprehensive list is beyond the scope of this document. Preferred classes of drugs are provided herein, and include, but are not limited to, at least one anti-inflammatory drug, at least one anti-allergy drug, at least one antibiotic drug, at least one drug for the treatment of glaucoma, at least one drug for the treatment of macular degeneration, at least one ophthalmic drug, at least one hydrophilic drug, at least one hydrophobic drug, at least one anti-parasitic drug, at least one steroid drug, at least one medicament for the treatment of dry eye and at least one medicament for treatment of eye discomfort, or a combination thereof.

In one preferred aspect of the present invention, the drug is provided in a coating layer or released from the coating layer in an at least one encapsulated form. Preferred encapsulation materials are discussed herein and are known in the art, and include, but are not limited to at least one biodegradable polycyanoacrylate, at least one biodegradable poly(alkylcyanoacrylates), at least one biodegradable calcium phosphate, at least one legumin, at least one polysaccharides drafted with polyesters (amphyphilic copolymers), at least one poly(methylidene malonate), at least one gelatin, at least one poly(E-caprolactone), at least one sodium alginate, at least one agarose hydrogel, at least one PMMA, at least one biotinylated poly(ethylene glycol) conjugated with lactobionic acid, at least one poly(vinyl alcohol) hydrogel, at least one biotinylated pullulan acetate, at least one dibloc copolymers and combinations thereof.

In another preferred aspect of the present invention, the polycyanoacrulate are those disclosed herein or known in the art, including but not limited to, at least one polybutylcyanoacrylate, at least one polyhexylcyanoacrylate, at least one polyethyl-cyano-acrylate, at least one polyisobutylcyanoacrylate and combinations thereof.

In one preferred aspect of the present invention, the drug is provided in a coating layer or released from the coating layer in a nanoencapsulated form with a least one encapsulation material in nanoparticles, a least one oil-in-water emulsion, at least one water-in-oil emulsion or at least one liposome material, or a combination thereof. The nanoparticles, when present, can be any disclosed herein or described in the art, including but not limited to, chitosan nanparticle, human serum albumin nanoparticle; silica nanospheres, PEG'ylated core-shell nanoparticles, biodegradable PGGA(poly(D,L-lactide-co-glycolide) particles, PLA (poly lactic acid), PGA, PLG (poly-(D,L-glycolide) polymeric nanoparticles, biocompatible gliadin nanoparticles, low pH sensitive PEG stabilized plasmid-lipid nanoparticles, tocopherol derivatives stabilized nano-sized emulsion particles, PLA-PEG nanoparticles, nanoparticles composed of hydrophilic proteins coupled with apolipoprotein E, biodegradable poly(vesiln-caprolactone) nanoparticles, biotinylated poly(ethylene glycol) conjugated with lactobionic acid, carboxylmethyl dextran magnetic nanoparticles and combinations thereof.

Barrier Layer

The coating of the present invention includes at least one barrier. The barrier layer is preferably provided directly on at least a portion of the at least one drug reservoir layer the second component of the coating of the present invention. However, at least one barrier layer may be provided before an at least one drug reservoir layer in certain aspects of the invention where the direction of release of a drug from a coating of the present invention is desired, such as the case where a medical device presents multiple surfaces for release of a drug from a coating of the present invention, such as, for example, contact lenses where the drug can be released towards the eye, towards the eyelid, or both.

The drug barrier layer can be made of any appropriate material or combination of materials, and the choice of material is generally within the skill of the art as influenced by a variety of factors, including but not limited to the printing method to be used to provide the drug reservoir layer, the size, thickness an shape of the drug receiving layer desired, the physical and chemical properties desired for the drug reservoir as influenced by the chemical and physical characteristics of the drug provided in the drug receiving layer such that the drug can be released at a desired rate, and the like.

Preferred materials for the barrier layer include, but are not limited to, at least one polymer, at least one partially polymerized polymer, at least one polymer matrix, at least one protein matrix, at least one silicone, at least one ceramic, at least one glass, at least one carbon containing compound, at least one fabric or a combination thereof. Other preferred materials include, but are not limited to, derivatized oligomers, such as but not limited to, HEMA, DMA, GMA, PVA, silicone and siloxane, or combinations thereof.

In certain aspects of the present invention, during the printing process used to make the barrier, a non-polymerized or partially polymerized printing formulation, is applied to the surface. In that instance, the non-polymerized or partially polymerized formulation is to be polymerized or otherwise cured to stabilize the barrier layer and, in certain aspects of the invention. Preferred methods for polymerizing or curing a drug reservoir when needed or desirable include, but not limited to, at least one UV curing or polymerization, at least one thermal curing or polymerization, at least one room temperature curing or polymerization, at least one simultaneous printing and curing or polymerization, at least one e-beam curing or polymerization, or combinations thereof.

In one preferred aspect of the present invention, the barrier layer includes structures, particularly structures that can modulate the release of a drug from the drug reservoir layer and the coating layer. The figures provide examples of such structures, and preferred structures include, but are not limited to capillary structures. These structures can be readily made using the printing methods of the present invention, and the size, shape and spacing can be chosen based on a variety of factors discussed herein, including but not limited to the chemical and physical characteristics of the drug passing through the barrier layer upon being released from the drug reservoir layer, the material that the harrier layer is made of, and the resolution of the printing technique used to make the barrier layer.

As discussed herein, the at least one drug does not substantially pass through the barrier layer, but rather the barrier layer serves to modulate the release of the drug from the coating of the present invention.

Printing

One aspect of the present invention is that the various components of the at least one coating are preferable made using at least one printing technology. The components of the coating include, but are not limited a variety of layers, including but not limited to, and may not include all of the listed components, at least one drug reservoir layer, at least one drug receiving layer, and at least one barrier layer. The same or different printing technologies can be used to make the various components. Likewise, one or more printing technologies can be used to make a particular component. The printing of the various components, or layers, preferably uses a printing formulation of the present invention, but that need not be the case. Printing formations of the present invention are described in further detail herein.

A wide variety of printing technologies are applicable to providing the various layers of the coating of the present invention. The choice of which printing technology to use is a matter of choice for the skilled artisan based on the particular size, shape, thickness, printing resolution and other characteristics of the layer being provided. One skilled in the art would have available technical literature to match the desired characteristics of the layer to be printed with the characteristics, benefits and limitations of a printing technology. Likewise, one skilled in the art would be able to match a printing formation used to make a layer of the present invention with a particular printing technology, and the desired characteristics of the layer to be printed as well.

The characteristics of the printing formulation being used to make the layer, such as, but not limited to the viscosity and surface tension of the printing formation. Also, the nature of the printing device in combination with the printing formation is a factor to consider, such as the case when a printing technology, such as but not limited to ink jet printing technology utilize printing structures that may require relatively stringent physical and chemical characteristics of the printing solution such that the printing formulation does not clog or otherwise damage or interfere with the printing device.

In addition, as some of the layers are printed in liquid or semi-solid form and then transformed into a solid or semi-solid form by, for example but not limited to polymerization or partial polymerization, the characteristics of the printing liquid or semi-solid is to be taken into account. As a preferred aspect of the present invention, the compositions of Doshi et al., published U.S. application No. 2008/0062381A1, published Mar. 13, 2008, are applicable, particularly when the pigment is optionally present in such formulations, and at least one drug is optionally provided in such formulations.

Preferred printing methods are digital in nature, such as those described by Doshi et al. (U.S. 2008/0062381A1) which is incorporated by reference herein in its entirety, such that they allow for a relatively highly precise method and means to provide a high quality and well defined print product. As the method and associated device are digital in nature, the printing process is adaptable for computer control and product design. Preferred digital printing methods and structures are discussed herein. As a non-limiting introduction to digital printing methods and devices, the following digital printing methods are preferred: ink jet printing, three dimensional printing (3D printing), piezo printing, thermal printing, laser printing MEMS printing, wherein the printing head or related or associated structures are rotatable or non-rotatable. Generally, but not exclusively, a printing solution of the present invention replaces the ink solution of existing and commercially available printing devices, in particular within the printing cartridge.

Likewise, preferred printing methods include pad printing as those methods are known in the art, including but not limited to pad transfer printing. Pad printing is not as exact as digital printing, but is a preferred method of printing for the present invention. Pad printing is known in the art for printing of images of the iris of the eye on contact lenses (see, U.S. Pat. Nos 5,414,477, 5,302, 978, and 4,668,240).

Ink jet printing is known in the art and can take various forms and associated structures as are discussed herein. Generally, ink jet printing refers to printing devices and methods that utilize highly precise printing methods and structures that allow for the production of high quality and precise structures. Generally, available ink jet printing devices and structures can be utilized with minimal modification, with the ink solutions normally present in the ink jet cartridge or reservoir is replaced with a solution that includes a polymerizable monomer and associated polymerization initiators as needed. The polymerizable monomer can be polymerized at will and at a rapid rate after being dispensed from the ink jet printing structure.

Three dimensional printing is based primarily, but not exclusively, on ink jet printing technologies. These methods and devices allow for the generation of one-off or multiple copies of a structure or structures. Generally, a polymerizable solutions is placed within the printing device and is dispensed under computer control and polymerized in repeated printing cycles or steps to generate a three dimensional structure. Examples of available and preferred 3D printing devices and related structures and cartridges include, but are not limited to: 3D Systems (www. 3dsystems.com/default.asp) (Mar. 29, 2011), ProJet™ 6000 Professional 3D Printer (http://printin3d.com/sites/printin3d.com/files/downloads/Projet_6000_brochure_USEN.pdf) (Mar. 29, 2011); Stratasys, Inc. (http://www.stratasys.com/); Fortus 3D Production Systems—Fortus 900mc; Z Corporation(www.zcorp.com); Zprinter® 650 (http://www.zcorp.com/en/Products/3D-Printers/ZPrinter-650/spage.aspx)Vertical Resolution—90 to 100 microns (0.0035 to 0.004 in) Smallest Feature—100 microns (0.004 in); 3D Systems (http://www.3dsystems.com/default.asp); and Viper si2™ SLA® System http://www.3dsystems.com/products/datafiles/viper/datasheets/Viper_final_rev_0303.pdf.

Piezo printing is a subtype of ink jet printing that is a preferable printing method of the present invention. Examples of available and preferred piezo printing devices and related structures and cartridges include, but are not limited to: MicroFab Technologies, Inc. (www.microfab.com) (Mar. 29, 2011); Jetlab® 4xl, 4xl-A ((http://www.microfab.com/equipment/pdf/jetlab4xl_xla.pdf) (Mar. 29, 2011); X-Y Accuracy/Repeatability—+/−25 microns/+/−5 microns (4xl-A); O.N.E Technologies (www.onelabs.com) (Mar. 29, 2011); Material Deposition Systems (www.onelabs.com/matdep00.htm) (Mar. 29, 2011), Resolution as low as 0.2 nanometer; Multi-Axis Printing Systems (www.onelabs.com/maxp00.htm) (Mar. 29, 2011); FujiFilm USA|Dimatix, Inc. (http://www.dimatix.com/index.asp) (Mar. 29, 2011); Dimatix Materials Printer DMP-5000 (http://www.dimatix.com/files/DMP-5000-Datasheet.pdf) (Mar. 29, 2011) X-Y Accuracy/Repeatability—+/−5 microns/+/−1 microns; Mimaki JF Series (http://www.mimakiusa.com) (Apr. 1, 2011) Model JF1610 or JF 1631 (http://www.mimakiusa.com/IndustrialProduct.aspx?level=3&pid=3&cid=14) (Apr. 1, 2011), resolution up to 1200 by 1200 dpi.

Thermal printing is a subtype of ink jet printing that is a preferable printing method of the present invention. Examples of thermal printing devices and related structures and cartridges include, but are not limited to: Hewlett Packard (www.hp.com) (Apr. 1, 2011); HP Designjet H45000 Printer Series http://www.hp.com/united-states/colorspan/djh45000-datasheet.pdf (Apr. 1, 2011).

Laser printing is a subtype of ink jet printing that is a preferable printing method of the present invention. Examples of laser printing devices and related structures and cartridges include, but are not limited to those known in the art such as Xerox Phaser 6010 laser printer http://www.xerox.ca/office/printers/colour-printers/phaser-6010/spec-en-ca.html or HP Color LaserJet Enterprise CP4025 Printer series—HP Color LaserJet Enterprise CP4025dn Printer (CC490A) http://h10010.www1.hp.com/wwpc/us/en/sm/WF06b/18972-18972-3328060-15077-236268-3965792-3965795-3974244.html, or those later developed.

Optionally, a printing device, such as but not limited to an ink jet printing device, can include a rotating printer head. These types of printing structure can allow for enhanced printing on curved surfaces.

Another preferred printing method is MEMS printing is based on technologies that allow for the printing of integrated circuit boards, but are applicable to the production of very small structures that have functionality. Examples of structures having functionality made by MEMS printing include mechanical gears and other mechanical devices, lab on a chip structures for the performance of laboratory procedures including chemical reactions and diagnostic procedures.

Another preferred printing method is MEMS printing and is based on technologies that allow for the printing of integrated circuit boards, but are applicable to the production of very small structures that have functionality. Examples of structures having functionality made by MEMS printing include mechanical gears and other mechanical devices, lab on a chip structures for the performance of laboratory procedures including chemical reactions and diagnostic procedures.

Printable Formulation

Printable formulations useful in the present invention for printing of layers or structures of the present invention using printing technologies as discussed herein and known in the art, particularly digital printing methods and technologies, can optionally include one or more drugs, any single drug compound or composition, or any combination of drug compounds or compositions. Printable formulations can be provided in water, monomer or solvents, preferably at a concentration between about 0% and greater than about 99.5% or between about 0.001% and about 99.5%, preferably between about 0.005% and about 90% or between about 1% and about 80%, and more preferably between about 10% and about 60% or between about 20% and about 40%. Printable formulations can also include particles or particulates, preferably at a concentration of between about 0% and about 15% or between about 0.001% and about 10%, preferably between about 0.005% and about 4% or between about 1% and about 3% to render a digitally printed formulation optionally with at least one drug. Examples of drugs include, but are not limited to, Timolol, Gentamycin and Nevanac. As discussed herein, the characteristics and compositions including printable formulations and other components include printable formulations that are or become part of an article of manufacture of the present invention, such as a lens, such as a contact lens, and also include compositions that include at least one printable formulations that can be used to make any article of manufacture of the present invention.

Printable formulations can include water, monomer, polymer or an appropriate solvent in order for the printable formulations to be suitable in the making of a digital print. An appropriate solvent is a solvent that is compatible with the creation of a print such as a digital print on or within a surface, such as on or within a polymer. For example, solvents appropriate for polymers used to make lenses, such as contact lenses, include, but are not limited to isopropanol, water, acetone or methanol, either alone or in combination and can include a monomer. Appropriate concentrations of solvents are between about 0% and greater than about 99.5% or between about 0.1% and about 99.5%, preferably between about 1% and about 90% or between about 10% and about 80%, and more preferably between about 20% and about 70% or between about 30% and about 60%. Different polymers, monomers and printable formulations have different tolerances and reactivity to different solvents. Thus, appropriate matches between solvent and polymer, monomer and printable formulations can be considered. For hydrogel polymers, adjustment in swelling ratios may be achieved with a variety of concentrations of solvents or crosslinkers.

A printable formulation can also include a monomer, polymer, homopolymer, heteropolymer, or copolymer. In a preferred aspect of this aspect of the present invention, a printable formulation includes a monomer that can be polymerized to form a polymer using polymerization methods appropriate for a given monomer, mixtures thereof, or polymers, or mixtures thereof. Monomers can also be used to decrease the viscosity of the printable formulation. Alternatively, the printable formulation can include a polymer such that the viscosity of the printable formulation is increased. Alternatively, the printable formulation can include polymer and monomer. Appropriate concentrations of monomers are between about 5% and greater than 99%, preferably between about 25% and about 75%, and more preferably between about 35% and about 60%. Appropriate concentrations of polymers are between about 0% and about 50%, preferably between about 5% and about 25%, and more preferably between about 10% and about 20%. When monomers and polymers are mixed, the total concentration of monomer and polymer are between about 10% and greater than 99%, preferably between about 25% and about 75% and more preferably between about 35% and about 65%.

The viscosity of a solution including a printable formulation can be as high as between about 500 centipoise and about 5,000 centipoise and is preferably between about 1 to about 200 centipoise or between about 10 and about 80 centipoise, preferably between about 20 and about 70 centipoise or between about 30 and about 60 centipoise or between about 1 and about 10 centipoise. Solutions having low viscosity tend to be "runny" when dispensed, and can allow different colors to merge and blend, resulting in an image with a more natural appearance. Such blending can be enhanced using a variety of methods, including sonication or vibration at appropriate duration and frequency to promote appropriate blending. Solutions having too low a viscosity can result in images that are too "runny" and thus have potentially undesirable characteristics, such as pooling of a printable formulation in a digitally encoded image or spreading of a printable formulation to an unintended location. Solutions having too high a viscosity may be easily dispensed using pad printing but are not suitable for other printing. Furthermore, solutions having high viscosity can tend to "bead" on a surface and not blend with the surrounding environment, including surrounding droplets or beads of printing formulation. Agents such as thickeners or diluents (including appropriate solvents) can be used to adjust the viscosity of the printable formulation.

Alternatively, one may use drug receiving layer that holds inkjetted digital droplets in its place until fixed. Another approach can be to use printable formulations that uses derivatized oligomer to be able to stop it from running by instant curing. Both of these approaches are discussed herein.

A printable formulation that includes at least one monomer can also include a polymerization initiator, so that once a printable formulation that includes at least one type of monomer is dispensed, the polymerization of the monomer in the printable formulation is initiated. The number, type and amount of initiator is a matter of choice depending on the type of monomer or monomers in the printable formulation. Appropriate initiators include, but are not limited to, UV initiators that initiate polymerization by UV irradiation, thermal initiators that initiate polymerization by thermal energy.

A printable formulation can also include a dispersant to allow uniform composition of formulation in a container. Dispersants are preferably provided at an appropriate concentration, such as between about 1% and about 10%.

A printable formulation can also include at least one anti-microbial agent or antiseptic agent to kill or reduce the number or multiplication microbial agents, reduce the number of microbial agents, or keep microbial agents from multiplying. Preferred anti-microbial agents include anti-bacterial agents, anti-fungal agents and disinfectants. Preferably, such anti-microbial agents, anti-bacterial agents, anti-fungal agents and disinfectants are provided at an appropriate concentration such as between about 0% and about 1%.

A printable formulation can also include at least one humectant such as 1,3-diozane-5,5-dimethanol (U.S. Pat. No. 5,389,132) at an appropriate concentration. Preferably, the range of concentration of a humectant is between about 0% and about 2%.

A printable formulation can also include at least one antioxidant agent or a low corrosion agent, such as alkylated hydroquinone, at an appropriate concentration, such as between about 0.1% and about 1% (U.S. Pat. No. 4,793,264). A PF can also include a non-kogating agent or non-kogating agent, such as 2-methyl-1,3-propanediol at an appropriate concentration, such as between about 0% and about 1%. A printable formulation can also include an evaporation retarding agent, such as, for example, diethylene glycerol or ethylene glycol at between about 0% and about 2% (U.S. Pat. No. 5,389,132).

A preferred printable formulation can have the following composition:

| Component | Percentage |
| --- | --- |
| Monomer | 0% to 99% |
| Drug or Encapsulated Drug | 0% to 25% |
| Initiator | 0.01% to 2% |
| Solvent | 0% to 80% |

-continued

| Component | Percentage |
| --- | --- |
| Binder or Bonding Agent | 0% to 10% |
| Thickener | 0% to 1% |
| Anti-kogating Agent | 0% to 1% |
| Humectant | 0% to 1% |
| Surfactant | 0% to 10% |
| Cross-linker | 0% to 1% |
| Dispersant | 0% to 10% |

Modulation Of Release Of Drug

As previously discussed, the combination of the layers and components of the coating of the present invention serve to modulate the release of at least one drug from the coating, first from the drug reservoir layer into the barrier layer, and from the barrier layer to outside the barrier layer.

A variety of physical and chemical forces influence the modulation of the release of a drug from a coating of the present invention. These include, but are not limited to diffusion characteristics of at least one layer of a coating of the present invention or the coating itself, capillary action characteristics of at least one layer of a coating of the present invention or the coating itself, mass action characteristics of at least one layer of a coating of the present invention or the coating itself, concentration gradient of a drug in at least one layer of a coating of the present invention or the coating itself, solubility of a drug characteristics of at least one layer in a coating of the present invention or the coating itself, temperature, molecular weight of a drug, size of a drug, encapsulation structures for a drug, thickness of at least one layer of a coating of the present invention or the coating itself, porosity of at least one layer of a coating of the present invention or the coating itself, the pore size of at least one layer of a coating of the present invention or the coating itself, the molecular exclusion size or characteristics of at least one layer of a coating of the present invention or the coating itself, the water content of at least one layer of the coating of the present invention or the coating itself, the concentration of a drug in at least one layer of a coating of the present invention or the coating itself, the concentration gradient of a drug in at least one layer of a coating of the present invention or the coating itself, and the packaging environment presented to the coating of the present invention.

In one aspect of the present invention, the at least one drug has sustained release over time. This aspect of the present invention is described in further detail in Example 9 herein. In another aspect of the present invention, the at least one drug has intermittent release over time. This aspect of the present invention is described in further detail in Example #9 herein. In yet another aspect of the present invention, more than one drug is released at a time. This aspect of the present invention is described in further detail in Example 9 herein.

Contact Lens

In one preferred aspect of the present invention, the medical device having a coating being made includes a contact lens. Contact lenses that include a drug, on the surface of the contact lens or within the contact lens are known in the art. However, these contact lenses do not provide the structures of the present invention, such as the at least one coating that includes at least one drug reservoir layer that can include at least one drug, and at least one barrier layer that can include structures, wherein the release of the at least one drug from the at least one coating layer is modulated by at least one layer of the coating of the present, either alone or in combination.

The choice of printing technologies used to make the various layers of the coating of the present invention, including the coating layer as a whole, is a choice for the artisan based on the state of the art and the teachings provided herein, as well as an evaluation of the various factors to consider when choosing a printing technology to produce a structure having desired chemical and physical properties, along with a consideration of the printing formation to be used.

A variety of materials are known in the art for making contact lenses and are useful in the present invention. Preferred materials include, but are not limited to, acrylics, silicones, polyvinylalcohols, and combinations thereof. These materials are provided on the surface of the contact lens to be modified using the methods of the present invention.

There are a variety of general types of contact lenses known in the art and are useful in the present invention. Preferred general types of contact lenses include, but are not limited to hybrid lenses, hydrophilic lenses and hydrophilic lenses. These types of contact lenses provide a surface of the contact lens to be modified using the methods of the present invention.

In addition, there are other general types of contact lenses known in the art and are useful in the present invention. These lenses include, but are not limited to spherical lenses, tonic lenses, multifocal lenses, tinted lenses, corrective optical power lenses and lenses without corrective optical power. These types of contact lenses provide a surface of the contact lens to be modified using the methods of the present invention There are a variety of methods used to make lenses that are useful in the present invention. Preferred methods of making, at least in part or in combination, contact lenses include, but are not limited to, lathing, cast molding, spin casting and ink jet printing. These contact lenses provide a surface of the contact lens to be modified using the methods of the present invention Once a contact lens is manufactured, a variety of secondary or finishing operations can be utilized and are useful in the present invention. Preferred secondary or finishing operations include, but are not limited to edging, polishing, tinting, hydration, extraction, and sterilization. These secondary or finishing operations can optionally take place before or after the contact lens is modified by a method of the present invention, or both.

In one aspect of the present invention, the at least one drug in an at least one coating layer can be provided on the surface of a contact lens. In another aspect of the present invention, the at least one drug in at least one coating layer can be provided within a contact lens. In another aspect of the present invention, the at least one drug can be provided inside a contact lens without the structures in an at least one coating layer in combination with at least one drug in at least one coating layer on the surface of a lens. In yet another aspect of the present invention, the at least one coating layer with at least one drug can be provided both on the surface of the lens and inside the lens.

In some cases, drugs provided within the at least one coating can have optical properties that can interfere with the optical function of the contact lens, such as drugs having coloring or opaqueness. Preferred drugs for use in the present invention do not have such optical properties, but that need not be the case as drugs having such optical properties are useful in the present invention.

In another aspect of the present invention, the one or more coatings can optionally dispersed therein nanoparticles having a particles size less than about 50 nm, a nanoencapsulated ophthalmic drug from which the ophthalmic drug is able to diffuse into and migration through the contact lens and into the post-lens tear film or towards the eyelid when the contact lens is placed on the eye, the nanoparticles being disperse within the contact lens or on at least one surface of the contact lens in an amount such that the lens optionally remains substantially optically transparent (see, for example, U.S. Pat. No. 7,638,137B2 to Chauhan et al., issued Dec. 29, 2009).

In another aspect of the present invention, the one or more coatings can optionally dispersed therein nanoparticles having a particles size less than about 50 nm, a nanoencapsulated ophthalmic drug from which the ophthalmic drug is able to diffuse away from and migrate away from the contact lens and into the post-lens tear film or towards the eyelid when the contact lens is placed on the eye, the nanoparticles being disperse within the contact lens or on at least one surface of the contact lens in an amount such that the lens optionally remains substantially optically transparent (see, for example, U.S. Pat. No. 7,638,137B2 to Chauhan et al., issued Dec. 29, 2009).

In yet another aspect of the present invention, when the at least one drug is provided with or without a drug delivery compositions as described herein, the at least one drug as provided with or without a drug delivery compositions is substantially optically transparent. However, this need not be the case. In one aspect of the present invention, when the at least one drug as provided with or without a drug delivery composition is substantially optically transparent or is not substantially optically transparent, the optical characteristics of the at least one drug, or other structures of the at least one coating layer, can be masked with opaque material or tinting, such as color tinting as is known in the art.

Packaging

An article of manufacture made by a method of the present invention can be provided in a variety for forms and packaging formats and solutions as present. Many of these packaging form and formats are established packaging formats, whereas others are unique to the present invention.

The article of manufacture made by a method of the present invention can be provided in a packaging in a dry state, preferably in a dehydrated state or a lyophilized state using methods know in the art. The article of manufacture made by a method of the present invention can also be provided in a packaging in a wet state, that is to say provided in an appropriate solution and, as appropriate, in a hydrated state.

The format of the packaging can be any as is appropriate. For example, the article of manufacture made by a method of the present invention can be provided in packaging that is appropriate and normal for the article of manufacture, such as vials, other containers such as boxes or plastic containers, or in vials. Vials and blister packaging are preferable, but not necessary, for example, for contact lenses.

The solution present, if any, in a packaging format, in particular for a wet state packaging format can include the at least one drug present in the at least one coating layer, a different drug that that provided in the coating layer, or a combination thereof.

In one instance, the concentration of the drug in a packaging solution is less than the concentration of the drug in the coating layer. In that case, it is likely that the drug in the coating layer may migrate from the coating layer into the packaging layer and eventually reach a steady state equilibrium state, but that not be the case.

In another instance, the concentration of the drug in a packaging solution is equal to the concentration of the drug in the coating layer. In that case, it is likely that the drug in the packaging solution will be in steady state with the drug in the coating layer, but that need not be the case.

In the alternative, the concentration of the drug in the packaging solution is greater than the concentration of the drug in the coating layer. In that case, it is likely that the drug in the packaging solution would migrate into the coating layer and eventually reach a steady state equilibrium state, but that need not be the case.

In yet another instance, a drug provided in the packaging layer that is not present in the coating layer may be present. In that case, it is likely that the drug in the packaging solution would migrate into the contact lens and eventually reaches a steady state equilibrium state, but that need not be the case.

III Methods of Using Lenses Including a Medicament

The present invention includes method of treating or preventing a disease, disorder or condition or condition including: a) providing a subject in need of treatment of said disease, disorder or condition; and b) providing the subject the article of manufacture of the present invention, optionally made using the methods of the present invention, at a location appropriate for the treatment of said disease, disorder or condition; wherein the article of manufacture releases the one or more drugs in an amount sufficient to treat or prevent said disease, disorder or condition.

The article of manufacture of the present invention, its components and a compositions along with their desirable characteristics and selection criteria, how they are arranged and function together, and what criteria can be utilized to select and arrange them for a particular article of manufacture for a particular purpose, have been described herein. In addition, the methods of manufacture of the article of manufacture of the present invention, along with the manufacture of the coating layer and its various components, including but not limited to the drug reservoir layer, the drug receiving layer, and the barrier layer and structures provided therein, along with the printing formulations and printing technologies used to make them and the physical characteristics of the modulation of drug release therefrom, along with the criteria for selecting them for the manufacture of an article of manufacture for a particular purpose have also been described herein. The criteria for the selection of a drug, including for what purpose it is to be used for, its physical characteristics, its concentration, release characteristics and modulation thereof, have also been described herein.

An article of manufacture of the present invention, optionally made by a method of the present invention, tailored for the treatment or prevention of a particular disease, disorder or condition, and the drug has been selected and provided for in the article of manufacture such that the release characteristics have been evaluated based on the desired dose, regime, route of administration and locus of administration, and the pharmacological characteristics of the drug is provided. The drug has preferably been selected to match the disease, disorder or condition at hand, along with the locus at which it is released based on the criteria disclosed herein and provided by the state of the art.

A subject in need of treatment or prevention of a disease disorder or condition is also provided. The article of manufacture is then place on or within the subject at a desirable location using methods known in the art based on the locus at which the article of manufacture of the present invention is place (such as, but not limited, insertion on a surface, insertion, or implantation, inclusive of surgery if called for) such that the drug is released from the article of manufacture to treat or prevent a disease, disorder or condition. When the drug has been released over time, the article of manufacture can be removed from the subject, or in the alternative, removed from the subject. In the case of an article of manufacture of the present invention that has been placed on readily accessible locus of a subject, such as the skin or eye, the removal is readily performed. In the case of articles of manufacture of the present invention that have been implanted or inserted into a subject, the removal process is more complex and may require surgery. In some instances, removal of an article of manufacture of the present invention from a subject is not desirable due to the discomfort or risk associated with the removal. In that instance, the article of manufacture can remain in place.

EXAMPLES

Example #1

Preparation of Printable Formulation Using A Hydrophilic Drug

This example provides printable formulation with a drug used to inkjet print lenses.

The printable formulation include a base formulation that include the following: monomer (HEMA), initiator (BME), crosslinker (EGDMA), drug #1, diluent (glycerine), solvent (isopropanol), optional drug #2, dispersant (polyvinyl alcohol), humectant (ethylene glycol), co-monomer (methacrylic acid); inhibitor (MEHQ), antikogating agent (methyl propanediol), and antioxidant (alkylated hydroquinone). The concentration of these constituents are as appropriate for making a lens of desired characteristics and physical properties. Drug #1 and optional drug #2 can be any drug or combination of drugs to provide a desired activity.

A preferred monomer mixture for making a clear lenses coating has the following formulation: monomer (HEMA), monomer (EOEMA), monomer (MAA), crosslinker (EGDMA), initiator (Vazo-64), inhibitor (MEHQ) and diluent (glycerine). The concentration of these constituents are as appropriate for making a lens of desired characteristics and physical properties.

When drugs are used in jet printing devices, the drug is preferably water based or monomer based (U.S. Pat. No. 5,658,376). The drug is preferably soluble in water and an organic solvent and preferably includes a dispersant. A water soluble polymer such as polyvinyl alcohol and a dispersant such as polyvinylpyrrolidone are-preferred. A surfactant is preferably provided, such as polyoxyethylene alkyl ether or polyoxyethylene alkylphenyl ether having an aminic acid group. The printable preferably includes a surfactant, such as between about 0.3% and about 1% by weight. The PF preferably includes an antiseptic agent such as Proxel (Zeneca, U.K.). The printable formulation preferably has a pH of between about 7 and about 10 and a viscosity at about 25C of between about 1 to 50 cps. Antioxidants, such as low corrosion or antioxidant agents, such as alkylated hydroquinone can also be included, preferably between about 0.1% and about 0.5% by weight (U.S. Pat. No. 5,389,132). A printable formulation can also include a humectant such as 1,3-dioxane-5,5-dimethanol, 2-methyl-1,3-propane diol, ethylene glycol or diethylene glycol. When used in printing, the driving frequency is preferably between about 3 kHz and about 8 kHz (see generally, U.S. Pat. No. 5,658,376). Preferred printable formulation properties include a surface tension of between about 20 dynes/cm and about 70 dynes/cm and a viscosity between about 1.0 cp and about 2.0 cp (U.S. Pat. No. 5,271,765).

Example #2

Solvent Soluble Drug

This example provides a printing formulation with a solvent soluble drug used to inkjet print lenses.

A preferable formulation with a solvent soluble drug has the following composition and physical properties.

| Materials | Material Type | Percent | Range |
| --- | --- | --- | --- |
| DI Water | Solvent | 71.47 | 60-80 |
| Glycerin | Solvent | 6.67 | 1-20 |
| 1,3-propandiol | Solvent | 6.67 | 1-20 |
| Water Soluble Drug | Drug | 13.33 | 0.001-20 |
| Surfynol CT 121 | Surfactant | 0.53 | 0.2-20 |
| Triethyl Amine 10% in water | Additive | 1.33 | 1-5 |
| Total | | 100 | |

Viscosity=3.5 centipoise, UL, 60 rpm, 25° C.
Surface tension=32 dynes/cm;
pH=8.4.
The formulation was filtered through 0.45 micron Nylon filter membrane.
Water=Main vehicle, carrier
Glycerin, 1,3-propandiol=co-solvents
Surfynol CT121 and 10% TEA solution=additive The printable formation can also include a drug in encapsulated form. There are several methods available for encapsulation to meet the product performance requirements. These methods can be divided into 2 broad categories: (see, for example, Southwest Research Institute ((SWRI) website, www.microencapsulation.swri.com), an outline summary of which follows:

1.) Preferred physical methods of encapsulation include, but are not limited to:
Extrusion
Fluidized bed
Pan coating
Atomization,
Spinning Disk
Spray Drying
Spray Chilling/Congealing
SphereJet by Microfab 2.) Preferred chemical methods of encapsulation include but are not limited to:
Solvent loss
Phase separation
Coacervation
Polymerization
Precipitation
Nanoencapsulation
Liposomes
Sol-gel These methods and related technologies are well documented in literature and is incorporated in this patent. (See, for example "MICROENCAPSULATION TECHNIQUES, FACTORS INFLUENCING ENCAPSULATION EFFICIENCY: A REVIEW" by N. V. N. Jyothi; Suhas Narayan Sakarkar; G. Y.Srawan Kumar; Muthu Prasanna. Source: journal of microencapsulation, Informa Health Care, Volume 27, Issue 3, p.187-197).

In addition, Chauhan et al. in U.S. Pat. No. 7,638,137 B2, provides a detailed list of various types of nanoparticles, including silica used for encapsulating drugs. (See, for example, page 5, lines 9 through 80). Chauhan et al. also discusses different types of micro-emulsions and methods used to prepare them. Chauhan et al. also provides details of drug release studies carried out with a micro- or nano-encapsulated ocular drug, Lidocaine, when embedded inside the lens while the present invention has a novel approach of incorporation the drug on the surface of the lens rather than inside the lens. Many of the aspect for drug release are essentially the same (see, for example, U.S. Pat. No. 7,638,137 B2).

The following is an example of a printable formulation for a micro- or nano-encapsulated hydrophobic ocular drug such as Timolol that may be incorporated in a printable formulation that uses a derivatized oligomer of HEMA to provide dimensional stability and good adhesion when the finished, hydrated lens may be sterilized multiple times.

Example #3

Preparation of an Oligomer Capable of Free Radical Polymerization for use in Printable Formulations A Poly hydroxy ethyl methacrylate prepolymer is prepared according to the following procedure. The following components are mixed:

| Material | % |
| --- | --- |
| Methacrylic acid | 0.82% |
| Mercaptoethanol | 0.70% |
| Allyl methacrylate | 0.16% |
| Ethyl triglycol methacrylate | 3.50% |
| N-Vinyl pyrrolidinone | 6.07% |
| 2-Hydrozyethyl methacrylate | 35.42% |
| Vazo 64 | 0.33% |
| 1-Ethoxy-2-propanol | 44.80% |
| 1-Methoxy-2-proply acetate | 8.21% |

Thermal polymerization is carried out in a steel can fitted with an over head stirrer and mounted on a hot plate. The mixture is heated and temperature of the mixture is maintained at about 85° C. to about 90° C. by moving the can/stirrer assembly between cold water bath and the hot plate as necessary. The reaction is allowed to continue for about 37 minutes from initially reaching 85° C. prior to quenching polymerization by placing the can/stirrer assembly into the cold water bath. The cold prepolymer viscosity is checked and stored in a refrigerator. A typical viscosity of the prepolymer is about 2000 cp to about 3000 cp.

To a solution of 20 grams of the Polyhydroxy ethyl methacrylate prepolymer with a viscosity of 2000 to 3000 cP in solvent 1-methoxy-2-propanol is added 0.2 grams of triethyl amine and stirred well with a magnetic stir bar for 30 minutes. 2 grams of methacryloyl chloride solution, 10% in 1-methoxy-2-propanol, is added while stirring at room temperature. The reaction mixture is stirred overnight thus creating a prepolymer derivative, or an alpha beta unsaturated oligomer.

It is noted that derivatized oligomer for polyvinyl alcohol, glycidol methacrylate, silicone, n-n-dimethylacrylamide can be prepared similarly to facilitate free radical polymerization with these polymers.

Example #4

Printable Formulation For Ink-Jet Printing a Drug Reservoir With Drug

The amount of the alpha beta unsaturated oligomer, or prepolymer derivative, provided in Example 2 and 2-hydroxyethyl methacrylate (HEMA) are prepared for comparison according to the following table:

Sample Printable Formulation

| Components | % | Range (%) |
| --- | --- | --- |
| Prepolymer derivative from Example # 2 | 20 | 5-15 |
| Encapsulated drug like Timolol for Glaucoma in HEMA: | 8 | 0.001-25 |
| PEG 400 diacrylate: | 5 | 0-10 |
| N-vinyl-2-pyrrolidone monomer hydrogel: | 26 | 0-99 |
| Glycerol methacrylate monomer hydrogel: | 133 | 0-99 |
| 2-hydroxyethyl methacrylate monomer hydrogel: | 32.7 | 0-99 |
| Photoinitiator (Irgacure 1800): | 3.5 | 0-10 |
| Photoinitiator (Irgacure 819): | 1.5 | 0-10 |
| Total | 100 | |

The viscosity and surface tension of the printable formulations are measured and the results are as follows:

| | Actual | Range |
| --- | --- | --- |
| Viscosity (cp) | 15.4 | 5-50 |
| Surface Tension (dynes/cm) | 38.1 | 20-70 |

It is noted here that:

1.) Removal of drug from the PF Example #3 can provide printable formulation for an inkjet printed barrier layer.

2.) Barrier layers of different polymers can be also made by using derivatized oligomer of pertinent polymer.

Example #5

Use of a Printable Formulation for Pad-Transfer Printing Drug Receiving Layer

A printable including an oligomer capable of free radical polymerization can also be used with pad-transfer printing. Printable formulations of the present invention for use with a pad-transfer printing technique can be provided at a viscosity form about 5,000 cp to about 50,000 cp. Printable formulations can be adjusted to a higher viscosity by substituting a relatively low molecular weight oligomer as provided herein with an oligomer having a higher molecular weight such as one that results in a polymer from about 20,000 cp to about 50,000 cp. The viscosity can be further adjusted by the addition of polymers or monomers or surfactants.

Pad-transfer printing of a layer may include dispersing the printable formulation having a viscosity from about 5,000 to about 50,000 on a mold or a cliche, dipping a substrate or polymer in the solution and curing the resulting drug reservoir on substrate or polymer. The curing, hydration and sterilization process may be the same as those previously disclosed in the inkjet printing examples and as described herein.

An example of such a printable formulation is provided below.

Prepolymer Formula
For a Pad Printed Receiving Layer

| Ingredient | % | Range (%) |
|---|---|---|
| HEMA | 26.7% | 0.5-90 |
| NVP | 14.4% | 5-40 |
| Allyl Methacrylate | 0.4% | 0.1-2 |
| 2-Mercaptoethanol | 1.3% | 0.1-2 |
| MAA | 0.8% | 0.1-4 |
| Vazo 64 | 0.3% | 0.1-2 |
| Ethyl triglycol methacrylate | 3.5% | 0.1-5 |
| 1-Ethoxy-2-propanol | 44.4% | 10-80 |
| 1-Methoxy-2-propyl acetate | 8.1% | 2-30 |
| Total | 100.0% | — |

Visc~5000 cp
Pad Print Formulation

| Ingredient | % | Range (%) |
|---|---|---|
| Pre-polymer from Above | 0.893 | 0.1-10 |
| Hardener (Blocked HDI) | 0.107 | 0.1-2 |
| Total | 100.0% | |

When the above printable formulation is cured in vacuum oven at 140° C. for about 1 hour it provides the drug receiving layer for a solvent soluble drug.

Example #6

Printing Methods for Use with Printable Formulations

One advantage of present invention is to print structures of the surface of a medical device, such as a lens, not only to achieve desired drug release rate but also offer flexibility of incorporating multiple drugs for multiple treatments, intermittent drug release, consistent drug release of zero order kinetics, uni-directional drug release, etc. without optical interference. Such structures can be printed using various printing techniques that include, but are not limited to, inkjet printing, piezo printing, thermal printing, laser printing, pad transfer printing, impregnation, photolithography, silk screen printing, micro-dispensing material deposition system, SLA stereolithography systems, 3D printers, etc. Some advantages of such printing are that this additive manufacturing technology offers include, but are not limited to material savings, mass customization, high precision automation friendly system (see, for example, The Economist: 3D printing: The printed world: Three-dimensional printing from digital designs will transform manufacturing and allow more people to start making things. Feb. 10, 2011, FILTON, from the print edition).

Printing of such structures, preferably carried out with digital printers (inkjet printing or laser printing, for example) essentially uses inherent advantages of digital printing, that includes, but is not limited to, drop on demand with a preferable volume of less than 5 picoliter to 500 picoliter, with more than 2400 dpi, and with high speed, more than 500 sq. ft./hr, which are characteristics or features of inkjet printers. The following is a list of printers, including but not limited to, printers currently used for constructing 3D structures are given below. Some of these printers have position accuracy of +/−2.5 micron and repeatability of +/−1 micron at present. Incorporated herein are such printers, available now or such printers with better accuracy, precision, repeatability, quality, and the like, which may or will be available at a later date.

In addition to these types of 3D printers, currently available high precision, high speed, high resolution, wide format, piezo printers, thermal printers, laser printers can be modified to digital print layer by layer the structures of the present invention.

Example #7

Inkjet Printing of 3D Structures
A. Inkjet Printable Formulations in Cartridge
In a simplified version of such printers with multiple cartridges will have the following printable formulations in different cartridges
1.) Drug receiving layer
2.) Drug Reservoir with drug
3.) Soluble drug formulation
4.) Barrier layer A formulation
5.) Barrier layer B formulation
6.) Barrier layer C formulation For multiple drug system additional cartridge may be incorporated or existing cartridge may be substituted for additional drugs.

B. Digital Storage of 3D Structure
Using appropriate software like SolidWorks, a 3D drawing of desired structure is digitally stored in a computer.
The computer software for a 3D printer would divide such 3D structures in multiples of layer by layer coatings.

C. Inkjet Printing:
Such layer coatings are then inkjet printed sequentially, cured, fused using appropriate curing/fusing process to build the desired 3D structures.

Thickness of layer (inclusive of a drug reservoir layer, a drug receiving layer, a harrier layer or a combination thereof) can be preferably be controlled to about or less than 0.1 micron to about or less than 10 micron using preferable drop volume of less than about 1 picoliter to less than about 100 picoliters.

Examples of Inkjet printers, included but not limited to, that may be used are given earlier. In addition many commercially available flat bed wide format printers, like Mimaki JF 1610 and 1631 or HP Designjet H45000 printer series, that are high speed, high precision, can also be modified and used for the applications of the present invention. Such printers may use piezo printerhead like Spectra Polaris PQ512/15 AAA or gray scale, drop on demand printing system along with simultaneous UV cure system (Xennia XJ-4000) or thermal cure system.

Example #8

Modulation of Drug Release Rate
Generally the drug release rate can be modulated through one or more of the following factors available to one with understanding of the art.
1.) Creation of different barrier layers with different diffusivity, different thickness
2.) Different drug concentration at different heights, locations and surface area.
3.) Different sizes of nano- or micro-encapsulated drug The present invention also offers creation of capillaries of different diameter or different height to provide additional tool for modulating drug release rate.

The Lucas-Washburn equation that predicts the rise of the fluid meniscus, H(t), in the capillary with time t is given as:

$$H(t) = [(sR \cos \varnothing/2n)^{1/2} t^{1/2}$$

Where: s=fluid surface tension
n=fluid shear viscosity
R=pore radius
Ø=contact angle between meniscus and wall
(Ref. D. I. Dimitrov 1, A. Milchev1,2, and K. Binder, Institut für Physik, Johannes Gutenberg Universität Mainz, Staudinger Weg 7, 55099 Mainz, Germany
2Institute for Chemical Physics, Bulgarian Academy of Sciences, 1113 Sofia, Bulgaria, Received 30 Mar. 2007; published 31 Jul. 2007).

One can use this equation to determine the drug release rate, $R_{capillary}$, for a capillary of given height, diameter, contact angle, viscosity and surface tension. The diameter and height of capillaries can be at the nanometer level, for example, they can be less than 5 nanometers to 50,000 nanometers.

Example #9

Modulation of Drug Release Rate Using a Combination of Factors

Figure 10:
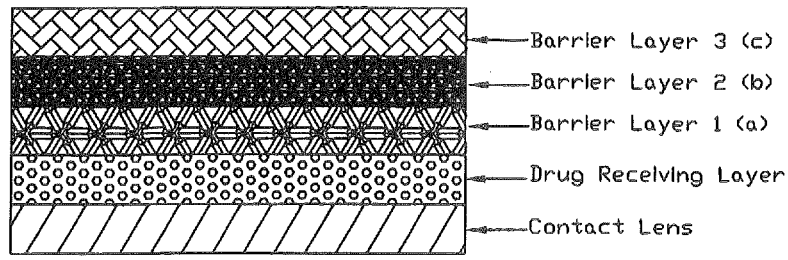
FIG. 10 depicts structures of the present invention where layers of at least one barrier layer are provided above one another over at least one drug reservoir layer. The rate of diffusion of a drug from the at least of drug reservoir layer through the three barrier layers A, B, and C can be expressed as Rate=$R_a \times R_b \times R_c$.

Referring to FIG. 10 and FIG. H, it can be observed that drug release rate may be modulated by changing orientation of the barrier layers A, B and C.

Thus for FIG. 10, where the barrier layer A, B and C are on top of each other, the drug release rate R is:

$$R_{drug} = R_a \times R_b \times R_c \quad (I)$$

Figure 11:
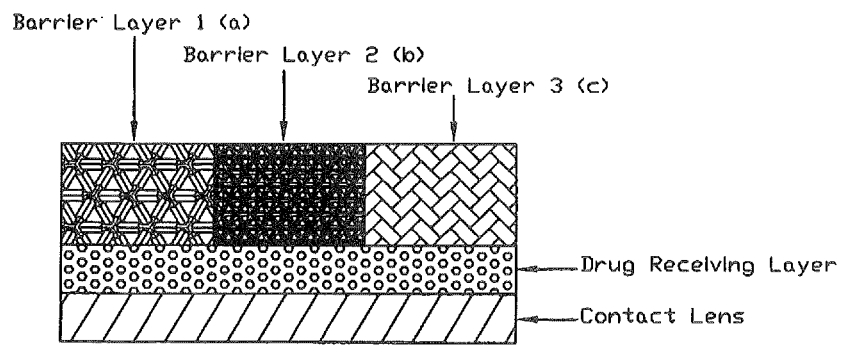
FIG. 11 depicts structures of the present invention where layers of at least one barrier layer are provided along side one another over at least one drug reservoir layer. The rate of diffusion of a drug from the at least of drug reservoir layer through the three barrier layers A, B, and C can be expressed as Rate=$R_a+R_b+R_c$, where $R_a$, $R_b$ and $R_c$ represent drug release rates through materials through materials A, B, and C, respectively, and are related to thickness and other physical and chemical properties of the material.

Whereas for FIG. 11, for the same drug and same barrier layers, one can modulate drug release rate, significantly just by constructing the barrier layers A, B and C next to each other. The drug release rate in that case now becomes $$R_{drug} = R_a + R_b + R_c \quad (II)$$

Figure 12:
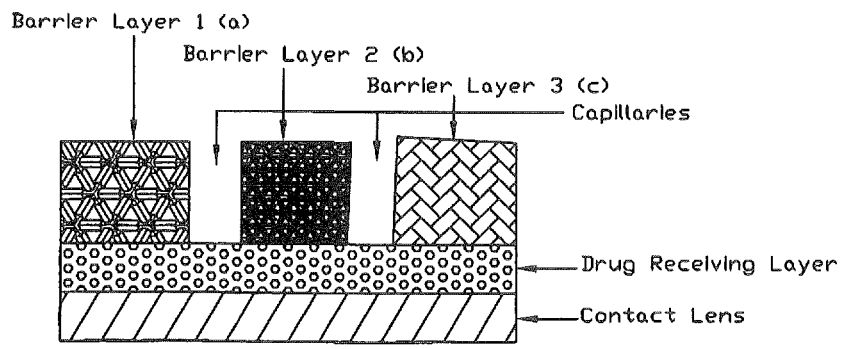
FIG. 12 depicts structures of the present invention where layers of at least one barrier layer are provided along side one another over at least one drug reservoir layer and provide capillary structures in between them. The rate of diffusion of a drug from the at least of drug reservoir layer through the three barrier layers A, B, and C can be expressed as Rate=$R_a+R_b+R_c+R_{capillary}$.

This drug release rate can further be modified by printing structures with capillaries as shown in FIG. 12. The drug release rate is now modulated to:

$$R_{drug} = R_a + R_b + R_c + R_{capillaries} \quad (III)$$

Equation I, II, and III suggests ability to modulate the drug release rate through constructing a three dimensional structure with different barrier materials, controlling thickness and orientation of barrier layer, providing additional structure of capillaries, adjusting drug concentration (by printing number of drops, size of drops, location of drops etc.) it will be possible to get the desired drug release rates including but not limited to zero order kinetics i.e. sustained drug release rate.

Additionally it may be observed from FIG. 8, for multiple drugs, how two different drugs can be delivered at different rate from the lens surface by locating drugs in different area with different barrier layers chosen to provide the desired drug release rate for each drug.

Similarly, by referring to FIG. 4, where drug reservoir layers of different surface area are created at different height from the lens surface, as well as capillaries of different heights and diameters are created; can be used to provide intermittent drug release. For example, let us say that all of the drug from the top reservoir is released in the first two hours. The barrier layers and capillary height from reservoir 2 is constructed such a way that it will take drug 4 hours to reach the top of the lens surface.

Example #10

Lens Finishing

The contact lens surface on which the 3D structure is created can be treated with proper edging/polishing process to help assure lens wear comfort. These lenses then can be hydrated, extracted, and inspected. Packaged and sterilized. The packaging can be with dry lens where solution is provided separately to hydrate the lens before use. The conventional wet packaging in a vial or blister pack may be done in such a way as not to affect drug release rate in the eye, when in use, by controlling the concentration of drug in packaging environment or such similar way. Also, the barrier layer, drug receiving layer and drug reservoir layer are formulated such that they swell the same or substantially the same as the substrate lens so that it does not substantially affect lens dimensions.

Example #11

Therapeutic Contact Lens With a Drug (Such as a Glaucoma Treating Drug (e.g. Bimatoprost), a Comfort Enhancing Agent (a Drug) (e.g. Hyaluronic Acid (HA)), or a Combination Thereof Background This example relates generally to the production of a drug delivery contact lens that delivers two drugs, a glaucoma treating drug (e.g. Bimatoprost) and a Comfort Enhancing Agent, a drug, (e.g. Hyaluronic Acid (HA)). Glaucoma affects 60.5 million people worldwide. Glaucoma poses a serious public health challenge, as it results in vision loss and irreversible blindness if left untreated. The incidence of blindness is higher among African Americans and Hispanics [17]. Traditionally, glaucoma is treated with topical medications, notably eye drops. However, eye drops faces problem such as low bioavailability, increased side effects, and poor patient compliance. To address these issues, the use of a contact lens to provide sustained release of a drug to treat glaucoma and other ocular diseases has been researched for the last several decades. In addition, studies have found that 40 to 50% of glaucoma patients have dry eye syndrome [1], [2]. Thus, there is an additional need to address the issue of dry eye, as discomfort may lead patients to discontinue the use of a medicated contact lens potentially reducing the effectiveness of contact lenses as a medium of drug delivery.

Non-invasive approaches have been reported which (a) use existing contact lenses and provide drug release through pre-soaking, or (b) require development of a new contact lens to incorporate drugs inside the lenses. However, these approaches have not been commercialized due to several limitations. First, the drug containing lens manufacturing process does not use existing high speed manufacturing lines. Thus, the lenses cannot be made cost-effectively. Second, the drug released from inside the lens can interfere with lens characteristics like optics, lens dimensions etc. Third, the technology developed for one drug and lens cannot be easily extended to other drugs using existing technologies. Finally, the current approaches do not allow for multiple drugs on a single lens as may be required for glaucoma patients with, for example, "dry eye."

However, an effective non-invasive replacement for topical applications has not been commercially developed due to the limitations of available technology and high costs. This leaves a large unmet need. Thus, an effective, safe, and low-cost glaucoma therapy that can provide increased clinical efficacy and is conducive to patient compliance is needed. The present invention provides a glaucoma treatment that has high clinical applicability and is cost effective so that it can reduce preventable blindness for millions of affected patients.

The present invention provides a therapeutic contact lens that provides simultaneous release of a glaucoma drug and a comfort enhancing agent (a drug), using 3D Digital Printing technology and/or other printing technologies. As such, the present invention provides a long awaited, more effective, low-cost and comprehensive solution for glaucoma patients and can meet this unmet need.

BRIEF SUMMARY OF THE INVENTION

The present invention provides a drug-eluting, cost-effective, commercially viable, and comfort-enhancing contact lens made at least in part using 3D digital printing and/or other printing technologies, for the treatment of a variety of diseases, disorders and conditions, such as those of the eye, such as glaucoma. Glaucoma affects 60.5 million people worldwide and poses a serious public health challenge, as it results in vision loss and irreversible blindness, if left untreated. Traditionally, glaucoma is treated with topical medications, such as eye drops. However, topical treatment faces problems including low bioavailability, increased side effects, and poor patient compliance.

The present invention provides a solution to these limitations which includes a therapeutic extended wear contact lens that provides simultaneous, sustained release of a glaucoma drug, Bimatoprost, and a comfort enhancing agent/drug, Hyaluronic Acid (HA), using existing FDA approved contact lenses and 3D and/or other printing technology. The present invention includes 3D Digital Printing and/or other printing technologies to produce contact lenses with sustained drug release. The use of 3D Digital Printing technology and/or other printing technologies provides improved manufacturing technology that allows digitally print "drug loaded ink" on the surface of existing contact lenses, and to modulate the drug release rate by building appropriate drug reservoirs and barrier layers. The present invention provides contact lenses as drug delivery devices for many other ocular diseases including but not limited to allergy, infection, and dry eye.

The present invention provides for the sustained release of drugs via contact lenses. In one aspect of the present invention, sustained release of Bimatoprost and/or HA printed on the surface of methafilcon lenses can be achieved from between about 1 hour and about 30 days, preferably between about 2 hours and about 20 days, more preferably between about 3 hours and 10 days, more preferably from between about 4 hours and about 5 days, and more preferably between about 5 hours and about 2 days. In a preferred aspect of the present, the lens can provide (1) sustained release of at least between about 1 hour and about 15 days, preferably between about 2 hours and about 10 days, more preferably between about 3 hours and 5 day, more preferably between about 4 hours and 2 days, and more preferably between about 5 hours and 1 day for Bimatoprost and HA individually and together; (2) the drug is not affected by 3D Digital Printing of the drug loaded ink on the contact lenses; and (3) lens integrity is maintained.

DETAILED DESCRIPTION

Wichterle reported the use contact lenses for sustained drug delivery in 1965 (U.S. Pat. No. 3,220,960 (1965)). In the last fifty years, significant efforts have been made to provide non-invasive solutions using contact lenses as a drug delivery device [8], [9], [10], [14]. A number of non-invasive approaches [3],[4],[5],[6],[7] have been developed which (a) use existing contact lenses and provide drug release through pre-soaking or (b) require development of a new contact lens to incorporate drugs inside the lens by different methods.

However, these approaches have not been successful because of several limitations, including the following: 1) The lens manufacturing process reported are complex and do not use existing high speed automatic manufacturing production lines and thus, the lenses cannot be made in a cost-effective manner; 2) the existing technology does not allow for easy modulation of the drug release rate; 3) the drug released from inside the lens can interfere with desirable lens characteristics such as but not limited to lens dimensions, optics, light transmission, and the like; 4) each application of existing technologies to a different drug can carry the evaluation or need of new regulatory approval for the lens; 5) technology developed for one drug and lens would not be easily extended to other drugs; 6) the current approach does not address the issue of "dry eye," which results in a risk of patient dropout and non-compliance to treatment if not addressed; 7) the current approaches do not allow for multiple drugs on a single lens, which can be required for glaucoma patients with dry eye.

All of the above current limitations point to an inadequate approach due to technology limitations in the field. The present invention overcomes these technology and commercialization barriers of existing technologies and provides related benefits as well.

The present invention provides solutions to the barriers and provides, for example, simultaneous, sustained release of a commonly used glaucoma drug, Bimatoprost, and a comfort-enhancing agent (a drug), Hyaluronic Acid (HA), using FDA approved existing contact lenses and 3D Digital Printing technology. This can drastically improve both the technical capability and clinical practice of ocular drug delivery through contact lenses. To date, it is not feasible to create a low-cost marketable contact lens that can both improve the comfort of use and deliver multiple drugs to a patient. Thus, the present invention provides a unique way to treat subjects and patients for ocular conditions, including glaucoma. The present invention provides a comprehensive and customizable sustained drug delivery platform for not only glaucoma therapy but also for many other ocular diseases.

Exemplary comfort enhancing agents or compounds include but are not limited to Hyaluronic Acid (HA), cyclosporine, polyethylene glycol 400, hypromellose, polyvinyl alcohol, carboxymethylcellulose, dextran 70, hydroxypropyl methylcellulose, anhydrous liquid lanolin, mineral oil, white petroleum, mannitol, thiomersal, carbomer, cetrimide, glycerin, polysorbate80, povidine. Other comfort enhancing agents are included in the present invention, whether known now or later developed. Glaucoma drugs include but are not limited to timolol maleate, timolol hemihydrate, betaxolol, levohunolol, metipranolol, apraclonidine, Brimonidine tartate, Brinzolamide, methazolamide, dorzolamide, acetazolamide, pilocarpine, carbachol, travoprost, bimatoprost, latanoprost, latanoprostene bunod, tatluprost, netarsudil. Other glaucoma drugs are included in the present invention, whether known now or later developed.

Example #11A

The present invention provides the sustained drug release from the surface of a commercially available FDA approved contact lens by leveraging 3D Digital Printing technology and/or other printing technologies to overcome many of the limitations of the existing technologies.

Example #11B

The present invention provides a lens that can shift the current research approach by incorporating the drug inside the lens to achieve sustained drug release.

Example #11C

Figure 2:
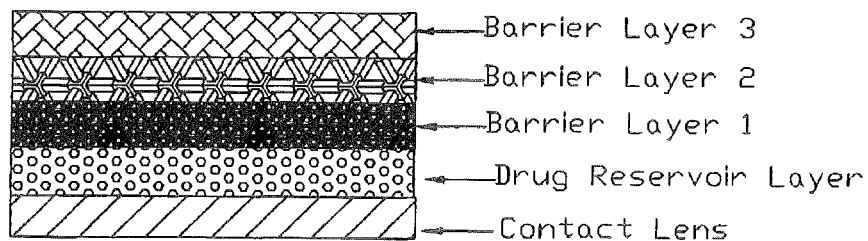
FIG. 2 depicts different types of 3D structures built on the surface of a medical device such as but not limited to a contact lens to obtain a desirable drug release rate.
Figure 3:
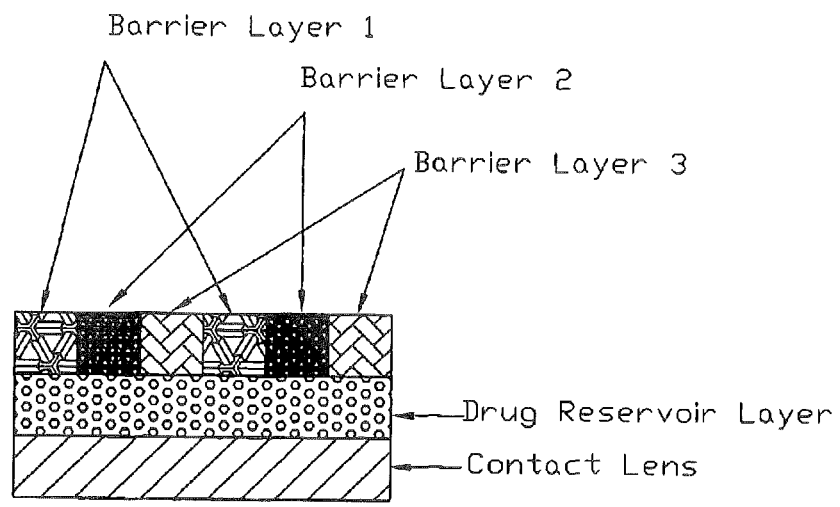
FIG. 3 also depicts different types of 3D structures built on the surface of a medical device such as but not limited to a contact lens to obtain a desirable drug release rate.

The present invention provides the use of 3D Digital Printing, hailed as the "Rise of the Third Industrial Revolution" [13], to produce contact lenses with sustained drug release. 3D Digital Printing has many features such as but not limited t non-contact, precision placement, highly automated, flexibility, and the like. Such features result in a high quality, low-cost product from a manufacturing process which is compatible with current high speed automated manufacturing lines for contact lenses. The use of cutting edge 3D Digital Printing technology provides an improved manufacturing technology that will allow not only digitally print drug loaded ink on the surface of an existing FDA approved contact lens, but also to modulate the drug release rate by building appropriate 3D drug reservoirs and barrier layers. For example, as shown in FIG. 2 and FIG. 3 of the present application, using the "drop on demand" feature of 3D Digital Printing one can achieve different release rates by adjusting the orientation (horizontal to vertical) of barrier layers 1, 2 and 3. Thus, the present invention provices a flexible solution to existing technological barriers in the fields that has numerous advantages over the existing approach.

Example #11D

The present invention provides many improvements in ocular drug applications and can create new drug release applications. The present invention provides the use of 3D Digital Printing and/or other printing technologies upon or within contact lenses to create a new application for contact lenses, as drug delivery devices for many diseases, disorders and conditions, including but not limited to of ocular diseases like glaucoma, allergy, infection, and dry eye, and others as well. The following is a list of other considerations for the development of drug delivery contact lenses.
1. In the examples Bimatoprost is used because (a) it is commonly prescribed, (b) it offers a first-line treatment, and (c) it demonstrates minimal systemic or local toxicity at therapeutic doses.
2. Hydrogel lenses are sold as "steam sterilized". The present examples show the sustained release of HA as shown in Diagram 2 indicates that there was no significant impact of sterilization. Also sterilization with ethylene oxide may be preferred, as it does not raise the issue of release while in inventory.
3. Various In-vivo studies, conducted by many researchers [3], [12], have shown that bio-availability of drug released from contact lenses is at least 5 times more than that from eye drops. It is reported that normally 1-5% of the drug in eye drops gets used for treatment [6], [15], [16].
4. The examples may utilize ink ingredients that are FDA approved for ocular application to facilitate FDA approval and minimize any potential safety issues.
5. Current reports have shown an extended delivery of glaucoma therapies from a contact lens delivery system for 7 days or more. These delivery systems only release therapeutics for glaucoma treatment such as Bimatoprost, Latanoprost, or Timolol. However, this delivery system does not address the issue of "dry eye" experienced by a glaucoma patient. The examples utilize a comprehensive solution, to provide sustained release of Bimatoprost and comfort-enhancing agent/drug HA for 4 hours to 14 days to the glaucoma patient, though narrower and other ranges are part of the present invention. The use of extended wear methafilcon lens for 1 day to 7 days also can reduce the risk of microbial infection as compared to an extended wear of 30 days, though narrower, broader, and other ranges are part of the present invention.
6. Preferably, the ink can be printed outside the optic zone of about 5 mm.

Example #11E

The present invention can have certain desirable characteristics, including but not limited to the following:
A. Sustained release of Bimatoprost, printed on the surface of methafilcon lenses for extended wear for 7 days or more.
B. Sustained release of Hyaluronic Acid (HA), printed on the surface of methafilcon lenses for extended wear for 7 days or more.
C. Sustained simultaneous release of Bimatoprost and HA for extended wear for 7 days or more from the surface of methafilcon lenses.
D. Preservative free is possible, as the methafilcon lenses are terminally sterilized via steam sterilized after they are packaged in packaging solution.

Base ink, such as that described in Example 3 and Example 29 as an oligomer capable of free radical polymerization for use in printable formulations, is used. This base ink is tested for its inkjettability, water content, toxicity, bonding strength, and dimensional stability to confirm its compatibility with methafilcon lenses. Below is the outline of procedure.

The following steps are generally followed. Although the approach is given for Bimatoprost, the same steps are followed for the sustained release studies for HA and for Bimatoprost and HA together.
1. Identification and characterization of drug Latanoprost or Bimatroprost (or other glaucoma treating drug): Are done with Fourier Transform Infrared Spectroscopy (FTIR), UV absorption Spectroscopy, and Differential Scanning Calorimetry (DSC).
2. Quantification of Latanoprost or Bimatoprost (or other glaucoma treating drug): Measure the amount of drug released during the in-vitro study, an analytical test method is used.
3. Loading of Latanoprost or Bimatoprost (or other glaucoma treating drug) in the base ink: is performed using available methods, such as, for example, by the utilization of the following be present in the ink formation and can be present on the medical device being produced and the final product:

| | | |
|---|---|---|
| Microemulsion | Liposomes | Biodegradable Nanoparticles |
| Micelles | Microspheres | Niosome |
| Encapsulated nanoparticle | Ethosomes | Temperature sensitive smart polymers |

4. Characterization of 'Latanoprost or Bimatroprost (or other glaucoma treating drug) loaded ink': is performed using one or more of the following:
   a. Surface tension & viscosity measurements for evaluating inkjettability
   b. Contact angle measurement—for evaluating the wettability of ink on the contact lens
   c. Dynamic light scattering and zeta potential measurement to evaluate particle size, size distribution, polydispersity index, and stability of drug particles in the ink
   d. pH measurement—to evaluate formulation stability and avoid potential irritation in the eye
   e. Stability of drug in the ink to evaluate that there is no or substantially no or reduced degradation or chemical change in drug with time
5. 3D Digital Printing of drug loaded ink:
   a. Utilize commercially available dry methafilcon lenses for inkjet printing.
   b. Prepare lenses to create a drug reservoir layer on the surface of the lens to hold low-viscosity ink in place till it is reacted or cured.
   c. Drug loaded ink is inkjetted to create a reservoir on the lens surface after evaluating 3D inkjet printer parameters to obtain a well/surface-deposited layer of the drug.
   d. Build a barrier layer with a 3D printer using inks that developed to match the properties of the lens. As shown in the examples and figures, one can achieve different drug release rates by creating different structures with a 3D printer. (See, for example, US Published Patent Application No. 2011/0244010 A1 for more details).
6. Testing of 3D Printed Contact Lens:
   a. In-Vitro release kinetic study (Flux study) in simulated tear fluid. The printed contact lenses are placed in 2 ml of simulated tear fluid in a glass vial (20 ml capacity) at 34° C. The vial is placed in an incubator with a shaker at 100 RPM. The volume of 2 ml is used to approximately match the in-vivo conditions of tear turnover. The content of the drug is determined by HPLC method. The release profile of the drug is evaluated by plotting different graphs: Cumulative drug release (ug) versus time, percentage drug release versus time and release rate (ng/hr) versus hours. The experiments are carried out in triplicate. The diffusion coefficient is measured. If the desired release rate is not achieved, different structures with 3 "barrier layer inks" are created with the 3D Digital Printer and drug release evaluated.
   b. Lens Dimension: Lenses are hydrated and measured for diameter, base curve and corrective power (if any) to determine changes taking place when compared to the same for unprinted control lenses. This step allows that the lens has expanded (swelled) to the same size as a base methafilcon lens.
   c. Water Content: Water content of the lens is measured gravimetrically to evaluate any change in the water content.
   d. Light Transmission: Test is done to evaluate that 3D Digital Printing does not affect percentage of light transmitted through the lens.
   e. Oxygen Permeability: Tests are conducted outside to evaluate this parameter.
   f. The bonding of the 3D printed layers to the lens surface is evaluated by rubbing between fingers at least 50 times to check for adhesion.
   g. Drug equivalency test is conducted to evaluate that the released drug from the contact lens is the same as the drug that is loaded in the ink.
   h. Solvent Extraction Test: The standard solvent extraction test for contact lens is carried out to evaluate if there is anything else, other than the drug, leaching out.
   i. Cytotoxicity study by agar overlay method is done for toxicity testing.
7. Statistical Analysis: Data from drug release studies is presented as means±standard deviations. Test of significant difference between control and drug loaded lenses is carried out using One Way ANOVA and appropriate Student's t-tests.
8. Evaluation Criteria: The following acceptance criteria are used:
   a. Achieve sustained release of at least 7 days for Bimatoprost and HA individually and/or combined.
   b. The drug does not appreciably change structure, function, activity or a combination thereof due to the 3D Digital Printing of the ink on the lens.
   c. The lens integrity being maintained by measuring the lens dimensions, percent water content, oxygen permeability, extractables, and cytotoxicity. There preferably is no statistical significant difference from the control lenses where applicable.
9. Other Considerations: The lenses of the present invention can include a comfort enhancing drug along, a different drug (such but not limited to a glaucoma drug), either alone or in combination. There can be provided a plurality of different comfort enhancing drugs and different drugs, either alone or in combination.

BIBLIOGRAPHY

1. Abelson, Mark "Glaucoma and Dry Eye: A Tough Combo", Article dated: Oct. 4, 2011. Retrieved from http://www.revophth.com/content/d/therapeutic_topics/i/1650/c/30437/2.
2. Glaucoma Research Foundation, "Dry Eyes and Glaucoma: Double Trouble" Retrieved from http://www.glaucoma.org/treatment/dry-eyes-and-glaucoma-double-trouble.php
3. Peng, C. C., Burke, M. T., Carbia, B. E., Plummer, C., & Chauhan, A. (2012). Extended drug delivery by contact lenses for glaucoma therapy. *Journal of Controlled Release*, 162(1), 152-158
4. Kompella, U. B., Kadam, R. S., & Lee, V. H. (2010). Recent advances in ophthalmic drug delivery. *Therapeutic delivery*, 1(3), 435-456.
5. Hui, Alex, "Contact lenses for drug delivery—overview and recent developments", Contact Lens Update, Article dated: Jun. 29, 2012. Retrieved from http://contactlensupdate.com/2012 Jun. 29/contact-lenses-for-drug-delivery-overview-and-recent-developments/
6. Chauhan, Anuj "Ophthalmic Drug Delivery Through Contact Lenses", Contact Lens Spectrum. Article dated: Nov. 1, 2012. Retrieved from http://www.clspectrum.com/articleviewer.aspx?articleID=107608
7. Ciolino, J. B., Hudson, S. P., Mobbs, A. N., Hoare, T. R., Iwata, N. G., Fink, G. R., & Kohane, D. S. (2011). A prototype antifungal contact lens. *Investigative ophthalmology & visual science*, 52(9), 6286-6291.
8. Ciolino, J. B., Hoare, T. R., Iwata, N. G., Behlau, I., Dohlman, C. H., Langer, R., & Kohane, D. S. (2009). A drug-eluting contact lens. *Investigative ophthalmology & visual science,* 50(7), 3346-3352.
9. Ciolino, J., Dohlman, C., & Kohane, D. (2009). Contact Lenses for Drug Delivery. *Seminars in Ophthalmology,* 24(3), 156-160.
10. Gulsen, D., & Chauhan, A. (2004). Ophthalmic Drug Delivery through Contact Lenses. University of Florida, Chemical Engineering Department, Gainesville. Retrieved from www.iovs.org/cgi/content/abstract/45/7/2342
11. SCRIP Business Insights, "The Ophthalmic Pharmaceutical Market Outlook to 2016", Pg. 12.
12. Ciolino, J. B., Stefanescu, C. F., Ross, A. E., Salvador-Culla, B., Cortez, P., Ford, E. M., ... & Kohane, D. S. (2014). <i>In vivo</i> performance of a drug-eluting contact lens to treat glaucoma for a month. *Biomaterials,* 35(1), 432-439.
13. Council, Aaron, and Michael Petch. "*3D Printing: Rise of the Third Industrial Revolution.*"
14. Jha, G., & Kumar, A. (2011). Drug delivery through soft contact lenses: An introduction. *Chronicles of Young Scientists,* 2(1), 3.
15. Than, Tammy P., Chaglasian, Elyse L., "Exploring New Frontiers in Drug Delivery", Review of Cornea & Contact Lenses, Article dated: Nov. 15, 2013. Retrieved from http://www.reviewofcontactlenses.com/content/c/44958/dnnprintmode/true/?skinsrc=%5 B1%5Dskins/rccl2010/pageprint&containersrc=%5B1%5Dcontainers/rccl2010/simple
16. Novack, G. D. (2009). Ophthalmic drug delivery: development and regulatory considerations. *Clinical Pharmacology & Therapeutics,* 85(5).
17. NIH Medline Plus, 2008. "Leading Cause of Blindness", summer 2008 issue, Volume 3 Number 3 pages 14-15.

Example #12

Gelation Agent

The use of 3D Digital and/or other printing technologies that provides drug on surface of the lens for sustained delivery of drug from contact lenses offers many advantages over incorporating drug inside the lens.

The Problem

The existing technological approach can limit the amount of drug that can be added on surface of lens without affecting lens characteristics like its dimensions, oxygen permeability, clinical performance, and the like.

The Present Invention

The present invention allows increase in the availability of drug on ocular surface by increasing the residence time or reducing evaporation rate with in-situ gelatin by releasing a drug and gelation agent from the surface of the lens. Likewise the present invention allows for in-situ molecular imprinting so that patient or subject does not have to remove lens from the eye.

As a non-limiting example, a layer of drug and layer of Gellan gum on the surface of contact lens with 3D Digital Printing and/or other printing technologies can be provided. It is noted that the gelation agent can be included in a wide variety of inks, products during production, and final products of the present invention. An additional layer of solute that provides Ca++ ion can be provided. When Gellan Gum comes in contact with Ca++ ion, it gels. Thus, the rate of evaporation or washout of drug in tear can be reduced. This can increase residence time of drug that can result in increased bioavailability.

Example #13

Penetration Enhancing Agent

An additional aspect of the present invention is that it allows for drug delivering in the posterior chamber of eye by simultaneously releasing drug and penetration enhancing from surface of a contact lens of the present invention. When delivered topically, ocular drugs often suffer poor bioavailability. This is due to the various barriers and mechanisms that keep the drug from reaching the target site such as static barriers, dynamic barriers, and efflux pumps. Static barriers include the different layers of the cornea, sclera and retina including blood aqueous and blood-retinal barriers. Dynamic barriers include the choroidal and conjunctival blood flow, lymphatic clearance, and tear dilution. In order to overcome this problem, penetration enhancers are released from the lens at the same time as the drug over a period of time, simultaneously, separately or one after other, in order to improve the amount of drug that is able to reach the target site. The present invention thus avoids the problems associated with current invasive technique like injection of drug or surgically implants of plugs, etc.

In order to provide drug in the posterior of eye, one can provide in association with a lens a layer of penetrating enhancer such as, for example, Flurbiprofen, Acetazolamide, ethylenediaminetetraacetic acid, palmitoyl carnitine, sodium caprate, sodium dodecylsulphate, sodium deoxycholate, poly oxyethylene-g-lauryl ether, 1-α-lysophosphatidylocholine, deoxycholate, taurodeoxycholate, glycocholate, or benzalkonium chloride. Other penetration enhancing agents that are known in the art or later developed are part of the present invention.

In order to provide drug in the posterior of eye, one can provide in association with a lens a layer of penetrating enhancer like Flurbiprofen or Acetazolamide. Another layer of drug like eylea for dry eye, neovascular Age-Related Macular Degeneration (wet AMD), or dry Age-Related Macular Degeneration (dry AMD) can be provided. Further, drugs for diabetic retinopathy can be delivered to the posterior of the eye using, for example, sustained delivery of one or more penetration enhancers with drugs for diabetic retinopathy. Sustained delivery of the penetration enhancer can facilitate delivery of a drug for AMD (wet and dry macular degeneration), diabetic retinopathy, or other diseases, disorders, or conditions that can impact the posterior of eye.

Example #14

Drug Delivery Micro Structures

Polymeric Nanoparticles, Liposomes, Niosomes, Discomes, Ethosomes, Microspheres, Solid Lipid Nanoparticles, Micells, Microemulsions, Nanocrystals, Dendrimers, Microsphonesor a Combination Thereof The inks, medical devices/contact lenses during production, and final products can utilize a variety of micro structures in order to encapsulate or otherwise produce structures that can modulate drug release from a coating of the present invention. In some instances a drug is within such a micro structure, in the bulk solution, or a combination thereof. A variety of such microstructures are available in the art and are adaptable to the present invention in the materials and methods utilized, including ink formulations, to produce a medical device such as a contact lens of the present invention. The following is an exemplary list that is not comprehensive of such micro structures that are useful in the present invention.

a. Polymeric nanoparticles (Biodegradation, non-biodegradables, temperature sensitive, pH sensitive, ion sensitive, magnetic sensitive, electric sensitive, light sensitive).
b. Liposomes
c. Niosomes
d. Discomes
e. Ethosome
f. Microspheres
g. Solid Lipid Nanoparticles
h. Micells
i. Microemulsion
j. Nanocrystals
k. Dendrimers
l. Microsponges
m. or a combination thereof.

a. Polymeric nanoparticles

These structures can be used in the present invention and include, for example, Biodegradable materials, such as but not limited to temperature sensitive, pH sensitive, ion sensitive, Magnetic-sensitive, Electric-sensitive) materials. Non-biodegradable materials can be used as well.

b. Liposome

A liposome is an artificially prepared vesicle composed of a lipid bilayer. The liposome can be used as a vehicle for administration of nutrients and pharmaceutical drugs. Liposomes can be prepared by disrupting biological membranes (such as by sonication). Liposomes are often composed of phosphatidylcholine enriched phospholipids and can also contain mixed lipid chains with surfactant properties such as egg phosphatidylethanolamine. The major types of liposomes are the multilamellar vesicle (MLV), the small unilamellar vesicle (SUV), the large unilamellar vesicle (LUV), and the cochleate vesicle. Liposomes should not be confused with micelles and reverse micelles composed of monolayers. A liposome encapsulates a region of aqueous solution inside a hydrophobic membrane; dissolved hydrophilic solutes cannot readily pass through the lipids. Hydrophobic chemicals can be dissolved into the membrane, and in this way liposome can carry both hydrophobic molecules and hydrophilic molecules. To deliver the molecules to sites of action, the lipid bilayer can fuse with other bilayers such as the cell membrane, thus delivering the liposome contents.

c. Niosome

A niosome is a non-ionic surfactant-based liposome. Niosomes are formed mostly by cholesterol incorporation as an excipient. Niosomes have more penetrating capability than the emulsions. They are structurally similar to liposomes in having a bilayer, however, the materials used to prepare niosomes make them more stable and thus niosomes offer many more advantages over liposomes. Niosomes are lamellar structures that are microscopic in size. They constitute of non-ionic surfactant of the alkyl or dialkyl polyglycerol ether class and cholesterol with subsequent hydration in aqueous media. The surfactant molecules tend to orient themselves in such a way that the hydrophilic ends of the non-ionic surfactant point outwards, while the hydrophobic ends face each other to form the bilayer. The figure in this article on Niosomes gives a better idea of the lamellar orientation of the surfactant molecules.

d. Discomes

A non-conventional form of niosomes called discomes formed with incorporation of poly-24-oxyehtylene cholesteryl ether or so called Solulan C24. Discomes are giant (approximately 20 μm in diameter), disc-shaped niosomes that coexisted with conventional spherical niosomes (2-5 μm). Discomes were believed to offer several advantages over conventional niosomes, such as better fit in the cul-de-sac of the eye and improved ocular drug bioavailability due to slower nasolacrimal.

e. Ethosomes

Ethosomes are lipid vesicles containing phospholipids, alcohol (ethanol and isopropyl alcohol) in relatively high concentration and water. Ethosomes are soft vesicles made of phospholipids and ethanol (in higher quantity) and water. Ethosomes can entrap drug molecule with various physicochemical characteristics i.e. of hydrophilic, lipophilic, or amphiphilic. The size range of ethosomes can vary from nanometers to microns.

f. Microspheres

Microspheres are small spherical particles, with diameters in the micrometer range (typically 1 μm to 1000 μm (1 mm)). Microspheres are sometimes referred to as microparticles. Microspheres can be manufactured from various natural and synthetic materials. Glass microspheres, polymer microspheres and ceramic microspheres are commercially available. Microspheres have numerous applications depending on what material they are constructed of and what size they are. Polyethylene, polystyrene and expandable microspheres are the most common types of polymer microspheres. Drug loaded microspheric particles, can sustain the release of drug, where biodegradable or non biodegradable polymers are used.

g. Solid Lipid Nanoparticle

Solid lipid nanoparticles (SLN) are a new pharmaceutical delivery system or pharmaceutical formulation. A solid lipid nanoparticle is typically spherical with an average diameter between 10 to 1000 nanometers. Solid lipid nanoparticles possess a solid lipid core matrix that can solubilize lipophilic molecules. The lipid core is stabilized by surfactants (emulsifiers). The term lipid is used here in a broader sense and includes triglycerides (e.g. tristearin), diglycerides (e.g. glycerol bahenate), mono glycerides (e.g. glycerol mono stearate), fatty acids (e.g. stearic acid), steroids(e.g. cholesterol), and waxes (e.g. cetyl palmitate). All classes of emulsifiers (with respect to charge and molecular weight) have been used to stabilize the lipid dispersion. It has been found that the combination of emulsifiers might prevent particle agglomeration more efficiently. Development of solid lipid nanoparticles is one of the emerging fields of lipid nanotechnology with several potential applications in drug delivery, clinical medicine and research, as well as in other discipline. Due to their unique size-dependent properties, lipid nanoparticles offer the possibility to develop new therapeutics. The ability to incorporate drugs into nanocarriers offers a new prototype in drug delivery that could hold great promise for attaining the bioavailability enhancement along with controlled and site specific drug delivery. It has been proposed that SLNs combine numerous advantages over the other colloidal carriers i.e. incorporation of lipophilic and hydrophilic drugs feasible, no bio-toxicity of the carrier, avoidance of organic solvents, possibility of controlled drug release and drug targeting, increased drug stability and no problems with respect to large scale production.

h. Micelles

Polymeric micelles. They are prepared from certain amphiphilic co-polymers consisting of both hydrophilic and hydrophobic monomer units. They can be used to carry drugs that have poor solubility. This method offers little in the terms of size control or function malleability. Techniques that utilize reactive polymers along with a hydrophobic additive to produce a larger micelle that create a range of sizes have been developed. A micelle (micelles, micella, or micellae) is an aggregate of surfactant molecules dispersed in a liquid colloid. A typical micelle in aqueous solution forms an aggregate with the hydrophilic "head" regions in contact with surrounding solvent, sequestering the hydrophobic single-tail regions in the micelle center. This phase is caused by the packing behavior of single-tailed lipids in a bilayer. The difficulty filling all the volume of the interior of a bilayer, while accommodating the area per head group forced on the molecule by the hydration of the lipid head group, leads to the formation of the micelle. This type of micelle is known as a normal-phase micelle (oil-in-water micelle). Inverse micelles have the head groups at the centre with the tails extending out (water-in-oil micelle). Micelles are approximately spherical in shape. Other phases, including shapes such as ellipsoids, cylinders, and bilayers, are also possible. The shape and size of a micelle are a function of the molecular geometry of its surfactant molecules and solution conditions such as surfactant concentration, temperature, pH, and ionic strength. The process of forming micelles is known as micellisation and forms part of the Phase behavior of many lipids according to their polymorphism.

i. Microemulsions

Microemulsions are clear, thermodynamically stable, isotropic liquid mixtures of oil, water and surfactant, frequently in combination with a cosurfactant. The aqueous phase can contain salt(s) and/or other ingredients, and the "oil" can actually be a complex mixture of different hydrocarbons and olefins. Dispersion made of water, oil, and surfactant(s) that is an isotropic and thermodynamically stable system with dispersed domain diameter varying approximately from 1 to 100 nm, usually 10 to 50 nm. In contrast to ordinary emulsions, microemulsions form upon simple mixing of the components and do not require the high shear conditions generally used in the formation of ordinary emulsions. In ternary systems such as microemulsions, where two immiscible phases (water and "oil") are present with a surfactant, the surfactant molecules can form a monolayer at the interface between the oil and water, with the hydrophobic tails of the surfactant molecules dissolved in the oil phase and the hydrophilic head groups in the aqueous phase.

j. Dendrimers

Dendrimers are also polymer-based delivery vehicles. They have a core that branches out in regular intervals to form a small, spherical, and very dense nanocarrier. Dendrimers are repetitively branched molecules. Synonymous terms for dendrimer include arborols and cascade molecules. However, dendrimer is currently the internationally accepted term. A dendrimer is typically symmetric around the core, and often adopts a spherical three-dimensional morphology. The word dendron is also encountered frequently. A dendron usually contains a single chemically addressable group called the focal point. The difference between dendrons and dendrimers is illustrated in figure, but the terms are typically encountered interchangeably.

Example #15

Biodegradable Polymers

Biodegradable polymers are polymers that break down and lose their initial integrity inside the body. Biodegradable polymers are used in medical devices to avoid a second operation to remove them (Biodegradable sutures), or to gradually release a drug. The polymer slowly degrades into smaller fragments, releasing entrapped drug in a control manner. The drug slowly releases as polymer degrades with time. Biodegradable polymers are non-toxic, FDA approved and capable of maintaining good mechanical integrity until degraded, and capable of controlled rates of degradation. A goal is to control the rate at which water can get into polymers. Factors controlling the rate of degradation include: percent crystallinity, molecular weight, and hydrophobicity.

These materials can be used in the present invention and include, for example, polyester is a class of polymers characterized by ester linkages in the backbone, such as poly (lactic acid) (PLA), poly(glycolic acid) (PGA), poly(lactide-co-glycolide) (PLGA), etc. Polyanhydrides are a group of surface-erosion dominated biodegradable materials, such as but not limited to: polyanhydride (poly(fatty acid dimer-sebacic acid), polycaprolactone, poly-3-hydroxybutyrate, poly(trimethylene carbonate) copolymers, poly(dioxanone), etc., polyorthoesters, polyphosphazenes.

Example #16 pH Sensitive Polymers

These materials can be used in the present invention and include, for example, pH sensitive polymers: poly(ortho ester amides) copolymer, the degradation of which is triggered by acids, Poly(acrylic acid)-g-PEG, PEG-b-poly(L-histidine), etc. Also, chitosan (thermosensitive, polycationic polymer, pH exceeding 6.2 leads to the formation of a hydrated gel like precipitate). In addition, carbopol is a well known pH dependent polymer, which stays in solution form at acidic pH but forms a low viscosity gel at alkaline pH Example #17

Thermosensitive Polymer

Thermosensitive polymer (TSP), such as poly(N-isopropylacrylamide), which exhibited a lower critical solution temperature (LCST) and aggregated at temperatures above the LCST due to hydrophobic interactions. These TSP-modified formulations released an encapsulated drug above the LCST.

These materials can be used in the present invention and include, for example, Block copolymers of poly(ethylene glycol)/poly(lactic-coglycolic acid) (PEG/PLGA, ReGel®) and poly(ethylene oxide)/poly(propylene oxide) (PEO/PPO, Pluronic®) have also thermo-sensitivity. Also, xyloglucan (composed of a (1-4)-β-D-glucan backbone chain, which has (1-6)-α-D xylose branches that are partially substituted by (1-2)-β-D-galactoxylose)

Example #18

Ultrasound-Mediated Drug Release

Ultrasound-mediated drug release: These materials can be used in the present invention and include, for example, a copolymer of N-isopropylmethacrylamide (NIPMAM) and N-isopropylacrylamide (NIPAM) encapsulated drug, releases drug on ultrasound irradiation. Polyanhydride, polyglycolide, polylactide, and poly(hydroxyethyl methacrylate-co-N,N'-dimethylaminoethyl methacrylate).

Example #19

Magnetic Field Responding Polymers

These materials can be used in the present invention and include, for example, magnetic field responding polymer poly(ethylene-co-vinylacetate).

Example #20

Light Sensitive Polymers

Light sensitive polymers: These materials can be used in the present invention and include, for example, poly(N,N-dimethylacrylamide-co-4-phenyl-azophenyl acrylate) and poly(N,N-dimethyl acrylamide-co-4-phnyl-azophenyl acrylamide). Also, Photopolymerizable, biodegradable hydrogel: Macromer (PEG-oligoglycolyl-acrylate), a photosensitive initiator (eosin dye) and a light source (UV or visible light). When exposed to light, the system undergoes photopolymerization to form a network.

Example #21

Electricity Sensitive Polymers

These materials can be used in the present invention and include, for example, poly(ethylenediamine-co-1,10-bis (chloro-carbonyl)decane), polyethyloxazoline/poly(methacylate).

Example #22

Mechanical Stress Sensitive Polymers

These materials can be used in the present invention and include, for example, dihydrazide-crosslinked polyguluronate, poly(methyl methacrylate)/poly(vinyl alcohol) or/cellulose ether.

Example #23

Ionic Strength (Ion Sensitive Polymers)

These materials can be used in the present invention and include, for example, poly(NIPAAm-co-benzo-18-crown (60-acrylamide). Also, gellan gum (anionic deacetylated exocellular polysaccharide, commercially available as Gelrite™ or Kelcogel™, gelation which is temperature dependent or cations induced). In addition, Pectin (gels in the presence of $H^+$ ions), alginic acid (gels on addition of di- and trivalent metal ions), low methoxypectins (comprises α-(1-4)-D-galacturonic acid residues, readily form gels in aqueous solution in the presence of calcium ions).

Example #24

Non-Degradable Polymers

These materials can be used in the present invention and include, for example, polymers that exhibit no to very low degradation in aqueous and biological environments, acting as an inert matrix structure for sustain drug release via diffusion. Poly(ethylene) (PE), Poly(propylene) (PP), Poly (tetrafluroethylene) (PTFE) (Teflon), Poly(methymethacrylate), Ethylene-co-vinylacetate (EVA), Poly(dimethylsiloxane) (PDMS), Low MW poly(dimethylsiloxane), Poly (ether-urethanes) (PU), Poly(ethylene terphthalate) (PET), Poly(sulphone) (PS), Poly(ethyleneoxide) Poly(ethyleneoxide-copropyleneoxide) (PEO-PPO), Poly(vinylalcohol), etc.

Example #25

Sustained or Pulsating Release of Drug Using Smart/Biodegradable Polymer

The present invention includes the case where drug loaded nanoparticles/nanospheres prepared using smart polymers (including stimuli sensitive) are incorporated in the ink. Smart polymers include but are not limited to temperature sensitive, pH sensitive, pressure sensitive, ion sensitive, magnetic sensitive, electric-sensitive; or a combination thereof.

Example: Drug loaded nanoparticles prepared using temperature sensitive polymer, which is not biodegraded below 34° C. When the therapeutic contact lens (as a medical device) is inserted on an eye ball, the temperature rises to or above 34° C., which cause polymer to degrade and release the entrapped drug from nanoparticles. Similarly when patient is suffering from conjunctivitis or other eye diseases, temperature rise can modulate the drug to release. Polymers, which become insoluble upon heating, have a so-called lower critical solution temperature (LCST). Systems, which become soluble upon heating, have an upper critical solution temperature (UCST). UCST system is based on a combination of acrylamide (AAm) and acrylic acid (AAc). PEO-b-PPO block copolymers, PEO-b-PPO-b-PEO and PEG-b-PLGA-b-PEG.

Example: Drug loaded nanoparticles prepared using pH sensitive polymer (e.g. poly(l,4-phenyleneacetone dimethylene ketal), which is not biodegraded at pH above 8. When the therapeutic contact lens (as a medical devise) is inserted on an eye ball, the pH of tear fluid is 7.4, which cause polymer to degrade and release the entrapped drug from nanoparticles. Similarly when patient is suffering from conjunctivitis or other eye diseases, pH is more towards acidic side, cause higher degradation to release drug from nanoparticles. So modulation of drug release is possible using different pH sensitive polymers.

Thermosensitive biodegradable multiblock copolymers: Acid-labile acetal linkages were synthesized from Pluronic® triblock copolymers (Pluronic® P85 and P104) and di-(ethylene glycol) divinyl ether.

Thermosensitive biodegradable Diblock copolymers: Diblock polymer backbone where the first block is a copolymer of pH-sensitive ethyl acrylic acid (EAA) monomers and hydrophobic butyl methacrylate (BMA) or hexyl methacrylate monomers. The second block is a homopolymer of N-acryloxy succinimide (NASI) or ß-benzyl L-aspartate N-carboxy-anhydride (BLA-NCA) monomers. These comb-like polymers degraded into small fragments upon incubation in an acidic solution (pH 5.8) due to hydrolysis of the hydrazone linkages connecting the hydrophobic/cationic grafts to the polymer backbone.

Poly(ethylene glycol)-cis-aconityl-chitosan-stearic acid (acid-triggered PEG degradation)

Poly(ethylene glycol)-poly(D,L-lactic acid)-poly (β-amino ester) (PEG-(PLA-PAE))

Example #26

In-Situ Molecular Imprinting

Another aspect of the present invention generally relates to the use of in situ molecular imprinting to significantly increase the amount of time an ocular drug can be delivered via contact lenses wherein the in situ molecular imprinting allows for sustained release and replenishing of said drugs or comfort enhancing agent onto the contact lens, thus increasing release time without removal of the lens from the eye.

In-Situ molecular imprinting can be achieved by swelling lens in eye to allow easy impregnation of drug in the lens. Swelling agents like alcohol can be used.

Example #27

Sustained Delivery of Hyaluronic Acid (HA) that is Digitally Printed on the Surface of a Methafilcon Lens A. Preparation of Inkjettable Ink—Preparation of an Ink with an Oligomer Capable of Free Radical Polymerization for Use in Printable Formulations 1. A Polyhydroxyethylmethacrylate prepolymer is prepared according to the following procedure. The following components are mixed:

| Material | % |
|---|---|
| Methacrylic acid | 0.82% |
| Mercaptoethanol | 0.70% |
| Allyl methacrylate | 0.16% |
| Ethyl triglycol methacrylate | 3.50% |
| N-Vinyl pyrrolidinone | 6.07% |
| 2-Hydrozyethyl methacrylate | 35.42% |
| Vazo 64 | 0.33% |
| 1-Ethoxy-2-propanol | 44.80% |
| 1-Methoxy-2-proply acetate | 8.21% |
| TOTAL | 100.00% |

Thermal polymerization is carried out in a steel can fitted with an over-head stirrer and mounted on a hot plate. The mixture is heated and temperature of the mixture is maintained at about 85° C. to about 90° C. by moving the can/stirrer assembly between cold water bath and the hot plate as necessary. The reaction is allowed to continue for about 37 minutes from initially reaching 85° C. prior to quenching polymerization by placing the can/stirrer assembly into the cold water bath. The cold prepolymer viscosity is checked and stored in a refrigerator. A typical viscosity of the prepolymer is about 2,000 cp to about 3,000 cp.

2. Derivatization of Prepolymer is Carried out as Follows to Make an Ink

To a solution of 20 grams of the Polyhydroxy ethyl methacrylate prepolymer with a viscosity of 500 to 50,000 cP in solvent 1-methoxy-2-propanol is added 0.2 grams of triethyl amine and stirred well with a magnetic stir bar for 10 to 60 minutes. 1 to 5 grams of methacryloyl chloride solution, 1 to 20% in 1-methoxy-2-propanol, is added while stirring at room temperature. The reaction mixture is stirred overnight thus creating a prepolymer derivative, or an alpha beta unsaturated oligomer as an ink.

It is noted that derivatized oligomer for polyvinyl alcohol, glycidol methacrylate, silicone, n-n-dimethylacrylamide can be prepared similarly to facilitate free radical polymerization with these polymers.

3. Loading of HA in an Ink (Direct Loading)

Required amount of HA was directly added in an ink, followed by sonication for 15 minutes, thus providing HA in a polymer matrix.

In case of HA, which was HEMA monomer ink insoluble, its particulate form (without processing) is loaded in ink along with Tween 20, followed by sonication for 5 to 60 minutes.

Formulation

| Drug | Hyaluronic Acid (HA) |
|---|---|
| Methodology | Direct HA loading |
| State of HA in ink | Solid particles |
| % of drug loading | 2% |
| Amount of Tween 20 | 2% |
| Irgacure 1800 | 3.5% |
| Irgacure 819 | 1.5% |
| Ink | up to 100% |

The following table provides results of ink testing.

| Drug | Methodology | Viscosity (c.p.) | EST (mN/m) | Particle/globule size (nm) | pH |
|---|---|---|---|---|---|
| Hyaluronic Acid (RA) | Direct HA loading | 12.6 | 36.03 | 1227 | 6 |

4. Formulation for a Barrier Layer

| Material | Formulation |
|---|---|
| LLT Oligomer | 1-50% |
| SR 344 (PEG 400 Diacrylate) | 0.1-20% |
| 1-Vinyl-2-pyrrolidinone (NVP) | 1-50% |
| Ethoxytriethylene Glycol Methacrylate | 1-50% |
| 2-Hydroxyethyl methacrylate (HEMA) | 1-75% |

Properties of a barrier layer

| Surface Tension | 15-40 dynes/cm |
|---|---|
| Viscosity | 0.1-35 centipoise |

5. 3D Digital Printing

Above ink then was supplied to a prototype 3D printer that uses a piezzo Xarr Printer head XJ 126. A desired details of digital printed image was then inkjet printed. After each layer the image was cured under fusion UV type D bulb for 45 second. A second layer was then printed and cured similarly. With the curing of each layer, a polymer matrix is created that can essentially match the properties of the base polymer of the lens (which need not be the case) and also entraps the drug and/or HA. Multiple layers can be printed until the desired delivery rate is attained.

6. Flux Study (In-Vitro for Drug Delivery Rate): Calibration Curve of Hyaluronic Acid using Spectroscopic Method A. Preparation of Hyaluronic Acid Solution (Solution 1):

Accurately weighed (25 mg) hyaluronic acid was transferred to 25 ml volumetric flask and volume was made up to the mark with double distilled water (1 mg/ml solution). From the above solution, 5 ml of solution was withdrawn accurately with the help of pipette and transferred to 50 ml volumetric flask. Volume was made up to the mark with double distilled water to make stock solution (100 µg/ml). From the stock solution of HA, different aliquots were accurately withdrawn with the help of pipette and transferred to separate volumetric flasks and the volume was made up to the mark with double distilled water to give final concentration of 0.15, 0.3, 0.45, 0.6, 0.75, 0.9 and 1.05 µg/ml.

B. Preparation of Stain All Dye Solution (Solution 2):

The Stain All is a known dye which binds glycosaminoglycans and forms complexes whose optical properties are different from those of the free dye. The solution of the dye was prepared by dissolving 10 mg of Stain All in 8 ml of double distilled water and 2 ml of methanol, to give 1 mg/ml concentration. From the above solution, 0.3 ml of solution was withdrawn accurately with the help of pipette and transferred to 10 ml volumetric flask. Volume was made up to the mark with double distilled water to make stock solution (30 µg/ml).

Figure 13:
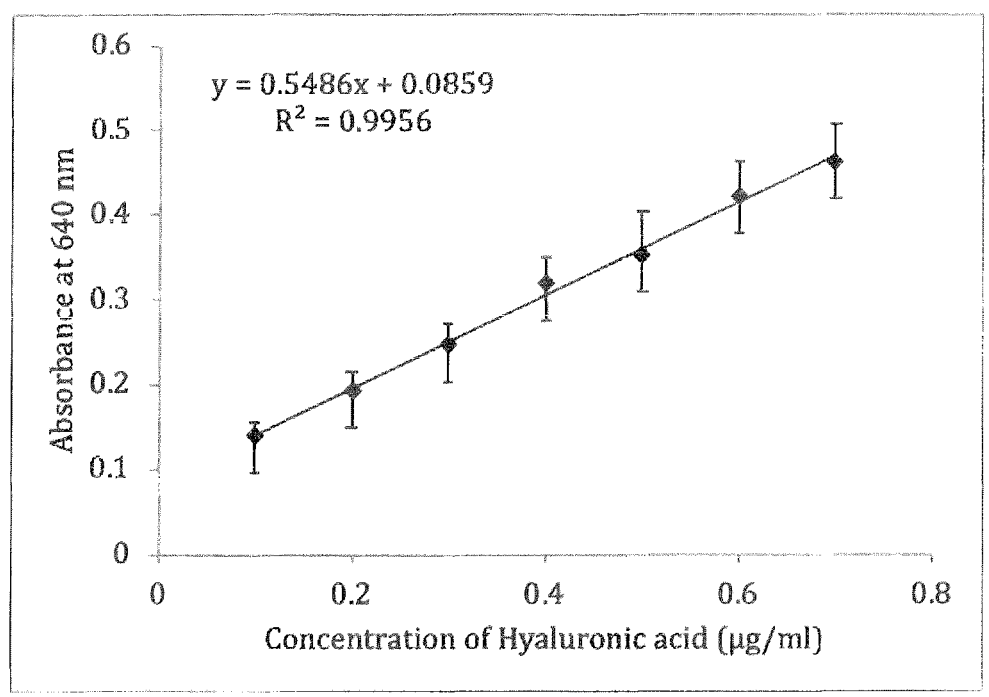
FIG. 13 depicts the Calibration curve of hyaluronic acid (HA) by spectroscopic method at 640 nm.

C. Preparation of Calibration Curve:

Two (2) ml of Solution 1 and 1 ml of solution 2, was mixed in a test tube to give 10 µg/ml of all stain dye and final concentrations of HA (0.1 to 0.7 µg/ml), as shown in table 3, column 3. The absorbance of the resulting blue colour complex (HA-dye) solutions was measured at 640 nm against double distilled water. Calibration curve was prepared by plotting absorbance on Y-axis and respective concentration on X-axis (FIG. 13). The readings were recorded in triplicate. The table below showed the mean absorbance values of the drug along with the standard deviation values. The value of regression coefficient ($R^2$=0.995) in double distilled water indicate that the absorbance and concentration of drug are linearly related and obeys Beer Lambert's law at selected HA concentration range.

Calibration curve of Hyaluronic acid by spectroscopic method at 640 nm.

| Solution 1 of HA (µg/ml) | Solution 2 of All Stain dye (µg/ml) | Final concentration of HA (µg/ml) | mAUC (Mean ± SD, n = 3) |
| --- | --- | --- | --- |
| 0.15 | 30 | 0.1 | 0.139 ± 0.0153 |
| 0.3 | 30 | 0.2 | 0.193 ± 0.0217 |
| 0.45 | 30 | 0.3 | 0.247 ± 0.024 |
| 0.6 | 30 | 0.4 | 0.319 ± 0.0308 |
| 0.75 | 30 | 0.5 | 0.354 ± 0.0512 |
| 0.9 | 30 | 0.6 | 0.423 ± 0.0397 |
| 1.05 | 30 | 0.7 | 0.462 ± 0.0439 |

D. Flux Study (In Vitro Release Study) in Simulated Tear Fluid was Conducted as Follows.

The printed contact lenses were placed in 2 ml of simulated tear fluid in glass vial (20 ml capacity) at 34° C. in incubator with shaker at 100 RPM. The volume of the release medium was chosen to be 2 ml to approximately match the in vivo conditions of tear turnover. The simulated tear fluid was replaced at every interval with the same volume of fresh stimulated tear fluid, to maintain perfect sink condition. The content of drug was determined by HPLC assay at 295 nm after suitable dilution.

Figure 14:
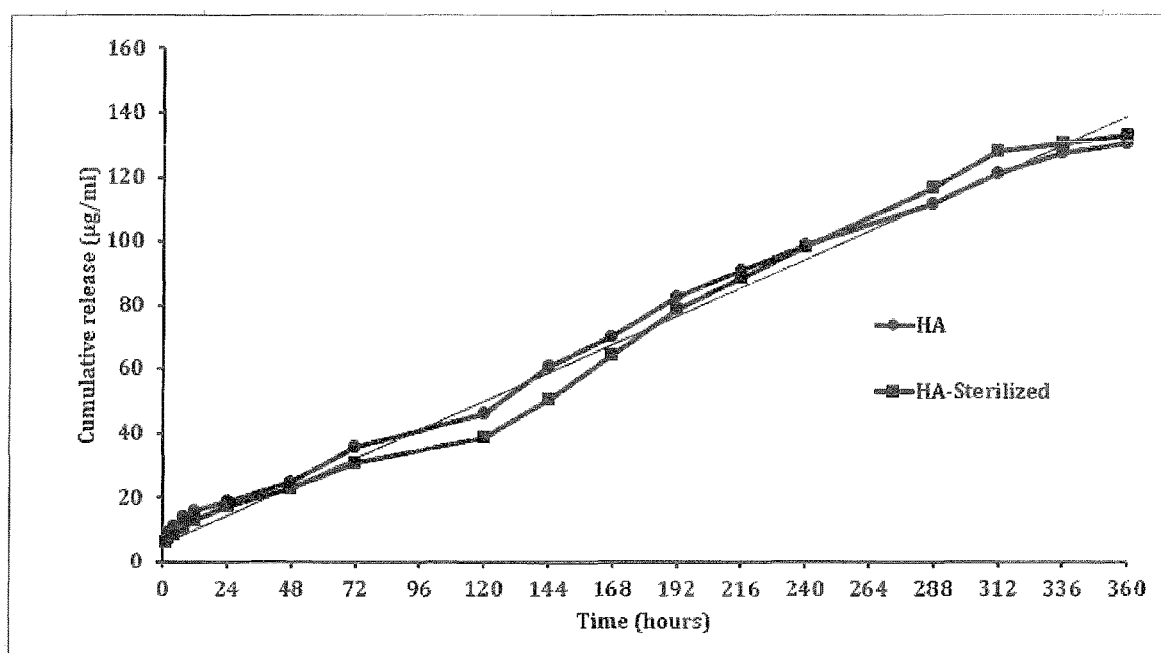
FIG. 14 depicts the cumulative drug release rate of HA with time from a contact lens having HA printed on the surface of the lens.
Figure 15:
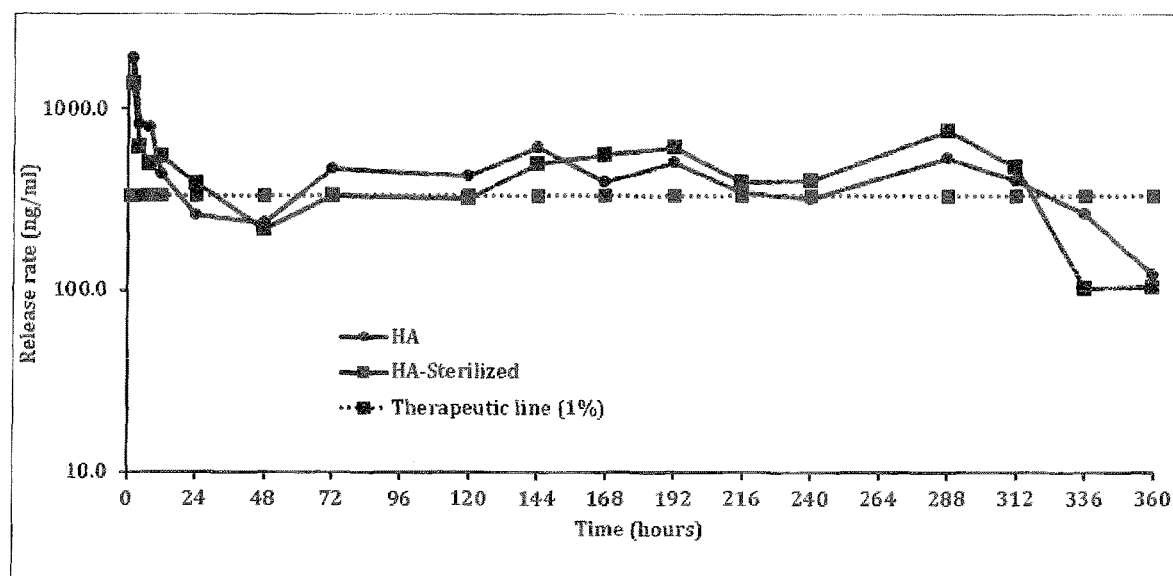
FIG. 15 depicts Release rate of HA with time from a contact lens having HA printed on the surface of the lens.

Such studies were carried out with steam sterilized lens as well as un-hydrated (unsterilized dry) lens. The results are depicted in FIG. 14 and FIG. 15.

From these results it is evident that sustained drug release of HA for more than 10 days was achieved. Also zero order kinetics was achieved with sterilized and unsterilized dry lenses. Kinetic modeling on drug release done per method suggested by Dash et al. (Dash, S., P. N. Murthy, et al. (2010). "Kinetic modeling on drug release from controlled drug delivery systems." Acta Pol Pharm 67(3): 217-223.) gave $R^2$ as 0.988, slope=0.27, which is less than 0.5, indicating zero order release. Also there was no significant difference observed in the drug release rate of sterilized and unsterilized lens.

Example #28

Additional Examples of Drug Delivery Contact Lenses—A Contact Lens Including HA

One aspect of the present invention includes a contact lens that comprises hyaluronic acid (HA) as a comfort enhancing agent/drug that can release said HA from its surface, including:

a) a base contact lens; and b) said contact lens including HA;

wherein the Molecular weight of said HA is from between about 5,000 Daltons and about 4 million Daltons, preferably between about 10,000 Daltons and about 2 million Daltons, more preferably between about 20,000 Daltons and about 1 million Daltons, and more preferably between about 50,000 Daltons and about 500,000 Daltons;

further wherein bulk density of said HA between about 0.03 g/ml and about 0.15 g/ml, and preferably between about 0.05 g/ml and about 0.10 g/ml;

further wherein said HA is incorporated into polymer matrix as a spray dried particle of size from less than about 1 microns and about 50 microns in diameter, preferably between about 2 microns and about 20 microns in diameter, and more preferably between about 5 microns and about 10 microns in diameter;

further wherein said HA is coated on the surface of contact lenses in one or more layers using inkjet printing;

further wherein said contact lens when hydrated is in packaging solution with between about 0.01% and about 5% HA, preferably between about 0.1% and about 3% HA, more preferably between about 1% and about 2% HA;

further wherein said contact lens when hydrated is in a packaging solution having a pH between about 6.5 and 7.8;

further wherein said HA can be released in a therapeutically effective amount for up to between about 5 hours to up to about 45 days, preferably between about 10 hours and about 20 days, more preferably between about 20 hours and about 10 days, and more preferably between about 4 hours and about 5 days.

Another aspect of the present invention includes any article of manufacture, method of making same, or method of using the same where the drug or medicament is a comfort enhancing substance, including HA.

Example #29

Contact Lens for Treatment of Myopia

Field of the Invention

The present invention in part relates in general to the field of medical devices and associated methods to treat, prevent, reduce the severity, and/or slow the progression of myopia.

Background

Myopia, also known as nearsightedness, is a physical disorder of the eye that results in the function of poor eyesight. Generally, the disorder is characterized by the eyeball being too long so that images focused by the lens of the eye do not focus on the retina, but rather before the retina. Due to the incorrect focusing of images, subjects with myopia have poor distance vision (https://nei.nih.gov/health/errors/myopia). Myopia can develop gradually or rapidly, often worsening during childhood and adolescence.

More specifically, myopia occurs as a result of a mismatch between the refractive and axial components of the eye. Optical blur on the peripheral retina is used as a feedback mechanism to govern optical growth, whereas hyperopic blur stimulates excessive ocular growth while myopic blur stimulates the opposite. As myopia can be the result of a misshapen eyeball, the disorder can have its root cause in eye growth. In developmental biology, eye growth is regulated by a homeostatic process in which all optical elements grow to match the length of the eye without significant accommodation (Kang, Pauline. "Optical and pharmacological strategies of myopia control." *Clinical and Experimental Optometry* (2018)). Interruption of this highly coordinated growth results in refractive error (Flitcroft D I. Is myopia a failure of homeostasis? Exp Eye Res 2013; 114: 16-24) (Wallman J, Winawer J. Homeostasis of eye growth and the question of myopia. Neuron 2004; 43: 447-468).

Myopia is a growing epidemic. Studies have shown that myopia prevalence has skyrocketed since the 1970's, with 42% of the U.S. population now suffering some form of myopia (47% in China, 62% in Hong Kong, 53% Singapore) (http://www.aaojournal org/article/S0161-6420(16)00025-7/abstract). Other studies have estimated the prevalence of myopia worldwide in 2000 and predicted the prevalence in 2050. These studies (estimated 22.9% of the world population in 2000 had myopia, and 2.7% had high myopia (http://www.aaojournal.org/article/S0161-6420(16)00025-7/abstract). By 2050, it is estimated that 49.8% of the world population will have myopia, and 9.8% of the world population will have high myopia. (https://nei.nih.gov/health/errors/myopia). The current goal of treatment is to control myopia progression is to reduce the cases of highly myopic adults, as high myopia increases the risk of cataract and glaucoma, conditions with can lead to vision loss. Myopia could be the leading cause of blindness by 2050.

Currently, there are four main treatment options to help control the progression of myopia in children. They are (1) the use of multifocal glasses or contact lenses, (2) the use of orthokeratology lenses, or (3) the use of atropine drops. Recently, there have been some studies on treatment combining options (1) or (2) with option (3) (Shih, Yung-Fang et al., "An intervention trial on efficacy of atropine and multi-focal glasses in controlling myopic progressions," Acta Opthamologica, 79.3 (2001) 233-236).

Currently, the most common treatment option for myopia in children is the use of multifocal contact lenses or glasses for myopia control. Existing multifocal contact lenses or glasses that have been used to treat myopia utilize the homeostatic developmental process of the eye by apparently causing a myopic blur in the peripheral retina, while correctly focusing the images on the central retina, in order to combat the progression of myopia, while also correcting vision.

However, the current mode of changing multifocal contact lens everyday becomes a potentially cumbersome, demotivating problem for young children who have difficulty handling and inserting a contact lens every day. If the lenses could be worn for an extended period, it would improve the chance of its adoption by children. Another issue with these lenses is ensuring that children abide by the cleaning schedule required if the lenses are not disposable. Multifocal glasses are also used, but the trend is to move away from glasses due to the social stigma for children.

Other contact lenses used as treatment to control the progression of myopia are orthokeratology lens (Ortho-k). Ortho-k lens are lenses that patients wear every day during the evening to reshape the cornea of the eye. Again, children face the issue of removal and insertion of a contact lens every day. These lenses are generally hard contact lenses, thus causing a potential issue with comfort in wearing the orthokeratology contact lenses for a prolonged amount of time.

Other treatments to slow the progression of myopia include using eye drops of atropine, usually in a daily regime. The most commonly used dose is a 0.01% atropine solution, which is apparently prescribed for off-label use. Clinical studies have confirmed 0.01% atropine's ability to control the progress of myopia, with limited side effects and few, if any, toxicity concerns. However, the studies have shown that the discontinuation of atropine treatment in some cases lead to a rebound of myopia progression, causing the return of myopia and the progression of myopia in the subject. In addition, the conventional issues with the use of eye drops, such as low bioavailability, side effects from the overall formulation, such as by the presence of preservatives and other components, relatively high concentrations of atropine, and non-compliance to the prescribed regiment are still present with this treatment option.

Atropine has been shown to control myopia progression (Chua, Wei-Han, et al. "Atropine for the treatment of childhood myopia." *Ophthalmology* 113.12 (2006): 2285-2291) (McBrien, Neville A., H. O. Moghaddam, and A. P. Reeder. "Atropine reduces experimental myopia and eye enlargement via a nonaccommodative mechanism." *Investigative ophthalmology & visual science* 34.1 (1993): 205-215) (Chia, Audrey, et al. "Atropine for the treatment of childhood myopia: safety and efficacy of 0.5%, 0.1%, and 0.01% doses (Atropine for the Treatment of Myopia 2)." *Ophthalmology* 119.2 (2012): 347-354). Low doses of atropine (0.01%) have been shown to be effective in controlling myopia progression while also causing minimal side effects.

The use of low dose atropine drops in combination with multifocal glasses has also been shown to slow the progression of myopia (Shih, Yung-Feng, et al. "An intervention trial on efficacy of atropine and multi-focal glasses in controlling myopic progression." *Acta Ophihalmologica* 79.3 (2001): 233-236).

Also, U.S. Pat. No. 6,045,578 generally describes devices and methods to treat myopia using glasses, such as to inhibit undesired growth of the eye by optically corrective devices and methods. However, this document does not relate to the use of atropine or contact lenses.

Furthermore, U.S. Pat. No. 6,752,499 generally describes the use of bifocal contact lenses to control the progression of myopia by optically corrective devices and methods. However, this document does not relate to the use of atropine.

In addition, U.S. Pat. No. 7,401,922 generally describes the use of hybrid contact lenses to control the progression of myopia by optically corrective devices and methods. However, this document does not relate to the use of atropine.

Also, U.S. Pat. No. 7,503,655 generally describes the use of eyeglasses or contact lenses for the control of the progression of myopia by optically corrective devices and methods. However, this document does not relate to the use of atropine.

Furthermore, U.S. Pat. No. 7,506,983 generally describes the use of multifocal lenses for the control of the progression of myopia by optically corrective devices and methods. However, this document does not relate to the use of atropine.

In addition, U.S. Pat. No. 7,637,612 generally describes the use of ophthalmic lenses and contact lenses for the control of the progression of myopia by optically corrective devices and methods. However, this document does not relate to the use of atropine.

Also, U.S. Pat. No. 9,101,667 generally describes the use of contact lenses that may include a medicament such as atropine for the treatment of disorders of the eye relating to vision. However, this document does not relate to printing and coatings for the contact lenses that can include atropine and the release thereof.

Furthermore, U.S. Pat. No. 9,125,808 generally describes the use of contact lenses that may include a medicament such as atropine for the treatment of disorders of the eye relating to vision. However, this document does not relate to printing and coatings for the contact lenses that can include atropine and the release thereof.

In addition, U.S. Pat. No. 9,295,693 generally describes the use of contact lenses that may include a medicament such as atropine for the treatment of disorders of the eye relating to vision. However, this document does not relate to printing and coatings for the contact lenses that can include atropine and the release thereof.

Also, U.S. Pat. No. 9,612,364 generally describes the use of contact lenses that may include a medicament such as atropine for the treatment of disorders of the eye relating to vision. However, this document does not relate to printing and coatings for the contact lenses that can include atropine and the release thereof.

Furthermore, U.S. Pat. No. 9,827,250 generally describes the use of contact lenses that may include myopia control optics that may include a medicament such as atropine for the treatment of disorders of the eye relating to vision. However, this document does not relate to printing and coatings for the contact lenses that can include atropine and the release thereof.

SUMMARY

The present invention recognizes that medical devices, such as but not limited to a contact lens, that can have atropine or other medicaments provide on or within the medical device, that can be made and used to treat myopia. Atropine or other medicaments can be released from the medical device such as a contact lens in a pharmaceutically effective amount, preferably released over time, to treat myopia in a subject. The contact lens can be a visually corrective or not visually corrective lens, a multifocal lens, an orthokeratology lens, or a combination thereof.

A first aspect of the present invention is a medical device, such as a contact lens, that included atropine and preferably can be used to treat myopia.

A second aspect of the present invention is a method of making a medical device, such as a contact lens, of the present invention.

A third aspect of the present invention is a method of using a medical device, such as a contact lens, of the present invention, preferably for the treatment of myopia.

Introduction

The present invention recognizes that medical devices, such as but not limited to contact lenses, can be made having at least one coating made at least in part using printing technologies to provide drug storage and drug release structures. The coating preferably includes at least one drug reservoir layer including at least one drug, and a least one barrier layer. The at least one barrier layer can include structures, such as but not limited to capillary structures, that alone or in combination, modulate the release of the drug from the coating.

As a non-limiting introduction to the breath of the present invention, the present invention includes several general and useful aspects, including:

1) A medical device that incorporates a drug. The medical device includes a coating that includes at least one drug reservoir layer that includes a drug and at least one barrier layer.

2) A method of making a medical device that incorporates a drug. The medical device includes a coating that includes at least one drug reservoir layer that includes a drug and at least one barrier layer. The coating is made at least in part using printing.

3) A method of using a medical device of the present invention to treat or prevent a disease, disorder or condition. The medical device can be implantable or non-implantable and is placed at a location in a subject appropriate for treating or preventing a disease, disorder or condition.

These aspects of the invention, as well as others described herein, can be achieved by using the methods, articles of manufacture and compositions of matter described herein. To gain a full appreciation of the scope of the present invention, it will be further recognized that various aspects of the present invention can be combined to make desirable embodiments of the invention.

In order to overcome problems associated with the state of the art, the present invention provides the following, and provides related benefits as well:

1. A contact lens (for example, a soft extended wear multifocal lens) from which Atropine is released at a therapeutic amount. The release can be up to the desired length of wear for treatment.
2. The new treatment option combines the effects of multifocal lens and atropine to control myopia progression. Thus, the goal is to achieve better myopia control as compared to the effect of each separately.
3. Requires a significantly smaller amount of atropine (reducing toxicity effects) due to higher bioavailability.
4. It can be worn for an extended period (up to 30 days) thus improving its adoption and the compliance rate of children wearing the lens for treatment.
5. It is a preservative free contact lens, thus reducing side effects versus the application of atropine from eye drops that use preservatives.
6. It provides comfort associated with soft contact lenses compared to hard contact lenses.

Currently, myopia is treated using atropine based eye drops, along with contact lenses that modify the shape of the eye.

Atropine eye drops use 0.01% ophthalmic solution shown to be effective in reducing the progression of myopia. Side Effects include cycloplegia (ciliary muscle paralysis, being unable to focus on nearby objects); Photophobia (extreme light sensitivity); elevation of intraocular pressures (more common in patients with a prior diagnosis of primary open angle glaucoma which is very rare in children); and Risk of angle closure glaucoma (the risk is remote in patients without a previous history).

Example #30A

General Considerations for a Contact Lens Having Atropine

An oligomer capable of free radical polymerization for use in printable formulations is prepared according to Example 3 of U.S. Pat. No. 9,931,296 B2. A printable formulation is then prepared from the oligomer according to Example 30B below. This printable formulation is then used to print a drug reservoir layer including atropine and barrier layer using the methods described in Examples 6 and Example 7 of U.S. Pat. No. 9,931,296 B2. After printing, the resulting lenses are cured using a Fusion UV Lamp for a time of approximately 5 minutes. Cured lenses are then hydrated/extracted according to Example 30C below. After hydration, lenses are inspected according to Example 4 below then placed in packaging solution as described in Example 30E below. Once packaged, the lenses are then sterilized using steam sterilization. Lenses are then allowed to equilibrate in the solution for a period of up to 14 days before being released for use. The efficacy of such lenses is demonstrated through the measurement of axial length and spherical equivalent refractive error (SER) in subjects. The eyes treated with lenses can display a smaller change in axial length and spherical equivalent refractive error (SER) relative to baseline when compared to untreated eyes. Axial length of the eye will be measured using ultrasonography and spherical equivalent refractive error (SER) can be measured using an autorefractor.

Example #30B

Printable Formulation for Ink-Jet Printing a Drug Reservoir with Atropine

The amount of the alpha beta unsaturated oligomer, or prepolymer derivative, provided in Example 3 of U.S. Pat. No. 9,931,296 B2 and 2-hydroxyethyl methacrylate (HEMA) are prepared for comparison according to the following table:
Sample Printable Formulation:

| Components | % W/W | Range (%) W/W |
|---|---|---|
| Oligomer from example 43 in U.S. pat. #US9931296B2 | 17 | 5-20 |
| Atropine | 8 | 0.001-25 |
| PEG 400 diacrylate: | 5 | 0-10 |
| N-vinyl-2-pyrrolidone monomer hydrogel: | 24 | 0-99 |
| Glycerol methacrylate monomer hydrogel: | 10 | 0-99 |
| 2-hydroxyethyl methacrylate monomer hydrogel: | 32 | 0-99 |
| Photoinitiator (Omnirad 184): | 2 | 0-10 |
| Photoinitiator (Omnirad 819): | 2 | 0-10 |
| Total | 100 | |

The viscosity and surface tension of the printable formulations are measured and the results are as follows in the following table:
Typical Physical Characteristics of Printable Formulation

| Parameter | Actual | Range |
|---|---|---|
| Viscosity (cp) | 15.4 | 1-50 |
| Surface Tension (dynes/cm) | 38.1 | 20-70 |

Example #30C

Hydration/Extraction of Printed and Cured Dry Contact Lenses

A contact lens on which the drug formulation has been printed and cured is then hydrated/extracted in a saline solution of the following formulation in the following table:

Sample Hydration/Extraction Solution Formulation

| Components | % W/W | Range (%) W/W |
|---|---|---|
| Sodium Bicarbonate | 0.5 | 0-5 |
| Pluronic F127 | 0.005 | 0-1 |
| Water | 99.495 | 90-99.9 |
| Total | 100 | |

Each lens is placed in 5 mL of this solution for 30 minutes at 50 C. After this treatment lenses are removed from the hydration/extract solution.

Example #30D

Inspection of Hydrated/extracted Contact Lenses

After hydration/extraction, lenses are removed from the solution and inspected in the wet state. The inspection includes a visual examination to assess the print quality and placement, as well as a physical examination to measure critical properties of the lenses such as base curve, diameter, power, etc.

Example #30E

Packaging of Inspected Contact Lenses

After inspection, lenses are placed into a packaging system that contains 2 mL of a packaging solution as in the below table. The packaging solution contains atropine in order to maintain an equilibrium with the drug contained by the lens. The packaging solution can also allow for uptake or release of drug by the lens depending on the concentration of drug in the solution.
Sample Packaging Solution:

| Components | % W/W | Range (%) W/W |
|---|---|---|
| Sodium Chloride | 0.9 | 0-5 |
| Sodium Bicarbonate | 0.015 | 0-5 |
| Sodium Hyaluronate | 0.15 | 0-1 |
| Atropine | 0.003 | 0-5 |
| Water | 98.932 | 90-99.9 |
| Total | 100 | |

After the lenses are placed in an appropriate packaging system such as but not limited to plastic bubble or glass vial packaging. The packaging system is sealed so as to be air tight or air resistant, as well as water tight or water resistant.

Example #31A

General Considerations for a Contact Lens Having Hyaluronic Acid

An oligomer capable of free radical polymerization for use in printable formulations is prepared according to Example 3 of U.S. Pat. No. 9,931,296 B2. Preferable oligomers include, but are not limited to HEMA, DMA, GMA, PVA, MAA, silicone or siloxane. A printable formulation is then prepared from the oligomer according to Example 31C below. This printable formulation is then used to print a drug reservoir layer including hyaluronic acid (HA) and barrier layer on the surface of a premade dry soft contact lens using the methods described in Examples 6 and Example 7 of U.S. Pat. No. 9,931,296 B2. The reservoir layer and barrier can be of the same, substantially the same, of different formulations, or a combination thereof. After printing, the resulting dry lenses with a printed drug reservoir and a printed barrier layer are cured using a Fusion UV Lamp for a time of approximately 5 minutes. Cured dry lenses are then hydrated/extracted according to Example 31D below. After hydration, lenses are inspected according to Example 31E below then placed in packaging solution as described in Example 31F below. Once packaged, the lenses are then sterilized using steam sterilization. Lenses are then allowed to equilibrate in the packaging solution for a period of up to 14 days before being released for use. The efficacy of such lenses to release hyaluronic acid is demonstrated through the measurement subjective lens comfort in patients. The hydrated contact lenses having hyaluronic acid can provide higher comfort levels relative to plain contact lenses.

Example #31B

Preparation of Spray Dried Hyaluronic Acid

Hyaluronic acid (HA) is acquired in powder form and has many sources. HA's preferred molecular weight is between 30 and 3,000,000 Daltons, with a preferred bulk density less than 0.15 gm/cm3. However, other molecular weights and bulk densities can be utilized in the present invention. A solution is then prepared from the HA and spray dried using a spray drier with optimized parameters of solution viscosity, flow rate, pressure, blower rate, inlet temperature, outlet temperature, and nozzle size in order to yield a particle diameter ranging from 0.1 to 10 microns. The particle size of the spray dried hyaluronic acid is verified through the use of laser diffraction analysis (LDA) or transmission electron microscopy (TEM).

Example #31C

Printable Formulation for Ink-Jet Printing a Drug Reservoir with Hyaluronic Acid The amount of the alpha beta unsaturated oligomer, or prepolymer derivative, provided in Example 3 of U.S. Pat. No. 9,931,296 B2 and 2-hydroxyethyl methacrylate (HEMA) are prepared for comparison according to the following table:
Sample Printable Formulation:

| Components | % (W/W) | Range (%) (W/W) |
|---|---|---|
| Oligomer from example #3 in U.S. pat. #US9931296B2 | 17 | 5-20 |
| Hyaluronic Acid (spray dried) | 8 | 0.001-25 |
| PEG 400 diacrylate: | 5 | 0-10 |
| N-vinyl-2-pyrrolidone monomer hydrogel: | 24 | 0-99 |
| Glycerol methacrylate monomer hydrogel: | 10 | 0-99 |
| 2-hydroxyethyl methacrylate monomer hydrogel: | 32 | 0-99 |
| Photoinitiator (Omnirad 184): | 2 | 0-10 |
| Photoinitiator (Omnirad 819): | 2 | 0-10 |
| Total | 100 | |

The viscosity and surface tension of the printable formulations are measured and the results are as follows in the following table:
Physical Characteristics of Printable Formulation

| | Actual | Range |
|---|---|---|
| Viscosity (cp) | 15.4 | 5-50 |
| Surface Tension (dynes/cm) | 38.1 | 20-70 |

Example #31D

Hydration/Extraction of Printed and Cured Dry Contact Lenses

The contact lens on which the drug formulation has been printed and cured is then hydrated/extracted in a saline solution of the following formulation in the following table:
Sample Hydration/Extraction Solution Formulation

| Components | % W/W | Range (%) W/W |
|---|---|---|
| Sodium Bicarbonate | 0.5 | 0-5 |
| Pluronic F127 | 0.005 | 0-1 |
| Water | 99.495 | 90-99.9 |
| Total | 100 | |

Each lens is placed in 5 mL of this solution for 30 minutes at 50 C. After this treatment lenses are removed from the hydration/extract solution.

Example #31E

Inspection of Hydrated/Extracted Contact Lenses

After hydration/extraction, lenses are removed from the solution and inspected in the wet state. The inspection includes a visual examination to assess the print quality and placement, as well as a physical examination to measure physical properties of the lenses such as base curve, diameter, power, etc.

Example #31F

Packaging of Inspected Contact Lenses

After inspection, lenses are placed into a packaging system that contains 2 mL of a packaging solution as in the table below. The packaging solution contains hyaluronic acid in order to maintain an equilibrium with the HA drug contained by the lens. The packaging solution can also allow for uptake or release of HA drug by the lens depending on the concentration of HA drug in the solution.
Sample Packaging Solution:

| Components | % W/W | Range (%) W/W |
|---|---|---|
| Sodium Chloride | 0.9 | 0-5 |
| Sodium Bicarbonate | 0.015 | 0-5 |
| Sodium Hyaluronate | 0.15 | 0-1 |
| Hyaluronic Acid | 0.003 | 0-5 |
| Water | 98.932 | 90-99.9 |
| Total | 100 | |

After the lenses are placed in an appropriate packaging system such as plastic bubble or glass vial packaging. The packaging system is sealed so as to be air tight or air resistant, as well as water tight or water resistant.

Example #32

Various Aspects of Contact Lenses for Treatment of Myopia
I. Medical Device

A first aspect of the present invention includes a medical device, including: a) a contact lens; b) at least one coating provided on at least one surface of the contact lens; and c) at least one drug provided within the coating; wherein the drug can treat, prevent, control, reduce the severity, or reduce the progression of myopia in a subject; further wherein the drug is released from the contact lens in a pharmaceutically effective amount to treat, prevent, control, reduce the severity, or reduce the progression of myopia in a subject when the medical device is operably engaged with the eye of the subject.

A. System

In another aspect of the present invention, the medical device is provided as part of a system to treat, prevent, control, reduce the severity, or reduce the progression of myopia in a subject.

In a further aspect of the present invention, the system comprises one or more of at least one packaging, at least one set of instructions, and at least one solution.

B. Contact Lens

In an additional aspect of the present invention, the contact lens includes a multi-focal contact lens, which can be a soft contact lens, a hydrogel contact lens, a silicone hydrogel contact lens, a hard contact lens, a gas permeable contact lens, or a combination thereof.

In another aspect of the present invention, the contact lens includes a bifocal contact lens, which can be a soft contact lens, a hydrogel contact lens, a silicone hydrogel contact lens, a hard contact lens, a gas permeable contact lens, or a combination thereof.

In a further aspect of the present invention, the contact lens includes an orthokeratology contact lens.

In an additional aspect of the present invention, the contact lens includes a soft contact lens, a hydrogel contact lens, a silicone hydrogel contact lens, a hard contact lens, a gas permeable contact lens, or a combination thereof.

In another aspect of the present invention, the contact lens includes a pre-made contact lens or a pre-manufactured contact lens before or after hydration.

C. Drug

In a further aspect of the present invention, the drug includes an anti-muscarinic agent, a muscarinic antagonist, a muscarinic receptor antagonist, or a combination thereof.

In another aspect of the present invention, the drug includes atropine, atropine sulphate monohydrate, pirenzepine, racanisodamine, cyclopentolate, homatropine, scopolamine, telenzepine, nuvenzepine, rispenzepine, or a combination thereof.

In a further aspect of the present invention, the drug includes atropine, atropine sulphate monohydrate, pirenzepine, or a combination thereof.

In an additional aspect of the present invention, the drug includes a dopamine agonists.

In another aspect of the present invention, the drug includes apomorphine, bromocriptine, quinpirole, levodopa, or a combination thereof.

D. Coating With Drug

In a further aspect of the present invention, the coating is made in whole or in part by printing.

In an additional aspect of the present invention, the coating is made in whole or in part by digital printing, 3D printing, digital 3D printing, or a combination thereof.

In another aspect of the present invention, the coating is made in whole or in part by additive printing, additive 3D printing, or a combination thereof.

In a further aspect of the present invention, the coating includes at least one drug reservoir layer, at least one barrier layer, or a combination thereof.

E. Release of Drug

In another aspect of the present invention, the drug is released from the medical device at a constant rate, a substantially constant rate, or kinetics of any order.

In a further aspect of the present invention, the atropine is released from the medical device intermittently, by sustained release, or a combination thereof.

F. Comfort Enhancing Agent

In an additional aspect of the present invention, further including at least one comfort enhancing agent. In another aspect of the present invention, the comfort enhancing agent includes hyaluronic acid (HA), cyclosporine, polyethylene glycol 400, hypromellose, polyvinyl alcohol, carboxymethylcellulose, dextran 70, hydroxypropyl methylcellulose, anhydrous liquid lanolin, mineral oil, white petroleum, mannitol, thiomersal, carbomer, cetrimide, glycerin, polysorbate 80, and povidine. Other comfort enhancing agents known in the art or later developed are part of the present invention.

In a further aspect of the present invention, the comfort enhancing compound is provided within the contact lens, on the surface of the contact lens, or a combination thereof.

In an additional aspect of the present invention, the comfort enhancing compound is provided on at least one surface of the contact lens by way of at least one coating.

II. Method of Making a Medical Device

A second aspect of the present invention includes a method of making a medical device of the present invention, such as but not limited to as in Section I above, for delivery of drug to the eye of a subject in need of treatment, prevention, reduction of severity, or reduction of progression of myopia, including: 1) providing a contact lens; and 2) providing a coating comprising a drug on the contact lens; wherein the drug can treat, prevent, control, reduce the severity, or reduce the progression of myopia in a subject; further wherein the drug can be released from the medical device in a pharmaceutically effective amount to treat, prevent, control, reduce of the severity, reduce the progression of myopia in a subject when the medical device is operably engaged with the eye of a subject.

III. Method of Using a Medical Device

A third aspect of the present invention includes a method of using a medical device of the present invention, such as but not limited to Section I above, for delivery of at least one drug to the eye of a subject in need of treatment, prevention, control, reduction of the severity, or reduction of progression of myopia, including: 1) providing a subject in need of treatment, prevention, control, or reduction of the severity of myopia; 2) operably engaging a medical device of claim 1 including at least one drug w the eye of the subject; wherein the drug can treat, prevent, control, reduce the severity, or reduce the progression of myopia in a subject; further wherein the drug can be released from the medical device in a pharmaceutically effective amount to treat, prevent, control, reduce of the severity, or reduce the progression of myopia in a subject when the medical device is operably engaged with the eye of the subject.

Example #33

Drug-Cell Penetrating Peptide Conjugate

An additional aspect of the present invention is that it allows for drug delivery in the posterior chamber of eye by releasing a drug conjugated to a cell penetrating peptide from the surface of a contact lens of the present invention. The present invention thus avoids the problems associated with current invasive technique like injection of a drug or surgical implants of plugs, etc.

In order to provide a drug in the posterior of eye, one can provide a layer of drugs conjugated to cell penetrating peptides. The drug can be for the treatment of wet macular degeneration such as bevacizumab, ranibizumab, lapatinib, sunitinib, or sorafenib. The cell penetrating peptides would be for penetration of the drug into the anterior segment of the eye such as TAT (derived from transactivator of transcription of human immunodeficiency virus), CC12, PNT (Penetratin), or RGD (arginine-glycine-aspartic acid).

Sustained delivery of the drug-cell penetrating peptide conjugate can facilitate delivery of drug(s) for AMD (both wet and dry AMD) to the posterior of the eye.

Example #34

Liposomes

An additional aspect of the present invention is that it allows for drug delivery in the anterior or posterior chamber of eye by releasing liposomes containing a drug from the surface of a contact lens of the present invention. The present invention thus avoids the problems associated with current invasive technique like injection of a drug or surgical implants of plugs, etc.

In order to provide a drug to the eye, one can provide a layer of liposomes containing a drug. The drug can be for the treatment of various ocular diseases such as glaucoma, macular degeneration, dry eye, or others. The liposome can include an aqueous solution core surrounded by a hydrophobic membrane in the form of a lipid bilayer that is loaded with the drug.

Sustained delivery of the liposomes containing a drug can facilitate delivery of a drug for various diseases to the anterior or posterior segment of the eye.

Example #35

Dendrimers

An additional aspect of the present invention is that it allows for drug delivery in the anterior or posterior chamber of eye by releasing dendrimers containing a drug from the surface of a contact lens of the present invention. The present invention thus avoids the problems associated with current invasive technique like injection of a drug or surgical implants of plugs, etc.

In order to provide drug to the eye, one can provide a layer of dendrimers containing a drug. The drug can be for the treatment of various ocular diseases such as glaucoma, macular degeneration, dry eye, or others. The dendrimer can include a polymeric nanoparticle (such as polyamidoamine) that is loaded with the drug.

Sustained delivery of the liposomes containing a drug can facilitate delivery of a drug for various diseases to the anterior or posterior segment of the eye.

All publications, including patent documents and scientific articles, referred to in this application and the bibliography and attachments are incorporated by reference in their entirety for all purposes to the same extent as if each individual publication were individually incorporated by reference.

All headings are for the convenience of the reader and should not be used to limit the meaning of the text that follows the heading, unless so specified.

What is claimed is:

1. A contact lens; comprising:
   a) a first surface and a second surface; and
   b) said contact lens further comprising at least one coating provided on at least a portion of said first surface, said second surface, or a combination thereof as opposed to within said contact lens;
      1) said at least one coating comprising at least one three dimensional structure; and
      2) said at least one three dimensional structure comprising:
         a. one or more drug reservoir layers:
            wherein said one or more drug reservoir layers comprise one or more drugs; and
         b. one or more barrier layers:
            wherein said one or more barrier layers modulate the release of said one or more drugs from said contact lens; and
         c. at least one Penetration Enhancer (PE).

2. The contact lens of claim 1,
   wherein said PE can be released from said contact lens when operably engaged with the surface of the eye of a subject.

3. The contact lens of claim 1,
   wherein said PE can act to enhance the penetration of at least one of said one or more drugs through ocular tissues.

4. The contact lens of claim 1,
   wherein said at least one coating comprising one or more drugs and comprising PE is provided at least in part by inkjet printing.

5. The contact lens of claim 1,
   wherein said contact lens is steam sterilized.

6. The contact lens of claim 1, further wherein said contact lens is provided in a packaging solution.

7. The contact leans of claim 1,
   further wherein said contact lens is in a packaging solution having a pH between about 6.5 and about 7.8.

8. The contact lens of claim 1,
   wherein said PE is released from said contact lens, as compared to said one or more drugs, simultaneously, separately, one after other or a combination thereof.

9. The contact lens of claim 1,
   wherein said PE is provided in liposomes, dendrimers, polymeric nanoparticles, cell penetrating peptides, or a combination thereof.

10. The contact lens of claim 9,
    wherein said cell penetrating peptide is TAT (derived from transactivator of transcription of human immunodeficiency virus), CC12, PNT (Penetratin), RGD (arginine-glycine-aspartic acid), or a combination thereof.

11. The contact lens of claim 1,
    wherein said one or more drugs, said PE, or a combination thereof, is provided in microemulsion, micelles, encapsulation, nanoparticle, microspheres, liposomes, ethosomes, niosomes, biodegradable nanoparticles, temperature sensitive smart particles, or combination thereof.

12. The contact lens of claim 1,
    wherein said one or more drugs are released from said contact lens in an effective amount to treat or prevent a disease, disorder, or condition of a subject.

13. The contact lens of claim 12,
    wherein said one or more drugs can treat, control, reduce the severity, or reduce the progression of a disease, disorder, or condition in a subject.

14. The contact lens of claim 13,
wherein said one or more drugs is Flurbiprofen, Acetazolamide, ethylenediaminetetraacetic acid, palmitoyl carnitine, sodium caprate, sodium dodecylsulphate, sodium deoxycholate, poly oxyethylene-g-lauryl ether, 1-α-lysophosphatidylocholine, deoxycholate, taurodeoxycholate, glycocholate, benzalkonium chloride, or a combination thereof.

15. The contact lens of claim 12,
wherein said subject is a human subject.

16. The contact lens of claim 12,
wherein said disease, disorder, or condition that is treated is an inflammation, an allergy, an infection, glaucoma, macular degeneration, a parasite, dry eye, eye discomfort, neovascular Age-Related Macular Degeneration (wet AMD), dry Age-Related Macular Degeneration (dry AMD), diabetic retinopathy, or a combination thereof.

17. The contact lens of claim 1,
wherein said one or more drugs comprises at least one small molecule drug, at least one biological drug, at least one encapsulated drug, at least one nanoparticle, at least one dispersed drug, or a combination thereof.

18. The contact lens of claim 17,
wherein said at least one biological drug comprises at least one protein comprising at least one enzyme, at least one transport protein, at least one structural protein, at least one storage protein, at least one hormone protein, at least one receptor protein, at least one contractile protein, at least one antibody, at least one monoclonal antibody, or a combination thereof.

19. The contact lens of claim 1, wherein said one or more drugs comprises an anti-inflammatory agent, an anti-allergy agent, an anti-infective agent, an antibiotic, an anti-parasitic agent, an anti-glaucoma agent, an anti-macular degeneration agent, an ophthalmic drug, a steroid, an anti-dry eye agent, a comfort agent, or a combination thereof.

20. The contact lens of claim 19,
wherein said comfort agent is hyaluronic acid (HA).

21. A contact lens; comprising:
a) a first surface and a second surface;
b) at least one Penetration Enhancer (PE); and
c) said contact lens further comprising at least one coating provided on at least a portion of said first surface, said second surface, or a combination thereof as opposed to within said contact lens;
  1) said at least one coating comprising at least one three dimensional structure; and
  2) said at least one three dimensional structure comprising:
    a. one or more drug reservoir layers; wherein said one or more drug reservoir layers comprise one or more drugs; and
    b. one or more barrier layers;
wherein said one or more barrier layers modulate the release of said one or more drugs from said drug delivery contact lens.

* * * * *